United States Patent
Lin et al.

(10) Patent No.: US 11,634,490 B2
(45) Date of Patent: Apr. 25, 2023

(54) BLOCKING ANTIBODIES AGAINST CD47 AND METHODS OF USE THEREOF

(71) Applicant: Accurus Biosciences, Inc., Richmond, CA (US)

(72) Inventors: Haishan Lin, Moraga, CA (US); Yi Zhang, Dublin, CA (US)

(73) Assignee: Accurus Biosciences, Inc., Richmond, CA (US)

( * ) Notice: Subject to any disclaimer, the term of this patent is extended or adjusted under 35 U.S.C. 154(b) by 204 days.

(21) Appl. No.: 17/058,076

(22) PCT Filed: Jun. 14, 2019

(86) PCT No.: PCT/US2019/037353
§ 371 (c)(1),
(2) Date: Nov. 23, 2020

(87) PCT Pub. No.: WO2019/241732
PCT Pub. Date: Dec. 19, 2019

(65) Prior Publication Data
US 2021/0206850 A1 Jul. 8, 2021

Related U.S. Application Data

(60) Provisional application No. 62/685,594, filed on Jun. 15, 2018.

(51) Int. Cl.
| | | |
|---|---|---|
| *A61K 39/00* | (2006.01) |
| *A61K 39/395* | (2006.01) |
| *G01N 33/53* | (2006.01) |
| *C12N 5/02* | (2006.01) |
| *C12N 5/20* | (2006.01) |
| *C07K 16/00* | (2006.01) |
| *C07K 16/46* | (2006.01) |
| *C07K 16/28* | (2006.01) |

(52) U.S. Cl.
CPC .... *C07K 16/2803* (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,759,025 B2 | 6/2014 | Kikuchi et al. |
| 2014/0140989 A1 | 5/2014 | Eckelman et al. |
| 2015/0274826 A1 | 10/2015 | Frazier et al. |
| 2017/0081407 A1 | 3/2017 | Grosveld et al. |

FOREIGN PATENT DOCUMENTS

| | | |
|---|---|---|
| WO | WO 2011/076781 | 6/2011 |
| WO | WO 2013/119714 | 8/2013 |
| WO | WO 2014/179132 | 11/2014 |
| WO | WO 2016/081423 | 5/2016 |
| WO | WO 2016/109415 | 7/2016 |
| WO | WO 2017/053423 | 3/2017 |
| WO | WO 2018/089508 | 5/2018 |

OTHER PUBLICATIONS

Takimoto et al. The Macrophage 'Do not eat me' signal, CD47, is a clinically validated cancer immunotherapy target. Industry Corner: Perspectives and Controversies, 30(3):p. 486-489, Mar. 1, 2019. (Year: 2019).*
Chao et al. The CD47-SIRPα Pathway in Cancer Immune Evasion and Potential Therapeutic Implications. Curr Opin Immunol. Apr. 2012 ; 24(2): 225-232. (Year: 2012).*
Hayat et al. CD47: role in the immune system and application to cancer therapy. Cellular Oncology (2020) 43:19-30. (Year: 2020).*
Wernig et al. Unifying mechanism for different fibrotic diseases. PNAS, 114(18):4757-4762, 2017. (Year: 2017).*
Tao et al. CD47 Deficiency in Mice Exacerbates Chronic Fatty Diet-Induced Steatohepatitis Through its Role in Regulating Hepatic Inflammation and Lipid Metabolism. Front Immunol. Feb. 25, 2020;11:148. (Year: 2020).*
Lerbs et al. CD47 prevents the elimination of diseased fibroblasts in scleroderma. JCI Insight. Aug. 20, 2020; 5(16): e140458. (Year: 2020).*
Gao et al. THBS1/CD47 Modulates the Interaction of γ-Catenin With E-Cadherin and Participates in Epithelial-Mesenchymal Transformation in Lipid Nephrotoxicity. Front Cell Dev Biol. 2020; 8: 601521. (Year: 2020).*
Cui et al. Activation of JUN in fibroblasts promotes pro-fibrotic programme and modulates protective immunity. Nature Communications vol. 11, Article No. 2795 (Year: 2020).*
Conger, K., Fibrosis reversed when 'don't eat me' signal blocked. Stanford Medicine News Center., pp. 1-5. Apr. 17, 2017. (Year: 2017).*
International Search Report & Written Opinion dated Oct. 1, 2019 for PCT/US2019/037353. 12 pages.
Extended European Search Report and Opinion dated May 20, 2022 for EP Application No. 19818886.4. 15 pages.

* cited by examiner

*Primary Examiner* — Maher M Haddad
(74) *Attorney, Agent, or Firm* — Sheppard Mullin Richter & Hampton LLP

(57) ABSTRACT

Provided are anti-CD47 antibodies or fragments thereof that can bind to the extra cellular domain of the CD47 protein. The antibodies or fragments thereof can effectively block the interaction between human CD47 and its ligand SIRP alpha and enhance the phagocytosis activity of macrophages to engulf cancer cells. Some of these antibodies or fragments do not induce in vitro hemagglutination and therefore can be suitably used as therapeutic agents with reduced off-target effects.

17 Claims, 20 Drawing Sheets

Specification includes a Sequence Listing.

D36S4 hIgG1 control

D28S1

AB6.12

BLOCKING ANTIBODIES AGAINST CD47 AND METHODS OF USE THEREOF

CROSS REFERENCE TO RELATED APPLICATIONS

This application is the U.S. national stage application of International Application PCT/US2019/037353, filed Jun. 14, 2019, which claims the benefit under 35 U.S.C. § 119(e) of the U.S. Provisional Application Ser. No. 62/685,594, filed Jun. 15, 2018, the content of each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Oct. 31, 2022, is named 271340_ST25.txt and is 48,769 bytes in size.

BACKGROUND

CD47 is a multi-span transmembrane receptor, a member of the immunoglobulin (Ig) superfamily, and acts to regulate phagocytosis by macrophages and dendritic cells. CD47 is widely expressed in normal tissues but is highly expressed on cell surface of many types of cancer, including human acute myeloid leukemia (AML), non-Hodgkin's lymphoma (NHL), and solid tumors such as small-cell lung cancer (SCLC). Essentially all known human cancers, including both solid tumors and leukemia, express CD47, rendering CD47 a universal cancer therapeutic target.

Cancer cells utilize multiple mechanisms to evade programmed cell removal, for example, the phagocytic elimination of abnormal cells by innate immune cells including macrophages, dendritic cells, and neutrophils. The inhibition of programmed cell removal is predominantly inhibited by the critical molecule CD47. CD47 overexpression represents one of the mechanisms cancer cells employ to evade immune surveillance and correlates with poor prognosis in cancer.

CD47 interacts with multiple proteins, including in cis with integrins and in trans with two ligands, thrombospondin-1 (TSP-1) and signal regulatory protein alpha (SIRPα). SIRPα encodes an Ig-superfamily receptor whose cytoplasmic region contains immunoreceptor tyrosine-based inhibition motifs (ITIMs) and is expressed on macrophages, dendritic cells, and neurons. Binding of CD47 to its receptor, SIRPα, on macrophages leads to inhibition of macrophage activation and phagocytosis. Previous preclinical studies suggested that blocking CD47 interaction with its ligand, SIRPα, by either anti-CD47 blocking antibodies or a SIRPα decoy receptor can lead to increased macrophage phagocytosis and reduced tumor growth.

SUMMARY

The present disclosure provides anti-CD47 antibodies having a range of binding affinities to human CD47 proteins and can effectively block the interaction between human CD47 and its ligand SIRP alpha. Also importantly, the examples demonstrate that these anti-CD47 antibodies enhance the phagocytosis activity of macrophage to engulf cancer cells, such as B lymphoma cells. Different from known anti-CD47 antibodies that can induce red blood cell hemagglutination in the in vitro settings, some of these antibodies do not induce in vitro hemagglutination. These antibodies may have lower side effects on human red blood cells in vivo. These anti-CD47 antibodies are useful for therapeutic purposes such as treating various types of cancer, as well as infections, and can also be used for diagnostic and prognostic purposes. Antigen binding fragments that can induce hemagglutination, on the other hand, may be used to prepare bispecific antibodies or prodrugs that deliver the antibodies inside target cells.

In one embodiment, the present disclosure provides an antibody or fragment thereof having binding specificity to a human CD47 (cluster of differentiation 47) protein, wherein the antibody or fragment thereof can bind to the CD47 on a cell, block the binding of the CD47 to a human signal-regulatory protein alpha (SIRPα), and promote macrophage phagocytosis of the cell. In some embodiments, the antibody or fragment thereof does not induce hemagglutination in vitro. In some embodiments, the antibody or fragment thereof induce hemagglutination in vitro.

In another embodiment, provided is an antibody or fragment thereof having binding specificity to a human CD47 (cluster of differentiation 47) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1, CDRL2, and CDRL3, and the CDRH1, CDRH2, and CDRH3 are independently selected from the CDRL1, CDRL2, and CDRL3 combinations and the CDRH1, CDRH2, and CDRH3 combinations in Table A wherein each of the CDRL1, CDRL2, CDRL3, CDRH1, CDRH2, and CDRH3 in Table A can include one, two, or three amino acid addition, deletion, conservative amino acid substitution or the combinations thereof.

In some embodiments, the CDRL1, CDRL2, and CDRL3, and the CDRH1, CDRH2, and CDRH3 are independently selected from the CDRL1, CDRL2, and CDRL3 combinations and the CDRH1, CDRH2, and CDRH3 combinations in Table A.

Also, in another embodiment, provided is an antibody or fragment thereof having binding specificity to a human CD47 (cluster of differentiation 47) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises the amino acid sequence of TDIDDD (SEQ ID NO:1) or an amino acid sequence having one, two or three amino acid substitution from SEQ ID NO:1, the CDRL2 comprises the amino acid sequence of EGN or an amino acid sequence having one or two amino acid substitution from EGN, the CDRL3 comprises the amino acid sequence of LQSDNLPYT (SEQ ID NO:3) or an amino acid sequence having one, two or three amino acid substitution from SEQ ID NO:3, the CDRH1 comprises the amino acid sequence of GFTFTSYG (SEQ ID NO:4) or an amino acid sequence having one, two or three amino acid substitution from SEQ ID NO:4, the CDRH2 comprises the amino acid sequence of INTGGSYT (SEQ ID NO:5) or an amino acid sequence having one, two or three amino acid substitution from SEQ ID NO:5, and the CDRH3 comprises the amino acid sequence of HTIKSLMDY (SEQ ID NO:6) or an amino acid sequence having one, two or three amino acid substitution from SEQ ID NO:6. In some embodiments, the CDRL1, CDRL2, CDRL3, CDRH1, CDRH2 and CDRH3 comprise the amino acid sequence of SEQ ID NO:1, (EGN), 3-6, respectively.

In some embodiments, the antibody or fragment comprises a light chain variable region having a Leu at position 46, according to Kabat numbering. In some embodiments, the antibody or fragment comprises a light chain variable region comprising an amino acid sequence selected from the group consisting of SEQ ID NO: 44 and 64-69, and a heavy chain variable region comprising an amino acid sequence selected from the group consisting of SEQ ID NO: 42 and 61-63. In some embodiments, the antibody or fragment comprises a light chain variable region comprising an amino acid sequence selected from the group consisting of SEQ ID NO: 40, 44, 48, 52, 56, and 60, or a peptide having at least 90% sequence identity to an amino acid sequence selected from the group consisting of SEQ ID NO: 40, 44, 48, 52, 56, and 60.

In some embodiments, the antibody or fragment comprises a heavy chain variable region comprising an amino acid sequence selected from the group consisting of SEQ ID NO: 38, 42, 46, 50, 54 and 58, or a peptide having at least 90% sequence identity to an amino acid sequence selected from the group consisting of SEQ ID NO: 38, 42, 46, 50, 54 and 58.

Another embodiment of the present disclosure provides an antibody or fragment thereof having binding specificity to a human CD47 (cluster of differentiation 47) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises the amino acid sequence of QSLFKSRTRKNY (SEQ ID NO:13) or an amino acid sequence having one, two or three amino acid substitution from SEQ ID NO:13, the CDRL2 comprises the amino acid sequence of WAS or an amino acid sequence having one or two amino acid substitution from WAS, the CDRL3 comprises the amino acid sequence of KQSYYLLT (SEQ ID NO:15) or an amino acid sequence having one, two or three amino acid substitution from SEQ ID NO:15, the CDRH1 comprises the amino acid sequence of GFTFSRYW (SEQ ID NO:16) or an amino acid sequence having one, two or three amino acid substitution from SEQ ID NO:16, the CDRH2 comprises the amino acid sequence of IRLKSDNYET (SEQ ID NO:17) or an amino acid sequence having one, two or three amino acid substitution from SEQ ID NO:17, and the CDRH3 comprises the amino acid sequence of IEEGGYYVPFAY (SEQ ID NO:18) or an amino acid sequence having one, two or three amino acid substitution from SEQ ID NO:18.

In some embodiments, the CDRL1, CDRL2, CDRL3, CDRH1, CDRH2 and CDRH3 comprise the amino acid sequence of SEQ ID NO:13, (WAS), 15-18, respectively. In some embodiments, the antibody or fragment comprises a light chain variable region comprising an amino acid sequence selected from the group consisting of SEQ ID NO: 2, 48 and 82, and a heavy chain variable region comprising an amino acid sequence selected from the group consisting of SEQ ID NO: 46 and 79-81.

In some embodiments, the antibody or fragment further has a binding specificity to a second target protein. The second target protein, in some embodiments, is selected from the group consisting of IL-1, CD3, CD16, CD19, CD28, CD64, PD-1, PD-L1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA and KIR.

Also provided, in one embodiment, is a fusion protein comprising an antibody or fragment of the present disclosure, a blocking peptide, and a peptide linker connecting the antibody or fragment and the blocking peptide, wherein the peptide linker can be digested by a protease expressed in a tumor environment. In some embodiments, the protease is selected from the group consisting of MMP-1, MMP-2, MMP-3, MMP-8, MMP-9, MMP-14, uPA, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase10, Caspase-11, Caspase-12, Caspase-13, Caspase-14, and TACE.

Compositions are also provided. In one embodiment, the composition comprises the antibody or fragment thereof of or the fusion protein of the present disclosure and a pharmaceutically acceptable carrier. Also provided is an isolated cell comprising one or more polynucleotide encoding the antibody or fragment thereof or the fusion protein of the present disclosure.

The present disclosure provides, in one embodiment, a method of treating cancer or fibrosis in a patient in need thereof, comprising administering to the patient the antibody or fragment thereof or the fusion protein of the present disclosure. Non-limiting examples of cancers include bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

Yet in another embodiment, provided is a method of detecting expression of a CD47 protein in a sample, comprising contacting the sample with an antibody or fragment thereof of the present disclosure under conditions for the antibody or fragment thereof to bind to the CD47 protein, and detecting the binding which indicates expression of CD47 protein in the sample.

DETAILED DESCRIPTION

Definitions

Figure 1:
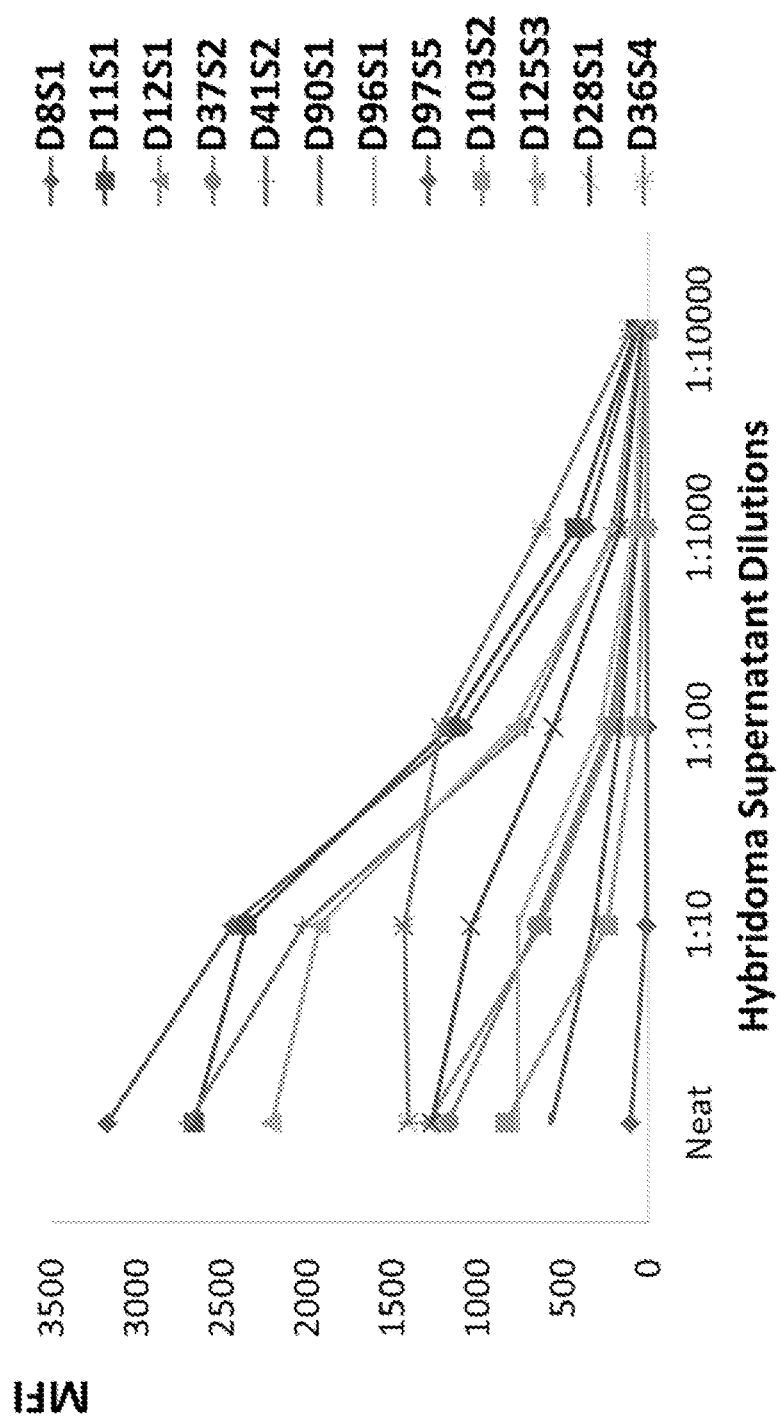
FIG. 1 shows the anti-human CD47 hybridoma supernatant binding to human CD47-expressing CHO cells.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-CD47 Antibodies

Many tumor cells overexpress CD47 to escape immunosurveilance of host immune system. CD47 binds to its receptor signal regulatory protein alpha (SIRPα) and downregulate phagocytosis of tumor cell. Therefore, anti-CD47 therapies aim to restore clearance of tumor cells. A number of therapeutics are being developed, including anti-CD47 antibodies, engineered decoy receptors, anti-SIRPα antibodies and bispecific agents.

As noted above, however, the CD47 protein is also expressed on normal cell. Therefore, targeting CD47 too broadly may give rise to undesired adverse effects. Further, it has been observed that some known anti-CD47 antibodies induce red blood cell hemagglutination in vitro.

In accordance with one embodiment of the present disclosure, antibodies and fragments thereof are provided that specifically bind to the human CD47 protein. In one embodiment, represented by D28S1 and its chimeric and humanized counterparts, the antibodies and fragments thereof can bind to the cell surface CD47 protein at a relatively high affinity, and block the binding of the CD47 protein to a human signal-regulatory protein alpha (SIRPα) at a relatively high inhibition efficiency.

In some embodiments, the antibodies or fragments can block the binding of the CD47 protein to the human SIRPα at an inhibition efficiency with IC50 ranging from 0.09 to 1.94 μg/ml.

In some embodiments, the antibodies or fragments do not induce hemagglutination in vitro or in vivo. In some embodiments, inducement of hemagglutination is measured in the hemagglutination assay using human whole blood or purified human red blood cells.

Antibodies and fragments of the present disclosure are also described with respect to their CDR sequences. In one embodiment, an antibody or fragment thereof is provided that has binding specificity to a human CD47 protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1, CDRL2, and CDRL3 combination, and the CDRH1, CDRH2, and CDRH3 combination can independently be selected from Table A.

TABLE A

CDR combinations for anti-CD47 antibodies

| Comb # | CDRL combinations | | | CDRH combinations | | |
|---|---|---|---|---|---|---|
| | CDRL1 | CDRL2 | CDRL3 | CDRH1 | CDRH2 | CDRH3 |
| 1 SEQ ID NO: | TDIDDD 1 | EGN | LQSDNLPYT 3 | GFTFTSYG 4 | INTGGSYT 5 | HTIKSLMDY 6 |
| 2 SEQ ID NO: | QDISNH 7 | YTS | QQGSTLPFT 9 | GFNIKNTY 10 | IDPANGNT 11 | GYGSGFAY 12 |
| 3 SEQ ID NO: | QSLFKSRTRKNY 13 | WAS | KQSYYLLT 15 | GFTFSRYW 16 | IRLKSDNYET 17 | IEEGGYYVPFAY 18 |
| 4 SEQ ID NO: | QDISNH 19 | YTS | QQGSTLPFT 21 | GFNIKNTY 22 | IDPANGNT 23 | GYGSGFAY 24 |
| 5 SEQ ID NO: | QDISNH 25 | YTS | QQGSTFPYT 27 | GFNIKDTY 28 | IDPANGNI 29 | SYGSSFAS 30 |
| 6 SEQ ID NO: | ESVDEFGISY 31 | RAS | QQSNQDPLT 33 | GFTFSDYG 34 | ISKYGTYT 35 | RFFGNYNYWYFDV 36 |

It can be readily appreciated that certain modification (e.g., one, two, or three amino acid addition, deletion, conservative amino acid substitution) to one or more of the CDR sequences can be made while retaining the binding activity of the antibody or fragment. In some embodiments, the modifications are amino acid substitution of one, two, or three residues.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

| Amino Acid Similarity Matrix |
|---|

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 |   |
| F | −4 | −5 | −5 | −3 | −4 | −3 | −6 | −5 | −4 | −5 | −2 | −5 | −4 | −1 | 0 | 1 | 2 | 9 |   |   |
| L | −6 | −4 | −3 | −3 | −2 | −2 | −4 | −3 | −3 | −2 | −2 | −3 | −3 | 2 | 4 | 2 | 6 |   |   |   |
| I | −2 | −3 | −2 | −1 | −1 | 0 | −2 | −2 | −2 | −2 | −2 | −2 | −2 | 4 | 2 | 5 |   |   |   |   |
| M | −5 | −3 | −2 | −2 | −1 | −1 | −3 | −2 | 0 | −1 | −2 | 0 | 0 | 2 | 6 |   |   |   |   |   |
| V | −2 | −1 | −1 | −1 | 0 | 0 | −2 | −2 | −2 | −2 | −2 | −2 | −2 | 4 |   |   |   |   |   |   |
| R | −4 | −3 | 0 | 0 | −2 | −1 | −1 | −1 | 0 | 1 | 2 | 3 | 6 |   |   |   |   |   |   |   |
| K | −5 | −2 | −1 | 0 | −1 | 0 | 0 | 0 | 1 | 1 | 0 | 5 |   |   |   |   |   |   |   |   |
| H | −3 | −2 | 0 | −1 | −1 | −1 | 1 | 1 | 2 | 3 | 6 |   |   |   |   |   |   |   |   |   |
| Q | −5 | −1 | 0 | −1 | 0 | −1 | 2 | 2 | 1 | 4 |   |   |   |   |   |   |   |   |   |   |
| N | −4 | 0 | −1 | 1 | 0 | 0 | 2 | 1 | 2 |   |   |   |   |   |   |   |   |   |   |   |
| E | −5 | 0 | −1 | 0 | 0 | 0 | 3 | 4 |   |   |   |   |   |   |   |   |   |   |   |   |
| D | −5 | 1 | −1 | 0 | 0 | 0 | 4 |   |   |   |   |   |   |   |   |   |   |   |   |   |
| T | −2 | 0 | 0 | 1 | 1 | 3 |   |   |   |   |   |   |   |   |   |   |   |   |   |   |
| A | −2 | 1 | 1 | 1 | 2 |   |   |   |   |   |   |   |   |   |   |   |   |   |   |   |
| S | 0 | 1 | 1 | 1 |   |   |   |   |   |   |   |   |   |   |   |   |   |   |   |   |
| P | −3 | −1 | 6 |   |   |   |   |   |   |   |   |   |   |   |   |   |   |   |   |   |
| G | −3 | 5 |   |   |   |   |   |   |   |   |   |   |   |   |   |   |   |   |   |   |
| C | 12 |   |   |   |   |   |   |   |   |   |   |   |   |   |   |   |   |   |   |   |

| Conservative Amino Acid Substitutions | |
|---|---|
| For Amino Acid | Substitution With |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Specific example antibodies include those that have a heavy chain sequence of SEQ ID NO: 38, 42, 46, 50, 54 and 58 and/or a light chain sequence of SEQ ID NO: 40, 44, 48, 52, 56, and 60, and their respective biological variants.

In one embodiment, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1 comprises the amino acid sequence of TDIDDD (SEQ ID NO:1) or an amino acid sequence having one, two or three amino acid substitution from SEQ ID NO:1, the CDRL2 comprises the amino acid sequence of EGN or an amino acid sequence having one or two amino acid substitution from EGN, the CDRL3 comprises the amino acid sequence of LQSDNLPYT (SEQ ID NO:3) or an amino acid sequence having one, two or three amino acid substitution from SEQ ID NO:3, the CDRH1 comprises the amino acid sequence of GFTFTSYG (SEQ ID NO:4) or an amino acid sequence having one, two or three amino acid substitution from SEQ ID NO:4, the CDRH2 comprises the amino acid sequence of INTGGSYT (SEQ ID NO:5) or an amino acid sequence having one, two or three amino acid substitution from SEQ ID NO:5, and the CDRH3 comprises the amino acid sequence of HTIKSLMDY (SEQ ID NO:6) or an amino acid sequence having one, two or three amino acid substitution from SEQ ID NO:6.

The antibodies and fragments of the present disclosure can be mouse antibodies or fragments, chimeric antibodies or fragments, or humanized antibodies or fragments. For humanized antibodies and fragments, certain back mutations to the mouse counterpart can be introduced, for example.

Example back-mutations are shown in Table 4 to be useful for retaining certain characteristics of the anti-CD47 antibodies. Accordingly, in some embodiments, the anti-CD47 antibodies or fragments thereof of the present disclosure, include one or more of the back-mutations. In some embodiments, the back-mutation in the heavy chain can be one or more of 30T, 49A or 44R. In one embodiment, the back-mutation in the heavy chain includes both 30T and 49A.

In some embodiments, back-mutation in the light chain can be one or more of 46L, 58V, 47L, 49S, 20T, and 22R. In one embodiment, the back-mutation in the light chain includes 46L. In one embodiment, the back-mutation in the light chain includes 46L and 58V. In one embodiment, the back-mutation in the light chain includes 46L and 47L. In one embodiment, the back-mutation in the light chain includes 46L, 47L and 49S. In one embodiment, the back-mutation in the light chain includes 46L, 20T and 22R.

In some embodiments, the anti-CD47 antibody of the present disclosure includes a VH of any one of SEQ ID NO: 42 and 61-63, a VL of any one of SEQ ID NO: 44 and 64-69, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 61, for instance, can be a VH that has an overall 80%, 85%, 90%, 95%, 98% or 99% sequence identity to SEQ ID NO:61 but retains the CDRs, and optionally retains one or more, or all of the back-mutations.

In another example, in the antibody or fragment thereof, the CDRL1 comprises the amino acid sequence of QSLFKSRTRKNY (SEQ ID NO:13), the CDRL2 comprises the amino acid sequence of WAS, the CDRL3 comprises the amino acid sequence of KQSYYLLT (SEQ ID NO:15), the CDRH1 comprises the amino acid sequence of GFTFSRYW (SEQ ID NO:16), the CDRH2 comprises the amino acid sequence of IRLKSDNYET (SEQ ID NO:17), and the CDRH3 comprises the amino acid sequence of IEEGGYYVPFAY (SEQ ID NO:18).

The antibodies and fragments of the present disclosure can be mouse antibodies or fragments, chimeric antibodies or fragments, or humanized antibodies or fragments. For humanized antibodies and fragments, certain back mutations to the mouse counterpart can be introduced, for example.

Example back-mutations for these antibodies or fragments are shown in Table 7 to be useful for retaining certain characteristics of the anti-CD47 antibodies. In some embodiments, the back-mutation in the heavy chain can be one or more of 99I, 100E or 49A. In one embodiment, the back-mutation in the heavy chain includes both 99I and 100E.

In some embodiments, the anti-CD47 antibody of the present disclosure includes a VH of any one of SEQ ID NO: 46 and 79-81, a VL of any one of SEQ ID NO: 2, 48 and 82, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO:79, for instance, can be a VH that has an overall 80%, 85%, 90%, 95%, 98% or 99% sequence identity to SEQ ID NO:79 but retains the CDRs, and optionally retains one or more, or all of the back-mutations.

In one embodiment, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1 comprises the amino acid sequence of SEQ ID NO:7 or an amino acid sequence having one, two or three amino acid substitution from SEQ ID NO:7, the CDRL2 comprises the amino acid sequence of YTS or an amino acid sequence having one or two amino acid substitution from YTS, the CDRL3 comprises the amino acid sequence of SEQ ID NO:9 or an amino acid sequence having one, two or three amino acid substitution from SEQ ID NO:9, the CDRH1 comprises the amino acid sequence of SEQ ID NO:10 or an amino acid sequence having one, two or three amino acid substitution from SEQ ID NO:10, the CDRH2 comprises the amino acid sequence of SEQ ID NO:11 or an amino acid sequence having one, two or three amino acid substitution from SEQ ID NO:11, and the CDRH3 comprises the amino acid sequence of SEQ ID NO:12 or an amino acid sequence having one, two or three amino acid substitution from SEQ ID NO:12.

In some embodiments, the anti-CD47 antibody of the present disclosure includes a VH of SEQ ID NO: 38 or 50, a VL of SEQ ID NO: 40 or 52, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 38, for instance, can be a VH that has an overall 80%, 85%, 90%, 95%, 98% or 99% sequence identity to SEQ ID NO:38 but retains the CDRs, and optionally retains one or more back-mutations.

In one embodiment, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1 comprises the amino acid sequence of SEQ ID NO:19 or an amino acid sequence having one, two or three amino acid substitution from SEQ ID NO:19, the CDRL2 comprises the amino acid sequence of YTS or an amino acid sequence having one or two amino acid substitution from YTS, the CDRL3 comprises the amino acid sequence of SEQ ID NO:21 or an amino acid sequence having one, two or three amino acid substitution from SEQ ID NO:21, the CDRH1 comprises the amino acid sequence of SEQ ID NO:22 or an amino acid sequence having one, two or three amino acid substitution from SEQ ID NO:22, the CDRH2 comprises the amino acid sequence of SEQ ID NO:23 or an amino acid sequence having one, two or three amino acid substitution from SEQ ID NO:23, and the CDRH3 comprises the amino acid sequence of SEQ ID NO:24 or an amino acid sequence having one, two or three amino acid substitution from SEQ ID NO:24.

In some embodiments, the anti-CD47 antibody of the present disclosure includes a VH of SEQ ID NO: 38 or 50, a VL of SEQ ID NO: 40 or 52, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 38, for instance, can be a VH that has an overall 80%, 85%, 90%, 95%, 98% or 99% sequence identity to SEQ ID NO:38 but retains the CDRs, and optionally retains one or more back-mutations.

In one embodiment, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1 comprises the amino acid sequence of SEQ ID NO:25 or an amino acid sequence having one, two or three amino acid substitution from SEQ ID NO:25, the CDRL2 comprises the amino acid sequence of YTS or an amino acid sequence having one or two amino acid substitution from YTS, the CDRL3 comprises the amino acid sequence of SEQ ID NO:27 or an amino acid sequence having one, two or three amino acid substitution from SEQ ID NO:27, the CDRH1 comprises the amino acid sequence of SEQ ID NO:28 or an amino acid sequence having one, two or three amino acid substitution from SEQ ID NO:28, the CDRH2 comprises the amino acid sequence of SEQ ID NO:29 or an amino acid sequence having one, two or three amino acid substitution from SEQ ID NO:29, and the CDRH3 comprises the amino acid sequence of SEQ ID NO:30 or an amino acid sequence having one, two or three amino acid substitution from SEQ ID NO:30.

In some embodiments, the anti-CD47 antibody of the present disclosure includes a VH of SEQ ID NO: 54, a VL of SEQ ID NO: 56, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 54, for instance, can be a VH that has an overall 80%, 85%, 90%, 95%, 98% or 99% sequence identity to SEQ ID NO:54 but retains the CDRs, and optionally retains one or more back-mutations.

In one embodiment, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1 comprises the amino acid sequence of SEQ ID NO:31 or an amino acid sequence having one, two or three amino acid substitution from SEQ ID NO:31, the CDRL2 comprises the amino acid sequence of RAS or an amino acid sequence having one or two amino acid substitution from RAS, the CDRL3 comprises the amino acid sequence of SEQ ID NO:33 or an amino acid sequence having one, two or three amino acid substitution from SEQ ID NO:33, the CDRH1 comprises the amino acid sequence of SEQ ID NO:34 or an amino acid sequence having one, two or three amino acid substitution from SEQ ID NO:34, the CDRH2 comprises the amino acid sequence of SEQ ID NO:35 or an amino acid sequence having one, two or three amino acid substitution from SEQ ID NO:35, and the CDRH3 comprises the amino acid sequence of SEQ ID NO:36 or an amino acid sequence having one, two or three amino acid substitution from SEQ ID NO:36.

In some embodiments, the anti-CD47 antibody of the present disclosure includes a VH of SEQ ID NO: 58, a VL of SEQ ID NO: 60, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 58, for instance, can be a VH that has an overall 80%, 85%, 90%, 95%, 98% or 99% sequence identity to SEQ ID NO:58 but retains the CDRs, and optionally retains one or more back-mutations.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Antibody Prodrugs

Antibody prodrugs can be constructed that have improved tumor cell specificity and/or reduced non-target cell binding, resulting in improved anti-tumor efficiency. An antibody prodrug can be a fusion protein that includes a blocking peptide fused, optionally through a peptide linker, to the antibody or fragment targeting CD47.

A "blocking peptide" is a peptide which, given its size and location relative to the antibody or fragment, inhibits or reduces the binding of the antibody or fragment to the target epitope. The blocking peptide be fused to the N terminus of the heavy chain or light chain of the antibody or fragment, or placed at the C terminus. Examples of blocking peptides can be found in, e.g., Desnoyers et al., "Tumor-specific activation of an EGFR-targeting probody enhances therapeutic index," *Sci Transl Med.* 2013 Oct. 16; 5(207): 207ra144.

In some embodiments, the prodrug does not have to be a fusion protein. Instead, the blocking peptide can be linked or conjugated any residue inside the anti-CD47 heavy or light chain.

The peptide linker can include a binding site for a protease that expresses at a higher or higher level in tumors or tumor microenvironment. Non-limiting examples of proteases include MMP-1, MMP-2, MMP-3, MMP-8, MMP-9, MMP-14, uPA, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase10, Caspase-11, Caspase-12, Caspase-13, Caspase-14, and TACE.

The prodrugs of the present disclosure may not bind to human CD47 on normal human red blood cells in circulation. Thus, the anti-CD47 prodrug will have reduced toxicity to RBCs or other non-tumor cells and an improved PK profiles in circulation. In the tumor microenvironment, the proteases can cleave the blocking peptide off the anti-CD47 prodrug and the anti-CD47 prodrug will become active in binding CD47 on tumor cells. In some embodiments, the antibody or fragment in the prodrug is any that is disclosed in the present disclosure. In some embodiments, the antibody or fragment is one of those that induce hemagglutination such as D36S4 and its derivatives.

Bi-Functional Molecules

CD47 plays an important role in immune and angiogenic responses. It is contemplated that bi-functional molecules that combine an anti-CD47 antibody or fragment with another molecule or fragment that has specificity (second specificity) to a cytokine, an immune checkpoint, or a cancer antigen would have synergistic effect in treatments.

In some embodiments, the second specificity is to a molecule selected from IL-1, CD3, CD16, CD19, CD28, and CD64. Other examples include PD-1, PD-L1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs).

As an immune checkpoint inhibitor, an antibody or antigen-binding fragment specific to CD47 can be combined with a second antigen-binding fragment specific to a tumor antigen to generate a bispecific antibody. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, $\alpha V\beta 3$, $\alpha 5\beta 1$, ERBB2, ERBB3, MET, IGF1R, EPHA3, TRAILR1, TRAILR2, RANKL, FAP and Tenascin.

Different format of bispecific antibodies are also provided. In some embodiments, each of the anti-CD47 fragment and the second fragment each is independently selected from a Fab fragment, a single-chain variable fragment (scFv), or a single-domain antibody. In some embodiments, the bispecific antibody further includes a Fc fragment.

Bifunctional molecules that include not just antibody or antigen binding fragment are also provided. As a tumor antigen targeting molecule, an antibody or antigen-binding fragment specific to CD47, such as those described here, can be combined with an immune cytokine or ligand optionally through a peptide linker. The linked immune cytokines or ligands include, but not limited to, IL-1, IL-2, IL-3, IL-4, IL-5, IL-6, IL-7, IL-10, IL-12, IL-13, IL-15, GM-CSF, TNF-$\alpha$, CD40L, OX40L, CD27L, CD30L, 4-1BBL, LIGHT and GITRL. Such bi-functional molecules can combine the immune checkpoint blocking effect with tumor site local immune modulation.

Polynucleotides Encoding the Antibodies and Methods of Preparing the Antibodies

The present disclosure also provides isolated polynucleotides or nucleic acid molecules (e.g., SEQ ID NO:37, 39, 41, 43, 45, 47, 49, 51, 53, 55, 57, and 59) encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Cancer Treatment

As described above, high CD47 levels have been observed in numerous cancers either at the tumor site or systemically. Such cancers include acute myeloid leukemia (AML), non-Hodgkin's lymphoma (NHL), and solid tumors such as small-cell lung cancer (SCLC), without limitations. It is believed that administration of the presently described antibodies or fragments can be useful for treating or inhibit cancer, and studies in pre-clinical models of cancer suggest that anti-tumor activity of CD47 arises from its ability to potentiate effector cells such as macrophage cells, T cells and NK cells.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient expresses, over-express, or is induced to express CD47.

Cancers that can be suitably treated include bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. Accordingly, the presently disclosed antibodies can be used for treating any one or more such cancers. In some embodiments, the cancer is selected from breast, esophageal, gastrointestinal, lung, hepatic, and ovarian cancers.

Cellular therapies, such as chimeric antigen receptor (CAR) T-cell therapies, are also provided in the present disclosure. A suitable cell can be used, that is put in contact with an anti-CD47 antibody of the present disclosure. Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Fibrosis

Fibrosis is the formation of excess fibrous connective tissue in an organ or tissue in a reparative or reactive process. This can be a reactive, benign, or pathological state. Physiologically, fibrosis acts to deposit connective tissue, which can obliterate the architecture and function of the underlying organ or tissue. It has been shown that anti-CD47 antibodies can reverse lung fibrosis.

In one embodiment, therefore, the present disclosure provides a method of treating fibrosis by administering to a patient having fibrosis an antibody or fragment of the present disclosure. The method is useful for treating various types of fibrosis, such as pulmonary fibrosis, liver fibrosis, heart fibrosis, mediastinal fibrosis, retroperitoneal cavity fibrosis, bone marrow fibrosis, skin fibrosis, scleroderma and systemic sclerosis. In a specific example, the fibrosis is pulmonary fibrosis.

Diagnostic Methods

Over-expression of CD47 is observed in certain tumor samples, and such patients are likely responsive to treatments with the anti-CD47 antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with an CD47 protein potentially present in the sample. Methods such as ELISA can be used, taking advantage of the anti-CD47 antibody, to detect the presence of the CD47 protein in the sample.

Presence of the CD47 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Mouse Monoclonal Antibodies Against Human CD47

Anti-human CD47 mouse monoclonal antibodies were generated using the hybridoma technology.

Antigen: human CD47ECD human Fc protein

Immunization: To generate mouse monoclonal antibodies to human CD47, 4-6 week female Swiss Webster mice were immunized with human CD47ECD human Fc protein at 40 ug/mouse. Day 21 and 35 post first immunization, the immunized mice were boosted with 30 ugs of human CD47ECD human Fc protein each mouse. To select mice producing antibodies that bound human CD47, sera from immunized mice were tested by ELISA. Briefly, microtiter plates were coated with human CD47ECD human Fc protein at 1 µg/ml in PBS, 100 µl/well at 4° C. overnight and blocked with 100 µl/well of 2% BSA for 1 hour at RT. Dilutions of plasma from immunized mice were added to each well and incubated for 1-2 hours at RT. The plates were washed with PBS/Tween and then incubate with anti-mouse IgG antibody conjugated with Horse Radish Peroxidase (HRP) for 1 hour at RT. After washing, the plates were developed with TMB peroxidase substrate and analyzed by spectrophotometer at OD 450 nm. Mice with sufficient titers of anti-CD47 IgG were boosted with 30 ug human CD47huFc protein 3-4 days before fusions.

Hybridoma fusions were done using BTX2001 electro-cell manipulator (Harvard Apparatus) and the standard protocol for hybridoma electro-fusion. Total mouse lymphocytes isolated from both lymph nodes and the spleen were fused with SP2/0 cells (ATCC) and hybridoma were selected using media containing Azaserine (Sigma). Hybridoma supernatants were screened using both the ELISA and FACS assays. Positive wells were further subcloned using the limited dilution method.

Hybridoma clones D8S1, D28S1, D36S4, D41S2, D96S1 and D125S3 were selected for hybridoma sequencing. Briefly, RNAs were extracted from hybridoma cells using Trizol reagents (Invitrogen) and cDNAs were prepared using the PrimeScript™ Reverse Transcriptase). Antibody heavy and light chain V regions were PCR amplified using the cDNAs and the mouse Ig-Primer Set (Novagen, TB326 Rev.B 0503) and sequences were obtained using the standard DNA sequencing techniques.

The amino acid and polynucleotide sequences of the variable regions of the antibodies are provided in Table 1 below.

TABLE 1

Anti-CD47 mAb heavy and light chain variable region sequences.
Antibody CDRs are bold and underlined.

| Name | Sequence | SEQ ID NO: |
|---|---|---|
| D8S1 VH | GAGGTTCAGCTGCAGCAGTCTGTGGCAGAGCTTGTGAGGCCAGGGCCTC<br>AGTCAAGTTGTCCTGCACAGTTTCTGGCTTCAACATTAAAAATACTTATA<br>TATACTGGGTGAAGCAGAGGCCTGAACAGGGTCTGGAGTGGATTGGAAGG<br>ATTGATCCTGCGAATGGTAATACTAAAGATGCCCCGAAGTTCCAGGGCAA<br>GGCCACTATGACTGCAGACACATCCTCCAACACGGCCTACCTACAGCTCA<br>GTAGCCTGACATCTGAGGACACTGCCATCTATTACTGTGCTAGAGGCTAC<br>GGTAGTGGCTTTGCTTACTGGGGCCAAGGGACTCTGGTCACTGTCTCTGC<br>A | 37 |
| D8S1 VH | EVQLQQSVAELVRPGASVKLSCTVSGFNIKNTYIYWVKQRPEQGLEWIGR<br>IDPANGNTKDAPKFQGKATMTADTSSNTAYLQLSSLTSEDTAIYYCARGY<br>GSGFAYWGQGTLVTVSA | 38 |
| D8S1 VL | GATATCCAGATGACACAGACTACATCCTCCCTGTCTGCCTCTCTGGGAGA<br>CAGAGTCACCATCAGTTGCAGGGCCAGTCAGGACATTAGCAATCATTTAA<br>ACTGGTATCAGCAGAAACCAGATGGAATTGTTAAACTCCTGATCTACTAC<br>ACATCAAGATTACACTCAGGAGTCCCATCAAGGTTCAGTGGCAGTGGGTC<br>TGGGACAGATTATTCTCTCACCATTAGCAACCTGGAACAAGAAGATATTG<br>CCACTTACTTTTGCCAACAGGGTAGTACGCTTCCATTCACGTTCGGCTCG<br>GGGACAAAGTTGGAAATAAAA | 39 |

TABLE 1-continued

Anti-CD47 mAb heavy and light chain variable region sequences.
Antibody CDRs are bold and underlined.

| Name | Sequence | SEQ ID NO: |
|---|---|---|
| D8S1 VL | DIQMTQTTSSLSASLGDRVTISCRASQDISNHLNWYQQKPDGIVKLLIYYTSRLHSGVPSRFSGSGSGTDYSLTISNLEQEDIATYFCQQGSTLPFTFGSGTKLEIK | 40 |
| D28S1VH | GAGGTGCAGCTGGTGGAGTCTGGGGGAGACTTAGTGAAGCCTGGAGGGTCCCTGAAACTCTCCTGTGCAGCCTCTGGATTCACTTTCACTAGCTATGGCATGTCTTGGGTTCGCCAGACTCCAGACAAGAGGCTGGAGTGGGTCGCAACCATTAATACTGGTGGTAGTTACACCTACTATCCAGACAGTGTGAAGGGGCGATTCACCATCTCCAGAGACAATGCCAAGAACACCCTGTACCTGCAAATGAGCAGTCTGAAGTCTGAGGACACAGCCATGTATTACTGTGCAAGACATACTATTAAATCTCTTATGGACTACTGGGGTCAAGGAACCTCAGTCACCGTCTCCTCA | 41 |
| D28S1VH | EVQLVESGGDLVKPGGSLKLSCAASGFTFTSYGMSWVRQTPDKRLEWVATINTGGSYTYYPDSVKGRFTISRDNAKNTLYLQMSSLKSEDTAMYYCARHTIKSLMDYWGQGTSVTVSS | 42 |
| D28S1 VL | GAAACAACTGTGACCCAGTCTCCAGCATCCCTGTCCATGGCTATAGGAGAAAAAGTCACCATCAGATGCATAACCAGCACTGATATTGATGATGATATGAACTGGTACCAGCAGAAGCCAGGGGAACCTCCTAAGCTCCTTATTTCAGAAGGCAATACTCTTCGTCCTGGAGTCCCATCCCGATTCTCCAGCAGTGGCTATGGTACAGATTTTGTTTTTATAATTGAAAACATGTTCTCAGAAGATGTTGCAGATTACTACTGTTTGCAAAGTGATAACTTGCCGTATACGTTCGGATCGGGGACCAAGCTGGAAATAAAA | 43 |
| D28S1 VL | ETTVTQSPASLSMAIGEKVTIRCITSTDIDDDMNWYQQKPGEPPKLLISEGNTLRPGVPSRFSSSGYGTDFVFIIENMFSEDVADYYCLQSDNLPYTFGSGTKLEIK | 44 |
| D36S4VH | TTGGTGCAACCTGGAGGATCCATGAAACTCTCCTGTGTTGCCTCTGGATTCACTTTCAGTAGATACTGGATGAACTGGGTCCGCCAGTCTCCAGACAAGGGGCTTGAGTGGGTTGCTCAAATTAGATTGAAATCTGATAATTATGAAACACATTATGCGGAGTCTGTGAAAGGGAGGTTCACCATCTCAAGAGATGATTCCAAAAGTAGTGTCTACCTGCAAATGAACAACTTAAGGGCTGAAGACACTGGAATTTATTATTGTATAGAAGAGGGGGGTTACTACGTCCCGTTTGCTTACTGGGGCCAAGGGACTCTGGTCACTGTCTCTGCA | 45 |
| D36S4VH | EVKLEESGGGLVQPGGSMKLSCVASGFTFSRYWMNWVRQSPDKGLEWVAQIRLKSDNYETHYAESVKGRFTISRDDSKSSVYLQMNNLRAEDTGIYYCIEEGGYYVPFAYWGQGTLVTVSA | 46 |
| D36S4 VL | GACATTGTCGTGTCACAGTCTCCATCCTCCCTGGCTGTGTCAGCAGGAGAAGGTCACTATGAGCTGCAAATCCAGTCAGAGTCTGTTCAAAAGTAGAACCCGAAAGAACTACTTGGCTTGGTACCAGCAGAGACCAGGGCAGTCTCCTAAACTGCTGATCTACTGGGCATCCATTAGGGAATCTGGGGTCCCTGATCGCTTCACAGGCAGTGGATCTGGGACAGAATTCACTCTCACCATCAGCAGTGTGCAGGCTGAAGACCTGGCAGTTTATTACTGCAAGCAATCTTATTATCTACTCACGTTCGGTGCTGGGACCAAACTGGAGCTGAAA | 47 |
| D36S4 VL | DIVVSQSPSSLAVSAGEKVTMSCKSSQSLFKSRTRKNYLAWYQQRPGQSPKLLIYWASIRESGVPDRFTGSGSGTEFTLTISSVQAEDLAVYYCKQSYYLLTFGAGTKLELK | 48 |
| D41S2VH | GAGGTTCAGCTGCAGCAGTCTGTGGCAGAGCTTGTGAGGCCAGGGGCCTCAGTCAAGTTGTCCTGCACACCTTCTGGCTTCAACATTAAAAACACTTATATATACTGGGTGAGACAGAGGCCTGAACAGGGTCTGGAGTGGATTGGAAGGATTGATCCTGCGAATGGTAATACTAAAGATGCCCCGAAGTTCAGGGCAAGGCCACTATGACTGCAGACACATCCTCCAACACAGCCTACCTACAGCTCAGCAGCCTGACATCTGAGGACACTGCCATCTATTACTGTGCTAGAGGCTACGGTAGTGGCTTTGCTTACTGGGGCCAAGGGACTCTGGTCACTGTCTCTGCA | 49 |
| D41S2VH | EVQLQQSVAELVRPGASVKLSCTPSGFNIKNTYIYWVRQRPEQGLEWIGRIDPANGNTKDAPKFQGKATMTADTSSNTAYLQLSSLTSEDTAIYYCARGYGSGFAYWGQGTLVTVSA | 50 |
| D41S2 VL | GATATCCAGATGACACAGACTACATCCTCCCTGTCTGCCTCTCTGGGAGACAGAGTCACCATCAGTTGCAGGGCCAGTCAGGACATTAGCAATCATTTAAACTGGTATCAGCAGAAACCAGATGGAACTGTTAAACTCCTGATCTACTACACATCAAGATTACACTCAGGAGTCCCATCAAGGTTCAGTGGCAGTGGGTCTGGGACAGATTATTCTCTCACCATTAGCAACCTGGAACAAGAAGATATTGCCACTTACTTTTGCCAACAGGGTAGTACGCTTCCATTCACGTTCGGCTCGGGGACAAAGTTGGAAATAAAA | 51 |

TABLE 1-continued

Anti-CD47 mAb heavy and light chain variable region sequences.
Antibody CDRs are bold and underlined.

| Name | Sequence | SEQ ID NO: |
|---|---|---|
| D41S2 VL | DIQMTQTTSSLSASLGDRVTISCRASQDISNHLNWYQQKPDGTVKLLIYY TSRLHSGVPSRFSGSGSGTDYSLTISNLEQEDIATYFCQQGSTLPFTFGS GTKLEIK | 52 |
| D96S1VH | GAGGTTCAGCTGCAGCAGTCTGGGGCAGAGCTTGTGAAGCCAGGGGCCTC AGTCAAGTTGTCCTGCACAGCTTCTGGCTTCAACATTAAAGACACCTATA TACACTGGGTGAAGCAGAGGCCTGAACAGGGCCTGGAATGGATTGGAAGG ATTGATCCTGCGAATGGTAATATTAAATCTGACCCGAAGTTCCAGGGCAA GGCCACTGTAACAGCAGACACATCCTCCAACACAGCCTACCTGCAGCTCA GCAGCCTGACATCTGAGGACACTGCCGTCTATTACTGTGCTAGGTCTTAC GGTAGTAGTTTTGCTTCCTGGGGCCAGGGGACTCTGGTCACTGTCTCTCC A | 53 |
| D96S1VH | EVQLQQSGAELVKPGASVKLSCTASGFNIKDTYIHWVKQRPEQGLEWIGR IDPANGNIKSDPKFQGKATVTADTSSNTAYLQLSSLTSEDTAVYYCARSY GSSFASWGQGTLVTVSP | 54 |
| D96S1 VL | GATATCCAGATGACACAGACTACATCCTCCCTGTCTGCCTCTCTGGGAGA CAGAGTCACCATCAGTTGCAGGGCCAGTCAGGACATTAGCAATCATTTAA ACTGGTATCAGCAGAAACCAGATGGAGCTGTTAAACTCCTGATCTACTAC ACATCAAGATTACACTCAGGAGTCCCATCAAGGTTCAGTGGCAGTGGGTC TGGGACAGATTATTCTCTCACCATTAGCAACCTGGAACAAGAAGATATTG CCACTTACTTTTGCCAACAGGGTAGTACGTTTCCGTACACGTTCGGAGGG GGGACCAAGCTGGAAATAAAA | 55 |
| D96S1 VL | DIQMTQTTSSLSASLGDRVTISCRASQDISNHLNWYQQKPDGAVKLLIYY TSRLHSGVPSRFSGSGSGTDYSLTISNLEQEDIATYFCQQGSTFPYTFGG GTKLEIK | 56 |
| D125S3VH | GAGGTGCAGCTGGTGGAGTCTGGGGGAGACCTAGTGAAACCTGGAGGGTC CCTGAACCTCTCCTGTGCAGCCTCTGGATTCACTTTCAGTGACTATGGCA TGTCTTGGGTTCGCCAGACTCCAGACATGAGGCTGGAGTGGGTCGCAACC ATTAGTAAGTATGGTACTTATACGTCCTATCCGGACAGTGTAAAGGGGCG ATTCACCATCTCCAGAAGCAATGCCAAGAATACCCTATACCTACAAATGA GCAGTCTGAAGTCTGCGGACACTGCCCTATATTACTGTCAAGACGTTTC TTTGGTAACTACAACTACTGGTACTTCGATGTGTGGGCGCAGGGACCAC GGTCACCGTCTCCTCA | 57 |
| D125S3VH | EVQLVESGGDLVKPGGSLNLSCAASGFTFSDYGMSWVRQTPDMRLEWVAT ISKYGTYTSYPDSVKGRFTISRSNAKNTLYLQMSSLKSADTALYYCARRF FGNYNYWYFDVWGAGTTVTVSS | 58 |
| D125S3VL | GACATTGTGCTGACCCAATCTCCAGCTTCTTTGGCTGTGTCTCTAGGCCA GAGGGCCACCTTCTCCTGCAGAGCCAGCGAAAGTGTTGATGAGTTTGGCA TTAGTTATATACACTGGTACAAGAAGAGCCCAGGACAGCCACCCAAACTC CTCATCTATCGTGCATCCACCCTAGAATCTGGGATCTCTGCCAGGTTCAG TGGCAGTGGGTCTGGGACAGACTTCACCCTCACCATTAATCCTGTGGAGA CTGATGATGTTGCAACCTATTACTGTCAGCAAAGTAATCAGGATCCTCTC ACGTTCGGTGCTGGGACCAAGCTGGAACTGAAA | 59 |
| D125S3VL | DIVLTQSPASLAVSLGQRATFSCRASESVDEFGISYIHWYKKSPGQPPKL LIYRASTLESGISARFSGSGSGTDFTLTINPVETDDVATYYCQQSNQDPL TFGAGTKLELK | 60 |

Example 2: Anti-CD47 Mouse Monoclonal Antibody's Binding Activity for Human CD47

To evaluate the binding activity of anti-CD47 mouse hybridoma antibodies, the hybridoma supernatants from 12 clones were analyzed by FACS analysis using CHO cells expressing human CD47. Briefly, 96 well microtiter plates were seeded with human CD47/CHO cells at 200,000 cells/well. 50 µl of anti-CD47 hybridoma supernatants were added into each well at neat or various dilutions. The cells were resuspended well with the antibody supernatants and incubated at 4° C. for 15 min. The cells were then washed with PBS three times, followed by incubation with PE-labeled anti-mouse Fc gamma specific antibody (Jackson Immuno-Research) at 4° C. for 15 min. The cells were washed again with PBS three times and analyzed using an FACS Caliber instrument (Becton-Dickinson). As shown in FIG. 1, 11 of the 12 anti-human CD47 antibodies had high binding activities to CHO cells expressing native human CD47 receptor. Only one antibody, D97S5, had low activity binding to CHO/CD47 cells.

Figure 2:
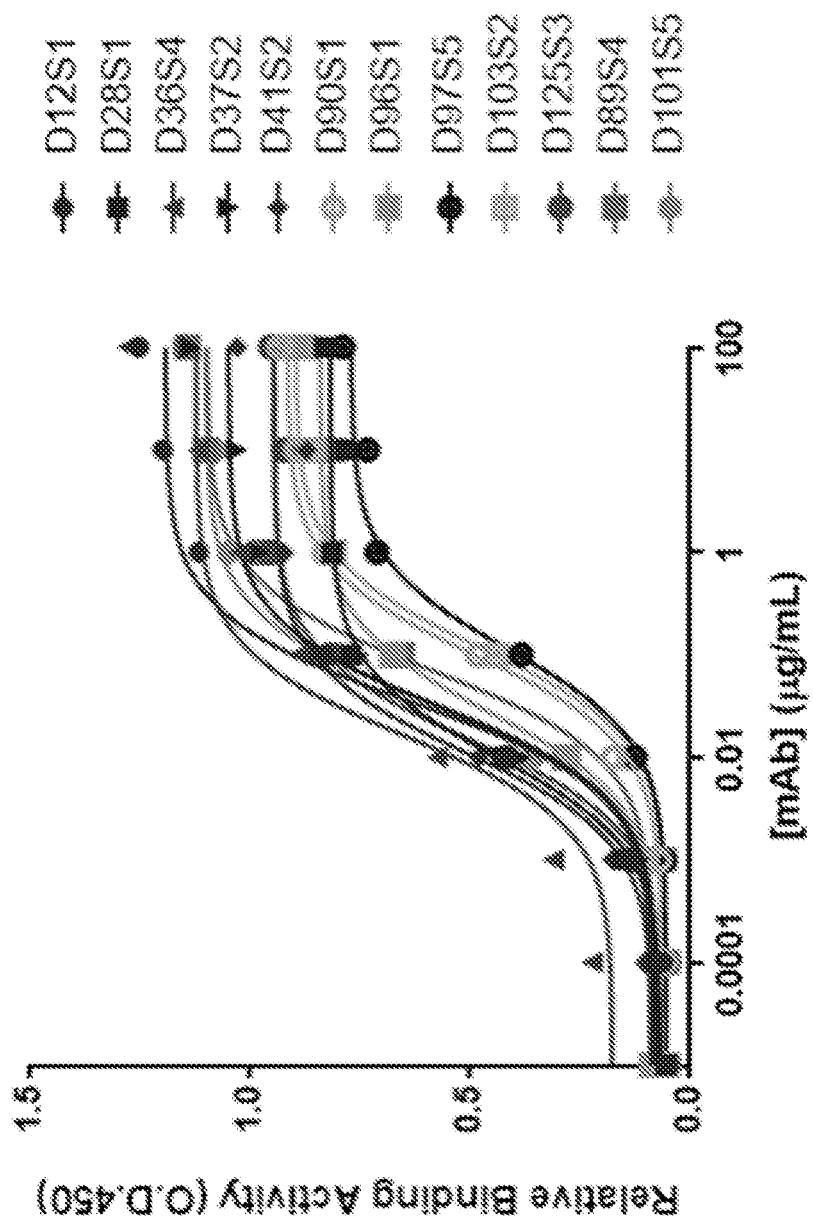
FIG. 2 shows the anti-human CD47 antibody binding to plate-bound human CD47. 96 well ELISA plates were coated with human CD47ECD huFc protein at 1 ug/ml in PBS.

The binding affinities of anti-human CD47 antibody to human CD47 were evaluated in ELISA assays. Briefly, 96 well microtiter plates were coated with human CD47ECD huFc protein at 1 µg/ml in PBS, 100 µl/well at 4° C. overnight and then blocked with 100 µl/well of 2% BSA at RT for 1 hour. Ten-fold dilutions of purified mouse hybridoma antibodies starting from 100 µg/ml were added to each well and incubated for 1-2 hours at RT. The plates were washed with PBS/Tween and then incubated with goat-anti-mouse IgG antibody conjugated with Horse Radish Peroxidase (HRP) for 1 hour at RT. After washing, the plates were developed with TMB substrate and analyzed by spectrophotometer at OD 450 nm. As shown in FIG. 2, all 12 antibodies can bind to human CD47 with high activity ($EC_{50}$=10-50 ng/ml).

Figure 3A:
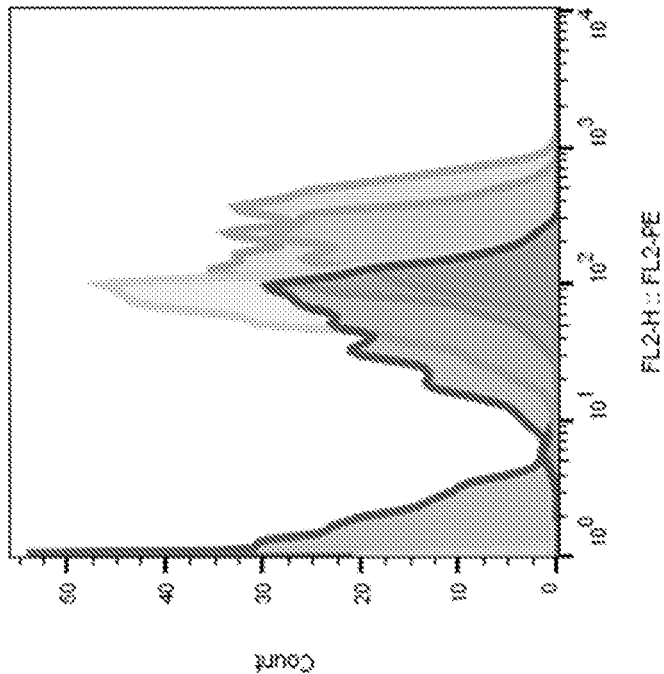
FIGS. 3a and 3b show binding of anti-CD47 antibodies to breast cancer cell line MDA-MB 231.
Figure 3B:
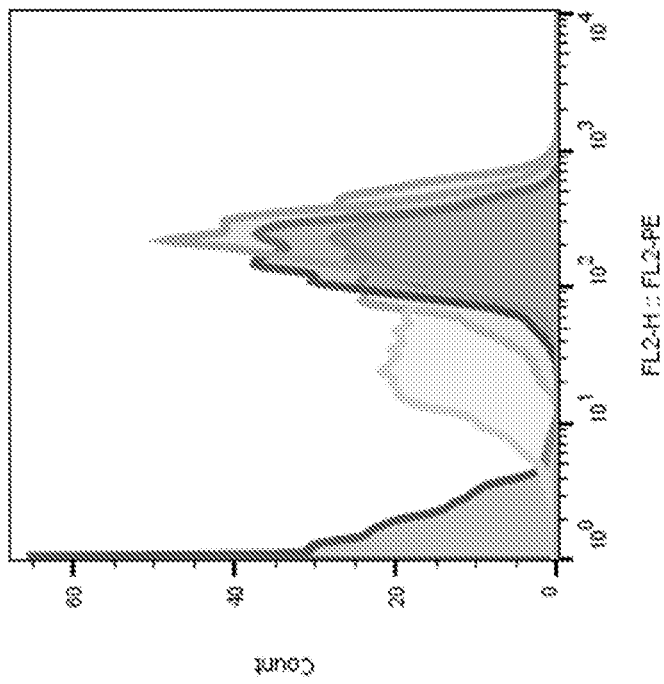

FACS assay was also used to evaluate the binding of anti-CD47 antibodies to breast cancer cell line MDA-MB 231. As shown in FIGS. 3a and 3b, all nine antibodies tested bind to MDA-MB 231 cells with good affinities.

Figure 5A:
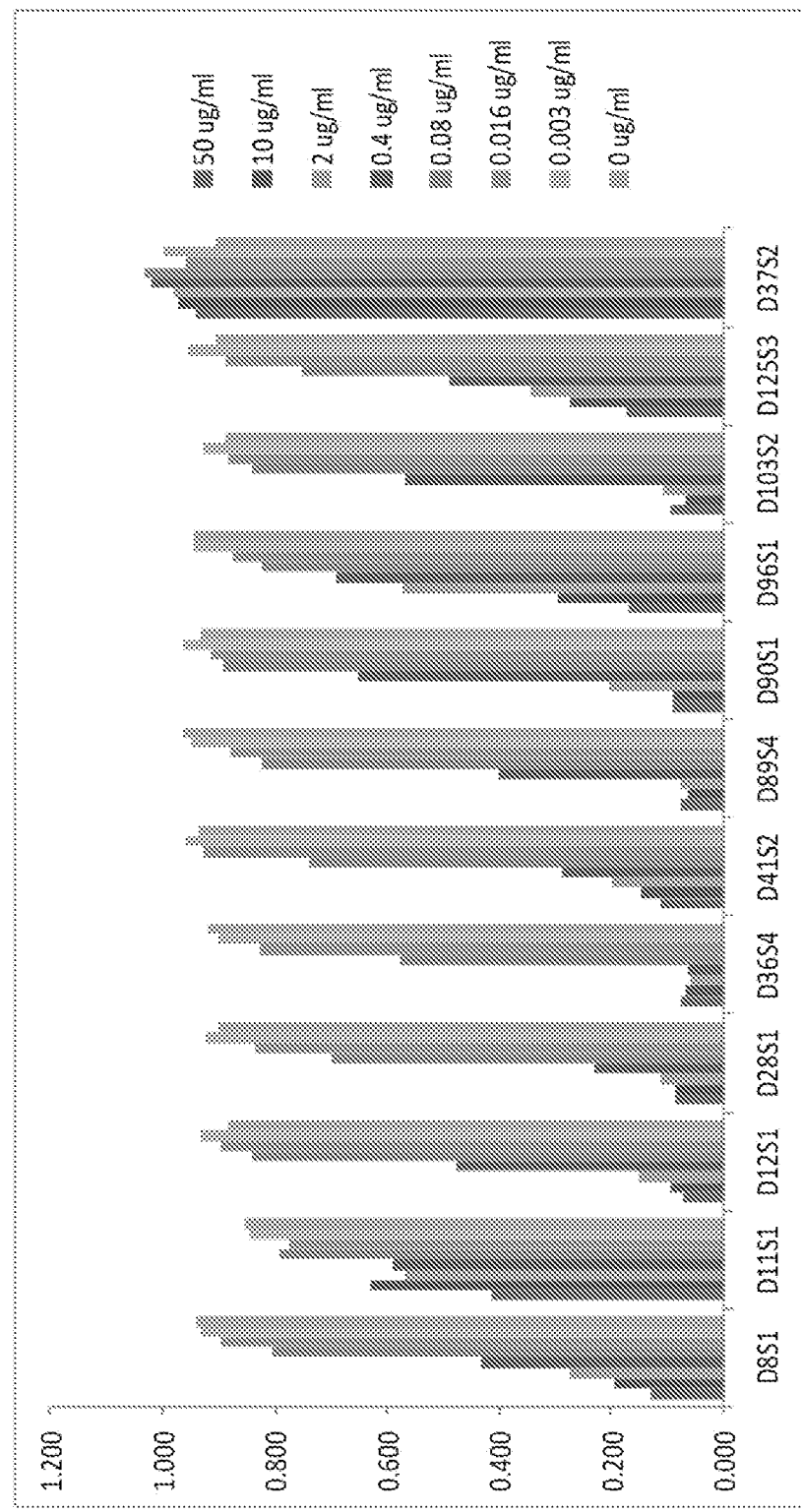
FIGS. 5a and 5b show that anti-Human CD47 blocked SIRPα binding to plate bound human CD47. a) ELISA plates were coated with 1 ug/ml human CD47 ECD HF tagged protein and soluble human SIRPαECD huFc were added at 1 ug/ml. b) IC50 calculations of the ELISA results.
Figure 5B:
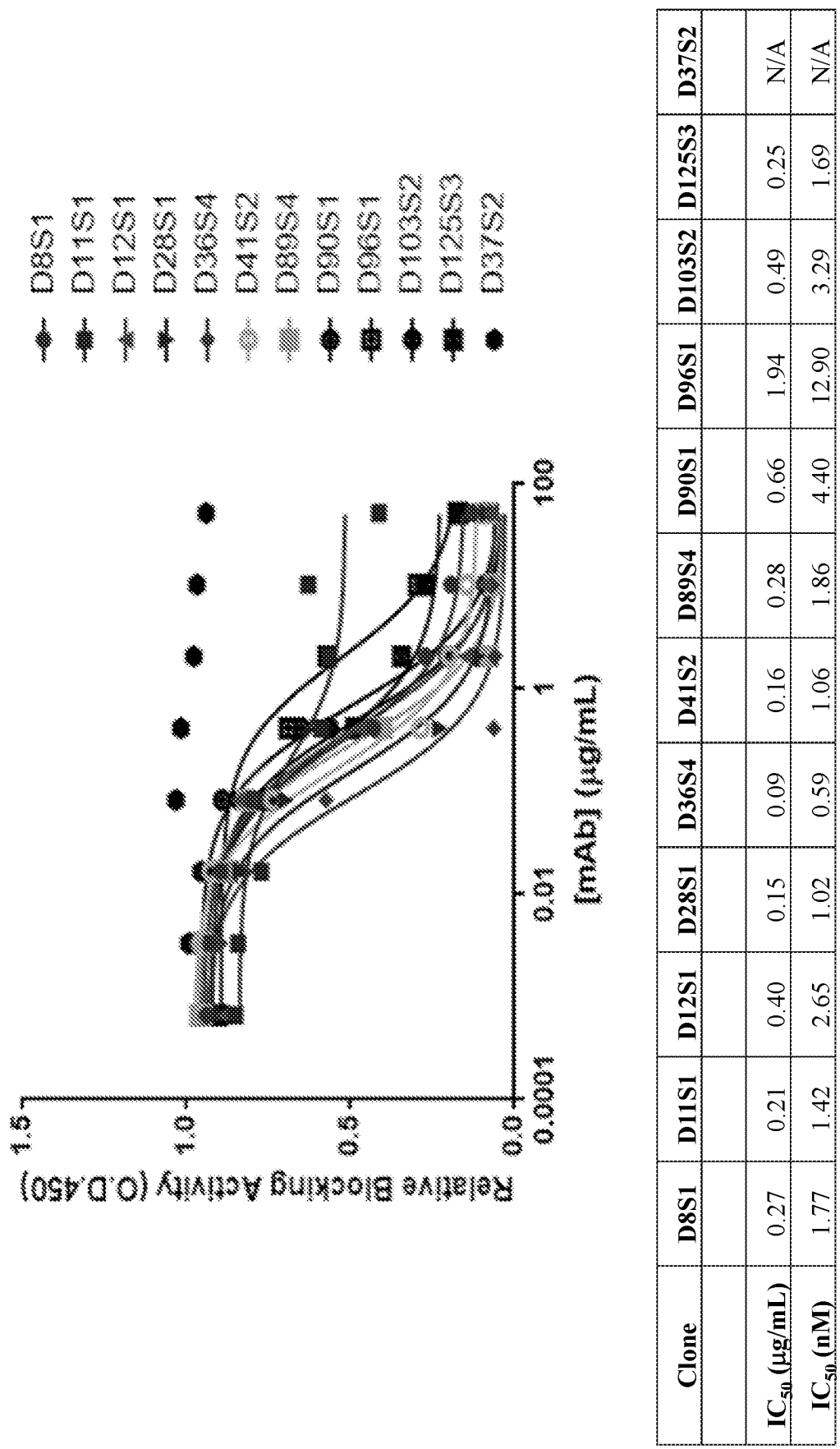

Example 3: Anti-Human CD47 Mouse mAbs Blocked Human CD47 Binding to its Ligand SIRPalpha Ligand Blocking Assay Using Recombinant Human CD47ECD-his Protein To evaluate the blocking ability of anti-human CD47 mouse mAb on recombinant human CD47 binding to its ligand SIRPα, an ELISA based ligand blocking assay was employed. Briefly, microtiter plates were coated with human CD47ECD His tagged protein at 1 μg/ml in PBS, 100 μl/well at 4° C. overnight, then blocked with 100 μl/well of 2% BSA. 50 μl of human SIRPα huFc protein (1 ug/ml) and 5-fold dilutions of anti-human CD47 antibodies starting from 50 μg/ml at 50 μl were added to each well and incubated for 1 hour at 37° C. The plates were washed with PBS/Tween and then incubated with anti-human IgG-HRP for 1 hour at 37° C. After washing, the plates were developed with TMB substrate and analyzed by spectrophotometer at OD 450 nm. As shown in FIG. 5a, most of the anti-human CD47 antibodies can efficiently inhibit the binding of human SIRPα to human CD47. The IC50 for D28S1 is 1 nM while the IC50 for D36S4 is 0.59 nM (FIG. 5b).

Ligand Blocking Assay Using Mammalian Cell Expressed Human CD47

Figure 4:
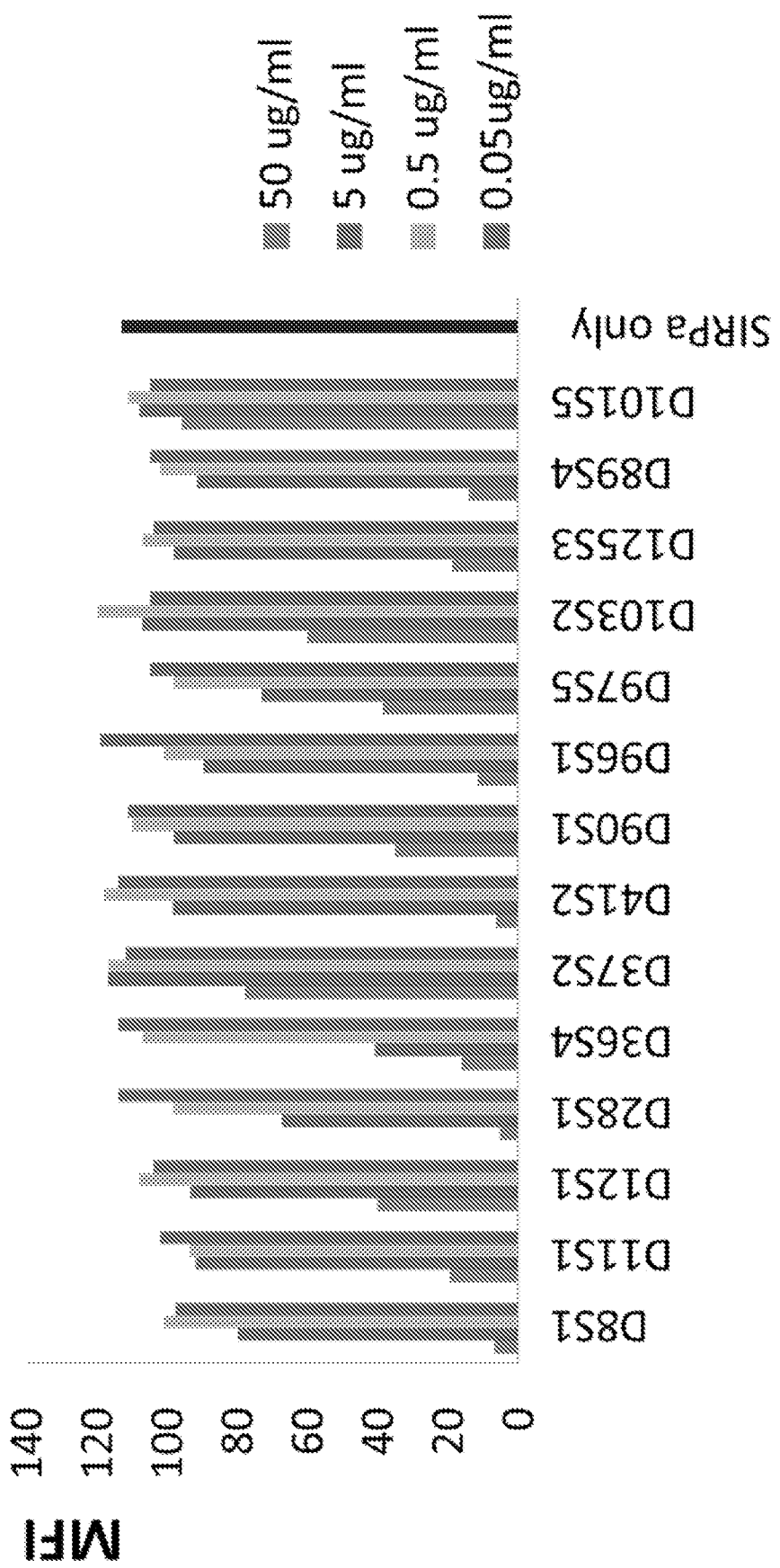
FIG. 4 shows blocking of SIRPα binding to CD47 on CHO cell surface. 0.2 μg/ml of SIRPα huFc protein was used in the assay.

To evaluate the blocking effect of anti-human CD47 mouse mAbs to human full length CD47 expressed on CHO cells, the FACS-based ligand blocking assay was used. Briefly, CD47-CHO cells were first incubated with 5 fold serially diluted mouse mAbs starting at 50 μg/ml on ice for 30 min. After washing by FACS buffer once (PBS with 2% FBS), 0.2 μg/ml of human SIRPα huFc protein was added to the cells and incubated on ice for another 15 min. The cells were then washed 3 times with the FACS buffer. PE-labeled anti-human Fc gamma specific antibody (Jackson Immuno-Research) was added to the cells and the cells were incubated at 4° C. for 15 min. The cells were again washed three times in FACS buffer and the mean florescence intensities (MFI) of PE were evaluated by FACS Caliber. As shown in FIG. 4, most of the 14 evaluated anti-human CD47 hybridoma antibodies can efficiently inhibit the binding of SIRPα onto CD47 expressed CHO cells. Among them, D28S1, D36S4, D96S1 were the most effective ones.

Example 4: Anti-Human CD47 Mouse/Human Chimeric Antibodies Blocked Human CD47 Binding to its Ligand SIRPalpha To evaluate the blocking effects of anti-human CD47 mouse/human chimeric antibodies on human CD47 binding to its ligand SIRPα, anti-human CD47 mouse/human chimeric antibodies were produced from HEK293 cells. Briefly, mouse antibody heavy and light chain V regions were cloned into transient expression vectors containing human antibody heavy chain IgG1 and light chain constant regions. The resulting antibody heavy and light chain expression constructs were used to transfect HEK293 cells. The culture supernatants were harvested and loaded onto protein A Sepharose columns (GE Healthcare). The columns were washed and antibodies were then eluted with eluting buffer (0.1 M glycine buffer, pH 3.0). Collected fractions were neutralized with 1 M Tris-HCl, pH 8.0, pooled together and then dialyzed against PBS. Purity of the antibodies was analyzed by sodium dodecyl sulfate polyacrylamide gel electrophoresis (SDS-PAGE) under both reducing and non-reducing conditions. Protein bands were visualized by Coomassie brilliant blue staining.

Figure 6A:
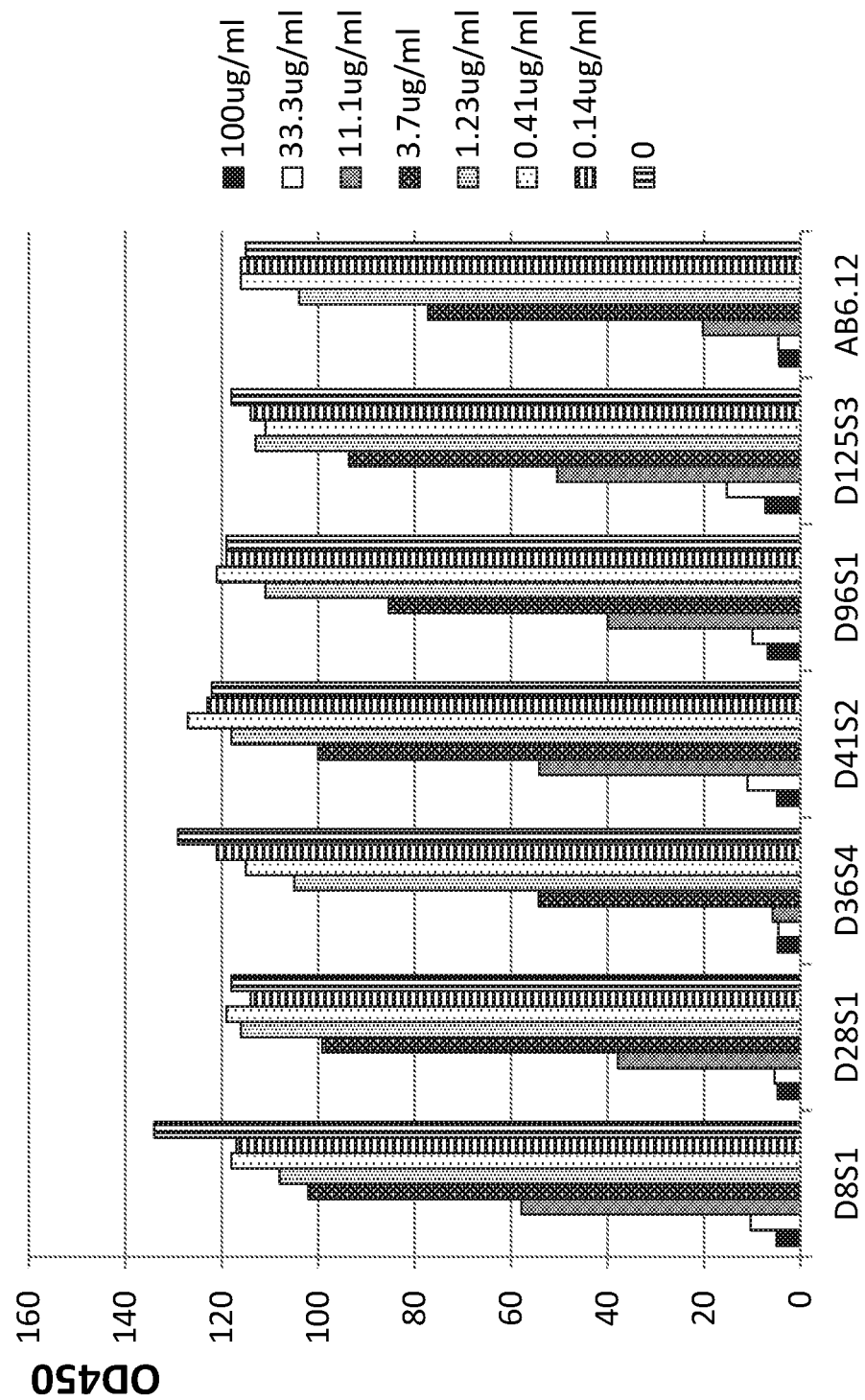
FIGS. 6a and 6b show the blocking SIRPα binding to CD47 expressed on CHO cells by anti-CD47 chimeric antibodies. a) SIRPα FITC used at 4 ug/ml. b) IC50 calculations of the assay results.
Figure 6B:
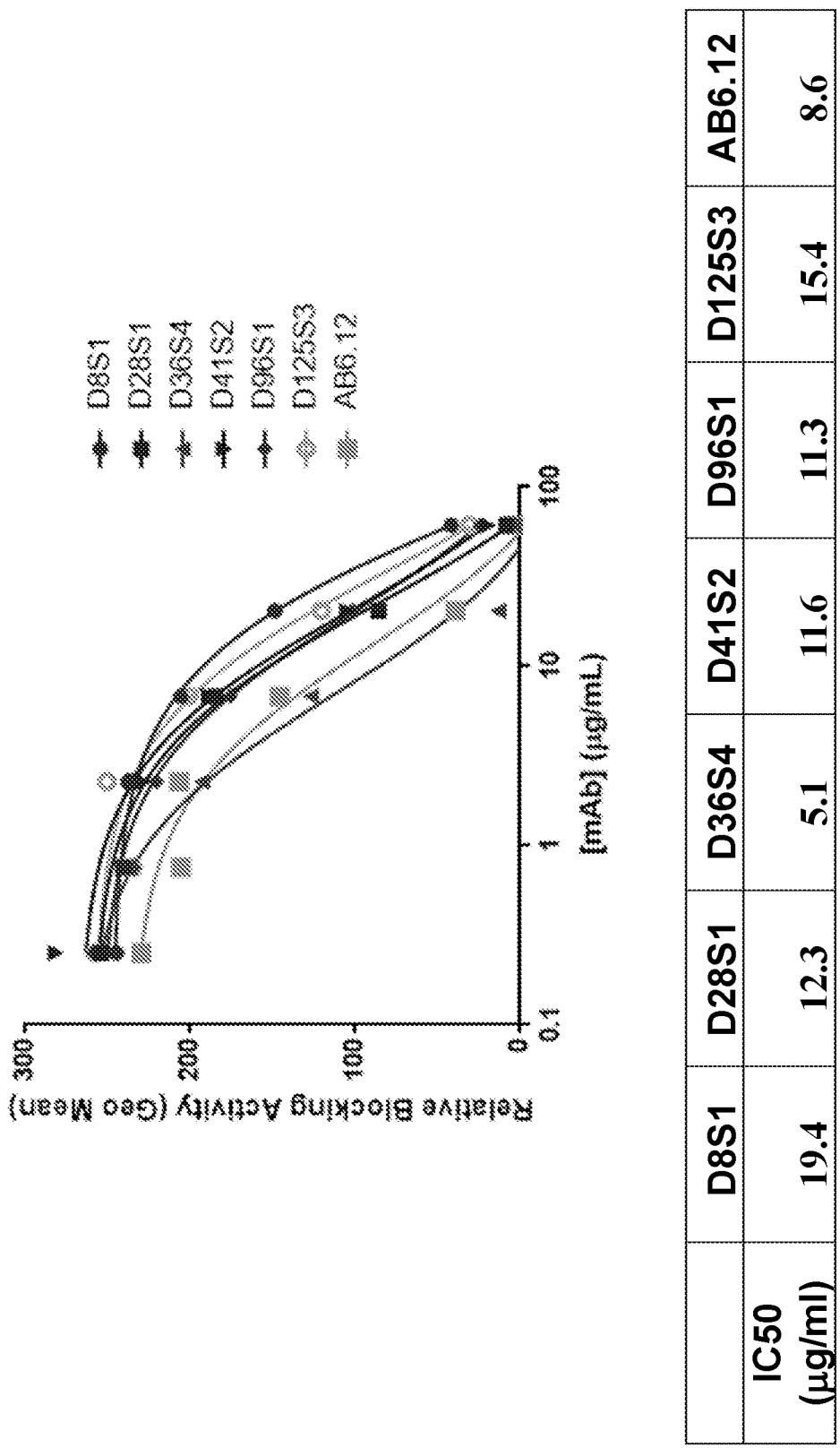

To evaluate the blocking effect of anti-human CD47 mouse/human chimeric antibodies to human full length CD47 expressed on CHO cells, the FACS-based ligand blocking assay was used. CD47-CHO cells were first incubated with 3 fold serially diluted mouse/human chimeric mAbs starting at 100 μg/ml on ice for 30 min. After washing by FACS buffer once (PBS with 2% FBS), 4 μg/ml of FITC labeled human SIRPα huFc protein was added to the cells and incubated on ice for another 15 min. The cells were then washed 3 times with the FACS buffer and the mean florescence intensities (MFI) of FITC were evaluated by FACS Caliber. As shown in FIG. 6a, all six anti-human CD47 chimeric antibodies can efficiently inhibit the binding of SIRPα onto CD47 expressed CHO cells. The IC50s were between 5-20 ug/ml (FIG. 6b). AB6.12 is a humanized version of anti-CD47 antibody 2A1 from Celgene and was used as a reference antibody in the assay.

Example 5: The Binding Affinities of Anti-Human CD47 Mouse/Human Chimeric Antibodies The binding affinities of anti-human CD47 mouse/human chimeric antibodies to human CD47 protein were determined with BIACORE™ using a capture method. The anti-human CD47 mouse/human chimeric antibodies were captured using anti-human Fc antibody coated on a CM5 chip. Serial dilutions of human CD47ECD mouse Fc protein starting from 400 nM were injected over captured antibody for 1 mins at a flow rate of 300/ml. Alternatively, serial dilutions of human CD47ECD His tagged protein starting from 800 nM were injected over captured antibody for 1 min at a flow rate of 30 μl/ml. The antigens were allowed to dissociate for 900s. All the experiments were carried out on a Biacore 3000. Data analysis was carried out using Biacore 3000 evaluation software. The results are shown in Tables 2 and 3 below.

TABLE 2

Binding affinities of anti-human CD47 mAbs to bivalent CD47ECD muFc protein

| Antibody | Antigen | Kon (1/Ms) | Koff (1/s) | KD (M) | Affinity (nM) |
|---|---|---|---|---|---|
| D8S1 | HuCD47ECD muFc | 1.61E+05 | 4.77E−05 | 2.95E−10 | 0.295 |
| D28S1 | HuCD47ECD muFc | 2.99E+05 | 4.13E−04 | 1.38E−09 | 1.38 |
| D36S4 | HuCD47ECD muFc | 6.05E+05 | 1.18E−05 | 1.94E−11 | 0.0194 |
| D41S2 | HuCD47ECD muFc | 1.47E+05 | 3.34E−05 | 2.28E−10 | 0.228 |
| D96S1 | HuCD47ECD muFc | 2.57E+05 | 1.45E−05 | 5.62E−10 | 0.562 |

TABLE 2-continued

Binding affinities of anti-human CD47 mAbs to bivalent CD47ECD muFc protein

| Antibody | Antigen | Kon (1/Ms) | Koff (1/s) | KD (M) | Affinity (nM) |
|---|---|---|---|---|---|
| D125S3 | HuCD47ECD muFc | 2.23E+05 | 7.72E−05 | 3.46E−10 | 0.346 |
| AB6.12 | HuCD47ECD muFc | 4.69E+05 | 2.25E−05 | 4.79E−11 | 0.0479 |

TABLE 3

Binding affinities of anti-human CD47 mAbs to monovalent CD47ECD His tagged protein

| Antibody | Antigen | Kon (1/Ms) | Koff (1/s) | KD (M) | Affinity (nM) |
|---|---|---|---|---|---|
| D8S1 | HuCD47ECD 8xHis | 1.50E+05 | 4.90E−04 | 3.28E−09 | 3.28 |
| D28S1 | HuCD47ECD 8xHis | Low | High | no binding | no binding |
| D36S4 | HuCD47ECD 8xHis | 3.37E+05 | 2.36E−04 | 7.02E−10 | 0.702 |
| D41S2 | HuCD47ECD 8xHis | 1.45E+05 | 7.56E−04 | 5.20E−09 | 5.2 |
| D96S1 | HuCD47ECD 8xHis | 8.09E+04 | 2.53E−04 | 3.13E−09 | 3.13 |
| D125S3 | HuCD47ECD 8xHis | 1.63E+05 | 5.11E−04 | 3.62E−09 | 3.62 |
| AB6.12 | HuCD47ECD 8xHis | 8.81E+05 | 7.03E−04 | 7.98E−10 | 0.798 |

Example 6: Cross-Reactivity of Anti-Human CD47 Antibody Binding to Cynomolgus Monkey and Mouse CD47

Figure 7:
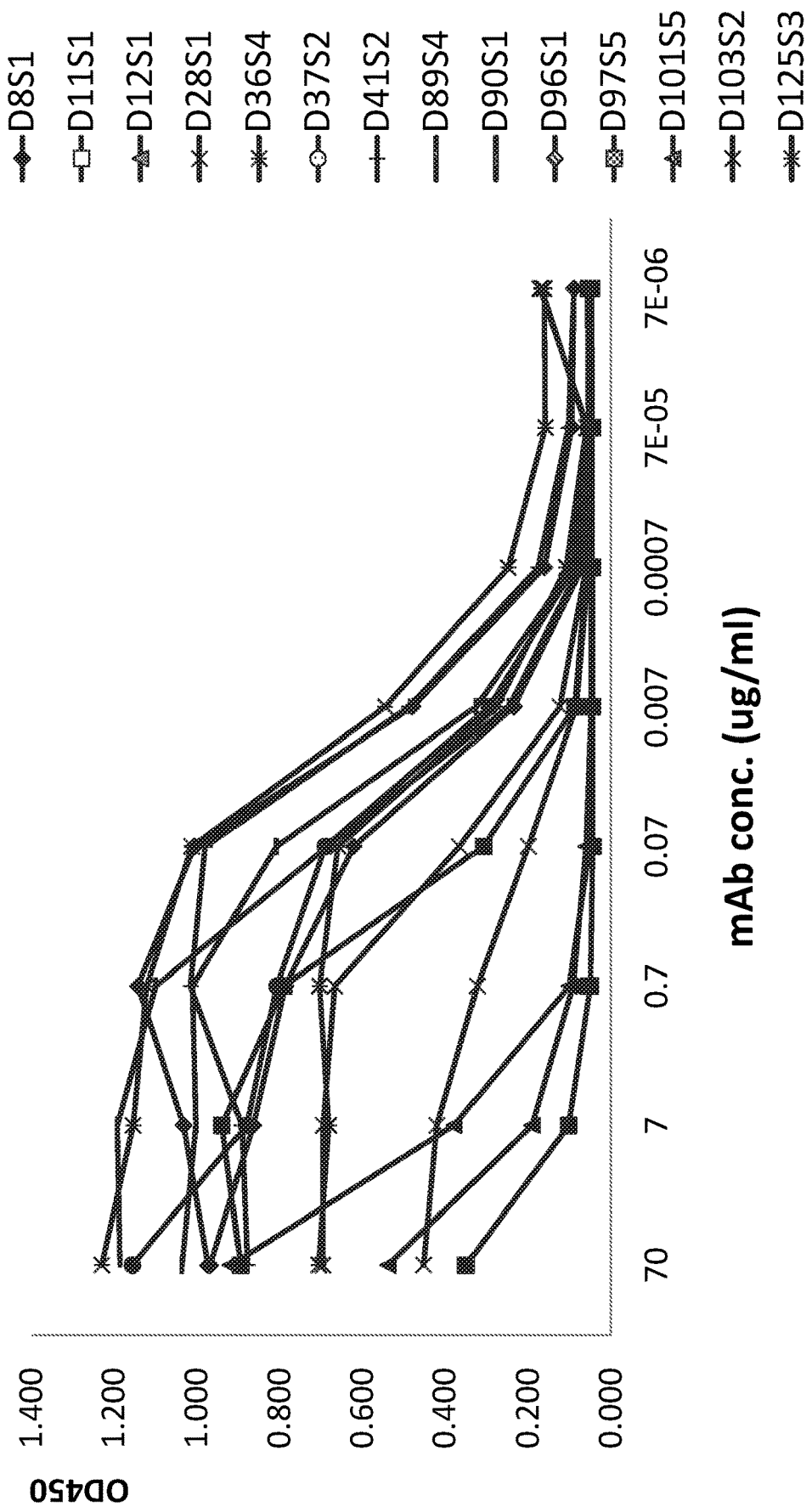
FIG. 7 shows the cross-reactivity of anti-human CD47 to cynomolgus monkey CD47.
Figure 8:
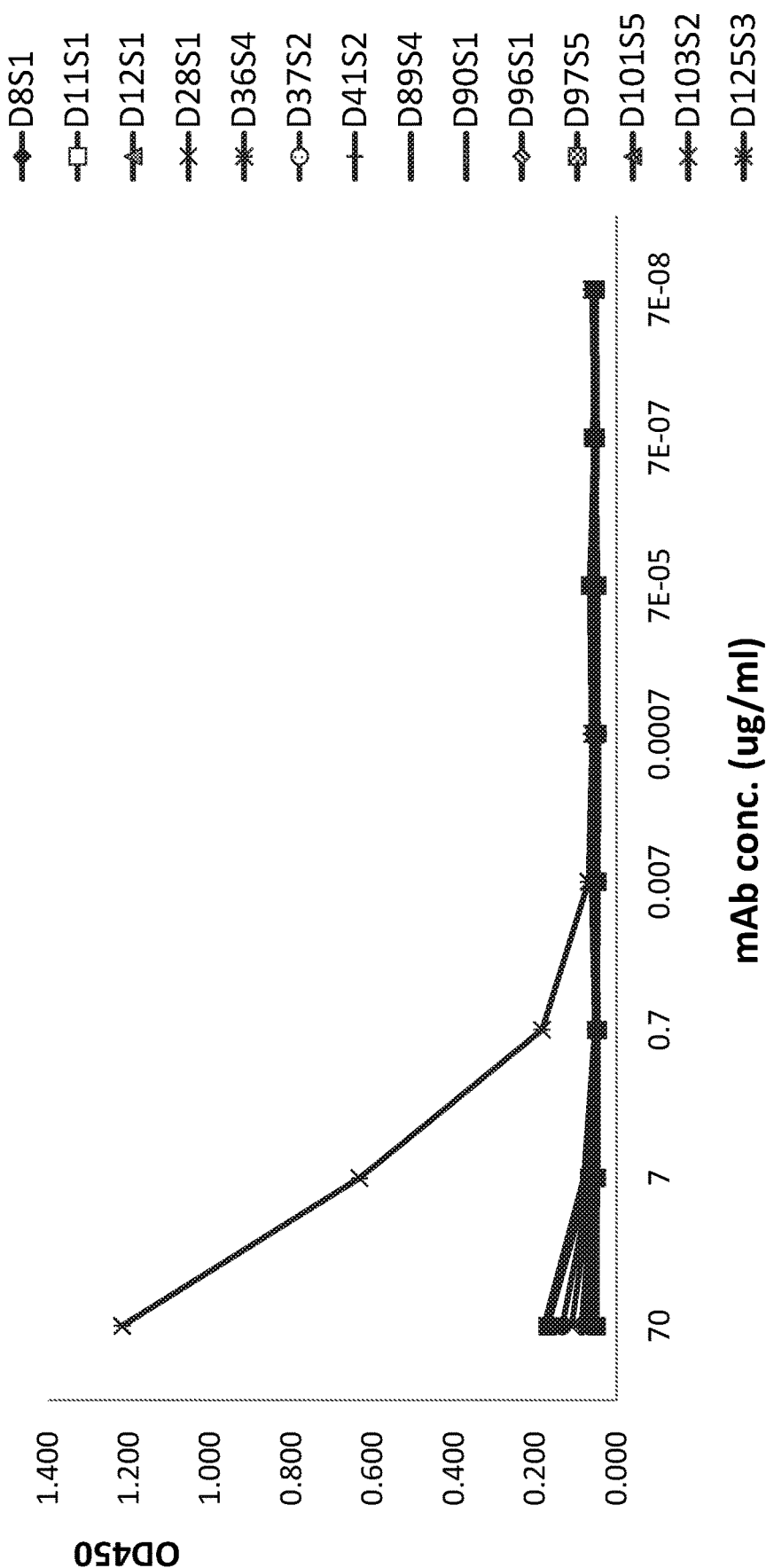
FIG. 8 shows the cross-reactivity of anti-human CD47 to mouse CD47.

To evaluate the binding cross-reactivity of anti-human CD47 antibodies to cynomolgus and mouse CD47, an ELISA based binding assay was used. Briefly, microtiter plates were coated with His tagged cynomolgus monkey CD47 or His tagged mouse CD47 protein (purchase from Acro Biosystem). Both proteins were coated at 2 µg/ml in PBS, 100 µl/well at 4° C. overnight. The plates were then blocked with 100 µl/well of 2% BSA. Ten-fold dilutions of mouse anti-human CD47 hybridoma antibodies were added to each well starting at 70 ug/ml and incubated for 1-2 hours at RT. The plates were washed with PBS/Tween and then incubate with goat-anti-mouse IgG antibody conjugated with Horse Radish Peroxidase (HRP) for 1 hour at RT. After washing, the plates were developed with TMB substrate and analyzed by spectrophotometer at OD 450 nm. As shown in FIG. 7, all antibodies tested show various degrees of cross reactivity to cynomolgus CD47. However, most of the antibodies did not bind to mouse CD47, as shown in FIG. 8. Only D36S4 had a weak binding to mouse CD47.

Example 7: Humanization of Mouse Anti-Human CD47 Antibody D28S1

The mAb D28S1 variable region genes were employed to create a humanized MAb. In the first step of this process, the amino acid sequences of the VH and VK of MAb D28S1 were compared against the available database of human Ig gene sequences to find the overall best-matching human germline Ig gene sequences. For the light chain, the closest human match was the kV5-2/Jk2 gene, and for the heavy chain the closest human match was the V3-21/JH6gene.

Humanized variable domain sequences were then designed where the CDR1 (SEQ ID NO. 1), 2 (EGN) and 3 (SEQ ID NO.3) of the D28S1 light chain were grafted onto framework sequences of the kV5-2/Jk2 gene, and the CDR1 (SEQ ID NO.4), 2 (SEQ ID NO.5), and 3 (SEQ ID NO.6) sequences of the D28S1 heavy chain were grafted onto framework sequences of the VH3-21/JH6. A 3D model was then generated to determine if there were any framework positions where replacing the mouse amino acid to the human amino acid could affect binding and/or CDR conformation. In the case of the light chain, 20T, 22R, 46L, 47L, 49S and 58V (Kabat numbering, see Table 4) in framework were identified. In the case of the heavy chain, 30T, 44R and 49A in the framework were involved in back-mutations.

TABLE 4

Humanization Design for D28S1

| Construct | Mutation |
|---|---|
| VH Design: VH3-21/JH6 | |
| D28S1 VH | Chimera |
| HuD28S1 VH1 | CDR-grafted |
| HuD28S1 VH2 | S30T, S49A |
| HuD28S1 VH3 | G44R |
| VK Design: kV5-2/Jk2 | |
| D28S1 VL | Chimera |
| HuD28S1 VL1 | CDR-grafted |
| HuD28S1 VL2 | F46L |
| HuD28S1 VL3 | F46L, I58V |
| HuD28S1 VL4 | F46L, I47L |
| HuD28S1 VL5 | F46L, I47L, Q49S |
| HuD28S1 VL6 | N20T, S22R, F46L |

TABLE 5

| Name | Sequence | SEQ ID NO: |
|---|---|---|
| D28S1 VH | EVQLVESGGDLVKPGGSLKLSCAASGFTFTSYGMSWVRQTPDKRLEWVAT INTGGSYTYYPDSVKGRFTISRDNAKNTLYLQMSSLKSEDTAMYYCARHT IKSLMDYWGQGTSVTVSS | 42 |
| HuD28S1 VH1 | EVQLVESGGGLVKPGGSLRLSCAASGFTFSSYGMSWVRQAPGKGLEWVST INTGGSYTYYPDSVKGRFTISRDNAKNSLYLQMNSLRAEDTAVYYCARHT IKSLMDYWGQGTTVTVSS | 61 |
| HuD28S1 VH2 | EVQLVESGGGLVKPGGSLRLSCAASGFTFTSYGMSWVRQAPGKGLEWVAT INTGGSYTYYPDSVKGRFTISRDNAKNSLYLQMNSLRAEDTAVYYCARHT IKSLMDYWGQGTTVTVSS | 62 |
| HuD28S1 VH3 | EVQLVESGGGLVKPGGSLRLSCAASGFTFSSYGMSWVRQAPGKRLEWVST INTGGSYTYYPDSVKGRFTISRDNAKNSLYLQMNSLRAEDTAVYYCARHT IKSLMDYWGQGTTVTVSS | 63 |
| D28S1 VL | ETTVTQSPASLSMAIGEKVTIRCITSTDIDDDMNWYQQKPGEPPKLLISE GNTLRPGVPSRFSSSGYGTDFVFIIENMFSEDVADYYCLQSDNLPYTFGS GTKLEIK | 44 |
| HuD28S1 VL1 | ETTLTQSPAFMSATPGDKVNISCITSTDIDDDMNWYQQKPGEAAIFIIQE GNTLRPGIPPRFSGSGYGTDFTLTINNIESEDAAYYFCLQSDNLPYTFGQ GTKLEIK | 64 |
| HuD28S1 VL2 | ETTLTQSPAFMSATPGDKVNISCITSTDIDDDMNWYQQKPGEAAILIIQE GNTLRPGIPPRFSGSGYGTDFTLTINNIESEDAAYYFCLQSDNLPYTFGQ GTKLEIK | 65 |
| HuD28S1 VL3 | ETTLTQSPAFMSATPGDKVNISCITSTDIDDDMNWYQQKPGEAAILIIQE GNTLRPGVPPRFSGSGYGTDFTLTINNIESEDAAYYFCLQSDNLPYTFGQ GTKLEIK | 66 |
| HuD28S1 VL4 | ETTLTQSPAFMSATPGDKVNISCITSTDIDDDMNWYQQKPGEAAILLIQE GNTLRPGIPPRFSGSGYGTDFTLTINNIESEDAAYYFCLQSDNLPYTFGQ GTKLEIK | 67 |
| HuD28S1 VL5 | ETTLTQSPAFMSATPGDKVNISCITSTDIDDDMNWYQQKPGEAAILLISE GNTLRPGIPPRFSGSGYGTDFTLTINNIESEDAAYYFCLQSDNLPYTFGQ GTKLEIK | 68 |
| HuD28S1 VL6 | ETTLTQSPAFMSATPGDKVTIRCITSTDIDDDMNWYQQKPGEAAILIIQE GNTLRPGIPPRFSGSGYGTDFTLTINNIESEDAAYYFCLQSDNLPYTFGQ GTKLEIK | 69 |
| D28S1 VH | GAGGTGCAGCTGGTGGAGTCTGGGGGAGACTTAGTGAAGCCTGGAGGGTC CCTGAAACTCTCCTGTGCAGCCTCTGGATTCACTTTCACTAGCTATGGCA TGTCTTGGGTTCGCCAGACTCCAGACAAGAGGCTGGAGTGGGTCGCAACC ATTAATACTGGTGGTAGTTACACCTACTATCCAGACAGTGTGAAGGGGCG ATTCACCATCTCCAGAGACAATGCCAAGAACACCCTGTACCTGCAAATGA GCAGTCTGAAGTCTGAGGACACAGCCATGTATTACTGTGCAAGACATACT ATTAAATCTCTTATGGACTACTGGGGTCAAGGAACCTCAGTCACCGTCTC CTCA | 41 |
| HuD28S1 VH1 | GAGGTACAGTTGGTCGAATCCGGTGGGGGGCTTGTGAAGCCCGGAGGCAG CTTGCGGCTCTCATGTGCTGCAAGTGGCTTCACTTTCTCCTCATACGGCA TGAGTTGGGTACGACAAGCGCCAGGAAAAGGGCTTGAATGGGTGAGCACC ATCAATACCGGAGGATCATACACTTATTACCCAGATAGTGTCAAGGGTAG ATTCACCATCTCCAGGGATAATGCAAAGAATAGTTTGTACTTGCAGATGA ACAGCTTGAGAGCAGAGGACACTGCCGTGTATTACTGCGCTCGCCATACG ATTAAGAGTTTGATGGACTACTGGGGTCAAGGTACTACCGTCACAGTCAG TTCA | 70 |
| HuD28S1 VH2 | GAGGTACAGTTGGTCGAATCCGGTGGGGGGCTTGTGAAGCCCGGAGGCAG CTTGCGGCTCTCATGTGCTGCAAGTGGCTTCACTTTCACCTCATACGGCA TGAGTTGGGTACGACAAGCGCCAGGAAAAGGGCTTGAATGGGTGGCCACC ATCAATACCGGAGGATCATACACTTATTACCCAGATAGTGTCAAGGGTAG ATTCACCATCTCCAGGGATAATGCAAAGAATAGTTTGTACTTGCAGATGA ACAGCTTGAGAGCAGAGGACACTGCCGTGTATTACTGCGCTCGCCATACG ATTAAGAGTTTGATGGACTACTGGGGTCAAGGTACTACCGTCACAGTCAG TTCA | 71 |
| HuD28S1 VH3 | GAGGTACAGTTGGTCGAATCCGGTGGGGGGCTTGTGAAGCCCGGAGGCAG CTTGCGGCTCTCATGTGCTGCAAGTGGCTTCACTTTCTCCTCATACGGCA TGAGTTGGGTACGACAAGCGCCAGGAAAACGGCTTGAATGGGTGAGCACC ATCAATACCGGAGGATCATACACTTATTACCCAGATAGTGTCAAGGGTAG ATTCACCATCTCCAGGGATAATGCAAAGAATAGTTTGTACTTGCAGATGA | 72 |

TABLE 5-continued

Humanized D28S1 antibody sequences (bolded indicates CDR)

| Name | Sequence | SEQ ID NO: |
|---|---|---|
| | ACAGCTTGAGAGCAGAGGACACTGCCGTGTATTACTGCGCTCGCCATACG<br>ATTAAGAGTTTGATGGACTACTGGGGTCAAGGTACTACCGTCACAGTCAG<br>TTCA | |
| D28S1 VL | GAAACAACTGTGACCCAGTCTCCAGCATCCCTGTCCATGGCTATAGGAGA<br>AAAAGTCACCATCAGATGCATAACCAGCACTGATATTGATGATGATATGA<br>ACTGGTACCAGCAGAAGCCAGGGGAACCTCCTAAGCTCCTTATTTCAGAA<br>GGCAATACTCTTCGTCCTGGAGTCCCATCCCGATTCTCCAGCAGTGGCTA<br>TGGTACAGATTTTGTTTTTATAATTGAAAACATGTTCTCAGAAGATGTTG<br>CAGATTACTACTGTTTGCAAAGTGATAACTTGCCGTATACGTTCGGATCG<br>GGGACCAAGCTGGAAATAAAA | 43 |
| HuD28S1 VL1 | GAAACCACCCTCACCCAAAGTCCAGCCTTTATGTCCGCCACTCCCGGAGA<br>CAAGGTAAACATTTCTTGTATAACGTCAACGGACATTGACGATGACATGA<br>ATTGGTACCAACAAAAGCCGGGGAAGCCGCTATTTTCATAATTCAAGAA<br>GGTAATACGCTCAGACCCGGAATCCCTCCTCGCTTTAGTGGTAGCGGTTA<br>CGGCACGGACTTCACATTGACGATTAACAACATCGAGTCTGAAGACGCTG<br>CGTATTATTTCTGCCTTCAAAGTGATAACCTGCCTTATACGTTCGGACAA<br>GGTACTAAATTGGAGATTAAG | 73 |
| HuD28S1 VL2 | GAAACCACCCTCACCCAAAGTCCAGCCTTTATGTCCGCCACTCCCGGAGA<br>CAAGGTAAACATTTCTTGTATAACGTCAACGGACATTGACGATGACATGA<br>ATTGGTACCAACAAAAGCCGGGGAAGCCGCTATTCTCATAATTCAAGAA<br>GGTAATACGCTCAGACCCGGAATCCCTCCTCGCTTTAGTGGTAGCGGTTA<br>CGGCACGGACTTCACATTGACGATTAACAACATCGAGTCTGAAGACGCTG<br>CGTATTATTTCTGCCTTCAAAGTGATAACCTGCCTTATACGTTCGGACAA<br>GGTACTAAATTGGAGATTAAG | 74 |
| HuD28S1 VL3 | GAAACCACCCTCACCCAAAGTCCAGCCTTTATGTCCGCCACTCCCGGAGA<br>CAAGGTAAACATTTCTTGTATAACGTCAACGGACATTGACGATGACATGA<br>ATTGGTACCAACAAAAGCCGGGGAAGCCGCTATTCTCATAATTCAAGAA<br>GGTAATACGCTCAGACCCGGAGTCCCTCCTCGCTTTAGTGGTAGCGGTTA<br>CGGCACGGACTTCACATTGACGATTAACAACATCGAGTCTGAAGACGCTG<br>CGTATTATTTCTGCCTTCAAAGTGATAACCTGCCTTATACGTTCGGACAA<br>GGTACTAAATTGGAGATTAAG | 75 |
| HuD28S1 VL4 | GAAACCACCCTCACCCAAAGTCCAGCCTTTATGTCCGCCACTCCCGGAGA<br>CAAGGTAAACATTTCTTGTATAACGTCAACGGACATTGACGATGACATGA<br>ATTGGTACCAACAAAAGCCGGGGAAGCCGCTATTCTCCTAATTCAAGAA<br>GGTAATACGCTCAGACCCGGAATCCCTCCTCGCTTTAGTGGTAGCGGTTA<br>CGGCACGGACTTCACATTGACGATTAACAACATCGAGTCTGAAGACGCTG<br>CGTATTATTTCTGCCTTCAAAGTGATAACCTGCCTTATACGTTCGGACAA<br>GGTACTAAATTGGAGATTAAG | 76 |
| HuD28S1 VL5 | GAAACCACCCTCACCCAAAGTCCAGCCTTTATGTCCGCCACTCCCGGAGA<br>CAAGGTAAACATTTCTTGTATAACGTCAACGGACATTGACGATGACATGA<br>ATTGGTACCAACAAAAGCCGGGGAAGCCGCTATTCTCCTAATTTCAGAA<br>GGTAATACGCTCAGACCCGGAATCCCTCCTCGCTTTAGTGGTAGCGGTTA<br>CGGCACGGACTTCACATTGACGATTAACAACATCGAGTCTGAAGACGCTG<br>CGTATTATTTCTGCCTTCAAAGTGATAACCTGCCTTATACGTTCGGACAA<br>GGTACTAAATTGGAGATTAAG | 77 |
| HuD28S1 VL6 | GAAACCACCCTCACCCAAAGTCCAGCCTTTATGTCCGCCACTCCCGGAGA<br>CAAGGTAACCATTCGTTGTATAACGTCAACGGACATTGACGATGACATGA<br>ATTGGTACCAACAAAAGCCGGGGAAGCCGCTATTCTCATAATTCAAGAA<br>GGTAATACGCTCAGACCCGGAATCCCTCCTCGCTTTAGTGGTAGCGGTTA<br>CGGCACGGACTTCACATTGACGATTAACAACATCGAGTCTGAAGACGCTG<br>CGTATTATTTCTGCCTTCAAAGTGATAACCTGCCTTATACGTTCGGACAA<br>GGTACTAAATTGGAGATTAAG | 78 |

The humanized VH and VK genes were produced synthetically and then respectively cloned into vectors containing the human gamma 1 and human kappa constant domains. The pairing of the human VH and the human VK created 18 humanized antibodies (see Table 6).

were grafted onto framework sequences of the VH3-72/JH4. A 3D model was then generated to determine if there were any framework positions where replacing the mouse amino acid to the human amino acid could affect binding and/or CDR conformation. In the case of the heavy chain, G49A, A99I, R100E in the framework were involved in back-mutations (Kabat numbering, see Table 7)

TABLE 6

Humanized D28S1 antibodies with their VH and VL regions

| Vk VH | HuD28S1VL | HuD28S1VL1 | HuD28S1VL2 | HuD28S1VL3 | HuD28S1VL4 | HuD28S1VL5 | HuD28S1VL6 |
|---|---|---|---|---|---|---|---|
| D28S1VH | D28S1VH/VL | | | | | | |
| HuD28S1VH1 | | HuD28S1VH1/L1 | HuD28S1VH1/L2 | HuD28S1VH1/L3 | HuD28S1VH1/L4 | HuD28S1VH1/L5 | HuD28S1VH1/L6 |
| HuD28S1VH2 | | HuD28S1VH2/L1 | HuD28S1VH2/L2 | HuD28S1VH2/L3 | HuD28S1VH2/L4 | HuD28S1VH2/L5 | HuD28S1VH2/L6 |
| HuD28S1VH3 | | HuD28S1VH3/L1 | HuD28S1VH3/L1 | HuD28S1VH3/L3 | HuD28S1VH3/L4 | HuD28S1VH3/L5 | HuD28S1VH3/L6 |

Example 8: Humanization of Mouse Anti-Human CD47 Antibody D36S4

The mAb D36S4 variable region genes were employed to create a humanized MAb. In the first step of this process, the amino acid sequences of the VH and VK of MAb D36S4 were compared against the available database of human Ig gene sequences to find the overall best-matching human germline Ig gene sequences. For the light chain, the closest human match was the Vk4-1/Jk1 and Vk2-40/Jk1 genes, and for the heavy chain the closest human match was the VH3-72/JH4 gene.

Humanized variable domain sequences were then designed where the CDR1 (SEQ ID NO. 13), 2 (WAS) and 3 (SEQ ID NO.15) of the D36S4 light chain were grafted onto framework sequences of the Vk4-1/Jk1 or Vk2-40/Jk1 gene, and the CDR1 (SEQ ID NO.16), 2 (SEQ ID NO.17), and 3 (SEQ ID NO.18) sequences of the D36S4 heavy chain

TABLE 7

Humanization Design for D36S4

| Construct | Mutation |
|---|---|
| VH Design: VH3-72/JH4 | |
| D36S4 VH | Chimera |
| HuD36S4 VH1 | CDR-grafted |
| HuD36S4 VH2 | A99I, R100E |
| HuD36S4 VH3 | G49A, A99I, R100E |
| VK Design: Vk4-1/Jk1 or Vk2-40/Jk1 | |
| D36S4 VL | Chimera |
| HuD36S4 VL1 | CDR-grafted on Vk4-1/Jk1 |
| HuD36S4 VL2 | CDR-grafted on Vk2-40/Jk1 |

The amino acid and nucleotide sequences of some of the humanized antibody are listed in Table 8 below.

TABLE 8

Humanized D36S4 antibody sequences (bolded indicates CDR)

| Name | Sequence | SEQ ID NO: |
|---|---|---|
| Chimeric D36S4 VH | EVKLEESGGGLVQPGGSMKLSCVASGFTFS RYWMN WVRQSPDKGLEWVA QIRLKSDNYETHYAESVKG RFTISRDDSKSSVYLQMNNLRAEDTGIYYCIE EGGYYVPFAY WGQGTLVTVSA | 46 |
| HuD36S4 VH1 | EVQLVESGGGLVQPGGSLRLSCAASGFTFS RYWMN WVRQAPGKGLEWVG QIRLKSDNYETHYAESVKG RFTISRDDSKNSLYLQMNSLKTEDTAVYYCAR EGGYYVPFAY WGQGTLVTVSS | 79 |
| HuD36S4 VH2 | EVQLVESGGGLVQPGGSLRLSCAASGFTFS RYWMN WVRQAPGKGLEWVG QIRLKSDNYETHYAESVKG RFTISRDDSKNSLYLQMNSLKTEDTAVYYCIE EGGYYVPFAY WGQGTLVTVSS | 80 |
| HuD36S4 VH3 | EVQLVESGGGLVQPGGSLRLSCAASGFTFS RYWMN WVRQAPGKGLEWVA QIRLKSDNYETHYAESVKG RFTISRDDSKSSLYLQMNSLKTEDTAVYYCIE EGGYYVPFAY WGQGTLVTVSS | 81 |
| Chimeric D36S4 VL | DIWSQSPSSLAVSAGEKVTMSC KSSQSLFKSRTRKNYLA WYQQRPGQSPKLLIY WASIRES GVPDRFTGSGSGTEFTLTISSVQAEDLAVYYC KQSYYLLT FGAGTKLELK | 48 |
| HuD36S4 VL1 | DIVMTQSPDSLAVSLGERATINC KSSQSLFKSRTRKNYLA WYQQKPGQPPKLLIY WASIRES GVPDRFSGSGSGTDFTLTISSLQAEDVAVYYC KQSYYLLT FGGGTKVEIK | 82 |

TABLE 8-continued

Humanized D36S4 antibody sequences (bolded indicates CDR)

| Name | Sequence | SEQ ID NO: |
|---|---|---|
| HuD36S4 VL2 | DIVMTQTPLSLPVTPGEPASISC KSSQSLFKSRTRKNYLA WYLQKPGQSPQLLIY WASIRES GVPDRFSGSGSGTDFTLKISRVEAEDVGVYYC KQSYYLLT FGGGTKVEIK | 2 |
| Chimeric D36S4 VH | GAAGTGAAGCTTGAGGAGTCTGGAGGAGGCTTGGTGCAACCTGGAGGATCCATGA AACTCTCCTGTGTTGCCTCTGGATTCACTTTCAGTAGATACTGGATGAACTGGGT CCGCCAGTCTCCAGACAAGGGGCTTGAGTGGGTTGCTCAAATTAGATTGAAATCT GATAATTATGAAACACATTATGCGGAGTCTGTGAAAGGGAGGTTCACCATCTCAA GAGATGATTCCAAAAGTAGTGTCTACCTGCAAATGAACAACTTAAGGGCTGAAGA CACTGGAATTTATTATTGTATAGAAGAGGGGGGTTACTACGTCCCGTTTGCTTAC TGGGGCCAAGGGACTCTGGTCACTGTCTCTGCA | 45 |
| HuD36S4 VH1 | GAGGTGCAACTCGTAGAATCAGGGGGCGGACTCGTTCAACCTGGCGGGAGTCTTA GACTTAGTTGTGCTGCATCAGGCTTTACATTTTCACGCTACTGGATGAATTGGGT CCGGCAGGCTCCCGGAAAAGGTCTGGAATGGGTAGGGCAGATTCGGCTCAAATCA GATAATTACGAAACTCACTACGCGGAATCAGTGAAGGGACGGTTTACAATCAGTC GCGATGATAGTAAGAACAGTTTGTATTTGCAGATGAACAGTTTGAAAACAGAAGA CACCGCTGTCTATTACTGCGCTAGAGAAGGCGGATACTATGTCCCATTTGCGTAC TGGGGACAAGGGACCCTCGTAACTGTTTCCAGC | 8 |
| HuD36S4 VH2 | GAGGTGCAACTCGTAGAATCAGGGGGCGGACTCGTTCAACCTGGCGGGAGTCTTA GACTTAGTTGTGCTGCATCAGGCTTTACATTTTCACGCTACTGGATGAATTGGGT CCGGCAGGCTCCCGGAAAAGGTCTGGAATGGGTAGGGCAGATTCGGCTCAAATCA GATAATTACGAAACTCACTACGCGGAATCAGTGAAGGGACGGTTTACAATCAGTC GCGATGATAGTAAGAACAGTTTGTATTTGCAGATGAACAGTTTGAAAACAGAAGA CACCGCTGTCTATTACTGCATTGAAGAAGGCGGATACTATGTCCCATTTGCGTAC TGGGGACAAGGGACCCTCGTAACTGTTTCCAGC | 14 |
| HuD36S4 VH3 | GAGGTGCAACTCGTAGAATCAGGGGGCGGACTCGTTCAACCTGGCGGGAGTCTTA GACTTAGTTGTGCTGCATCAGGCTTTACATTTTCACGCTACTGGATGAATTGGGT CCGGCAGGCTCCCGGAAAAGGTCTGGAATGGGTAGCGCAGATTCGGCTCAAATCA GATAATTACGAAACTCACTACGCGGAATCAGTGAAGGGACGGTTTACAATCAGTC GCGATGATAGTAAGAGCAGTTTGTATTTGCAGATGAACAGTTTGAAAACAGAAGA CACCGCTGTCTATTACTGCATTGAAGAAGGCGGATACTATGTCCCATTTGCGTAC TGGGGACAAGGGACCCTCGTAACTGTTTCCAGC | 20 |
| Chimeric D36S4 VL | GACATTGTCGTGTCACAGTCTCCATCCTCCCTGGCTGTGTCAGCAGGAGAGAAGG TCACTATGAGCTGCAAATCCAGTCAGAGTCTGTTCAAAAGTAGAACCCGAAAGAA CTACTTGGCTTGGTACCAGCAGAGACCAGGGCAGTCTCCTAAACTGCTGATCTAC TGGGCATCCATTAGGGAATCTGGGGTCCCTGATCGCTTCACAGGCAGTGGATCTG GGACAGAATTCACTCTCACCATCAGCAGTGTGCAGGCTGAAGACCTGGCAGTTTA TTACTGCAAGCAATCTTATTATCTACTCACGTTCGGTGCTGGGACCAAACTGGAG CTGAAA | 47 |
| HuD36S4 VL1 | GACATCGTGATGACACAGTCTCCTGACAGCCTTGCGGTCTCACTGGGGAACGCG CGACAATTAACTGCAAATCCTCTCAGTCACTGTTCAAGAGCAGGACCCGAAAAAA TTATCTGGCATGGTATCAGCAGAAACCTGGACAGCCGCCAAAACTGCTCATCTAC TGGGCGTCAATACGCGAAAGTGGAGTGCCGGATCGGTTCAGTGGATCAGGTTCTG GCACAGATTTTACCCTTACGATCTCCAGTTTGCAGGCGGAAGACGTAGCAGTATA CTACTGCAAACAGTCTTACTACCTTCTTACCTTCGGAGGTGGCACTAAGGTAGAG ATCAAA | 26 |
| HuD36S4 VL2 | GATATAGTAATGACCCAGACGCCTCTGTCACTCCCCGTCACACCAGGGGAACCTG CGTCTATAAGTTGCAAATCATCACAATCTCTCTTCAAGTCTCGGACTCGGAAAAA CTACTTGGCCTGGTACTTGCAGAAGCCGGGGCAAAGTCCTCAGCTTCTCATATAT TGGGCATCCATCCGGGAGTCCGGTGTACCAGACCGGTTTTCAGGGTCTGGCTCAG GGACCGATTTCACTTTGAAAATAAGCCGGGTGGAAGCTGAGGATGTAGGAGTCTA TTACTGCAAACAGTCTTATTATCTGCTCACGTTCGGAGGTGGCACCAAAGTTGAG ATCAAA | 32 |

The humanized VH and VK genes were produced synthetically and then respectively cloned into vectors containing the human gamma 1 and human kappa constant domains. The pairing of the human VH and the human VK created 6 humanized antibodies (see Table 9).

TABLE 9

Humanized D36S4 antibodies with their VH and VL regions

| VH | HuD36S4VL | HuD36S4VL1 | HuD36S4VL2 |
|---|---|---|---|
| D36S4VH | D36S4 H/L | | |
| HuD36S4VH1 | | HuD36S4 H1/L1 | HuD36S4 H1/L2 |
| HuD36S4VH2 | | HuD36S4 H2/L1 | HuD36S4 H2/L2 |
| HuD36S4VH3 | | HuD36S4 H3/L1 | HuD36S4 H3/L2 |

Vk

Example 9: Humanized D36S4 Antibodies Blocked Binding Activity of Human CD47 to its Ligand, SIRP Alpha To evaluate the blocking effects of the humanized D36S4 antibodies on human CD47 binding to its ligand SIRPα, humanized D36S4 antibodies were produced from HEK293 cells. Briefly, HuD36S4 antibody heavy and light chain V regions were cloned into transient expression vectors containing human antibody heavy chain IgG1 and light chain constant regions. The resulting antibody heavy and light chain expression constructs were used to transfect HEK293 cells. The culture supernatants were harvested and loaded onto protein A Sepharose columns (GE Healthcare). The columns were washed and antibodies were then eluted with eluting buffer (0.1 M glycine buffer, pH 3.0). Collected fractions were neutralized with 1 M Tris-HCl, pH 8.0, pooled together and then dialyzed against PBS. Purity of the antibodies was analyzed by sodium dodecyl sulfate polyacrylamide gel electrophoresis (SDS-PAGE) under both reducing and non-reducing conditions.

Figure 12:
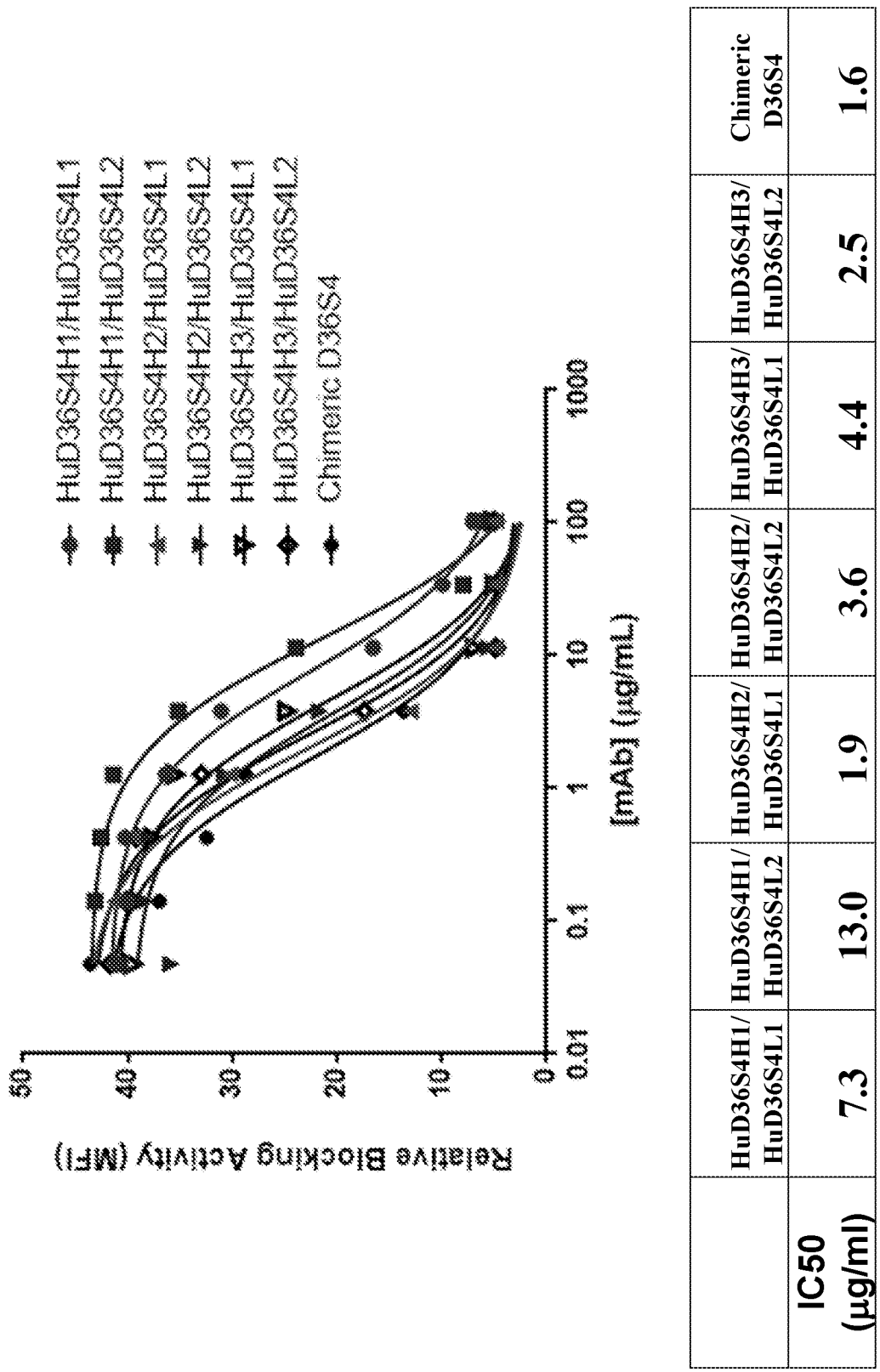
FIG. 12 shows blocking of SIRPalpha binding to human CD47 on CHO cells by humanized D36S4 antibodies in FACS analysis. SIRPα FITC used at 5 µg/ml

To evaluate the blocking ability of humanized D36S4 antibodies on interactions between human full length CD47 expressed on CHO cells and its ligand SIRPalpha, the FACS-based ligand blocking assay was used. CD47-CHO cells were first incubated with serially diluted humanized D36S4 antibodies starting at 100 µg/ml on ice for 30 min. After washing by FACS buffer once (PBS with 2% FBS), 5 µg/ml of FITC labeled human SIRPα huFc protein was added to the cells and incubated on ice for another 15 min. The cells were then washed 3 times with the FACS buffer and the mean florescence intensities (MFI) of FITC were evaluated by FACS Caliber. As shown in FIG. 12, all six humanized D36S4 antibodies can efficiently inhibit the binding of SIRPα onto CD47 expressed CHO cells. The IC50s were between 1.9-13 µg/ml (FIG. 12). HuD36S4H2/L1, HuD36S4H2/L2, HuD36S4H3/L1, HuD36S4H3/L2 had similar IC50 as the chimeric D36S4 antibody (FIG. 12).

Figure 13:
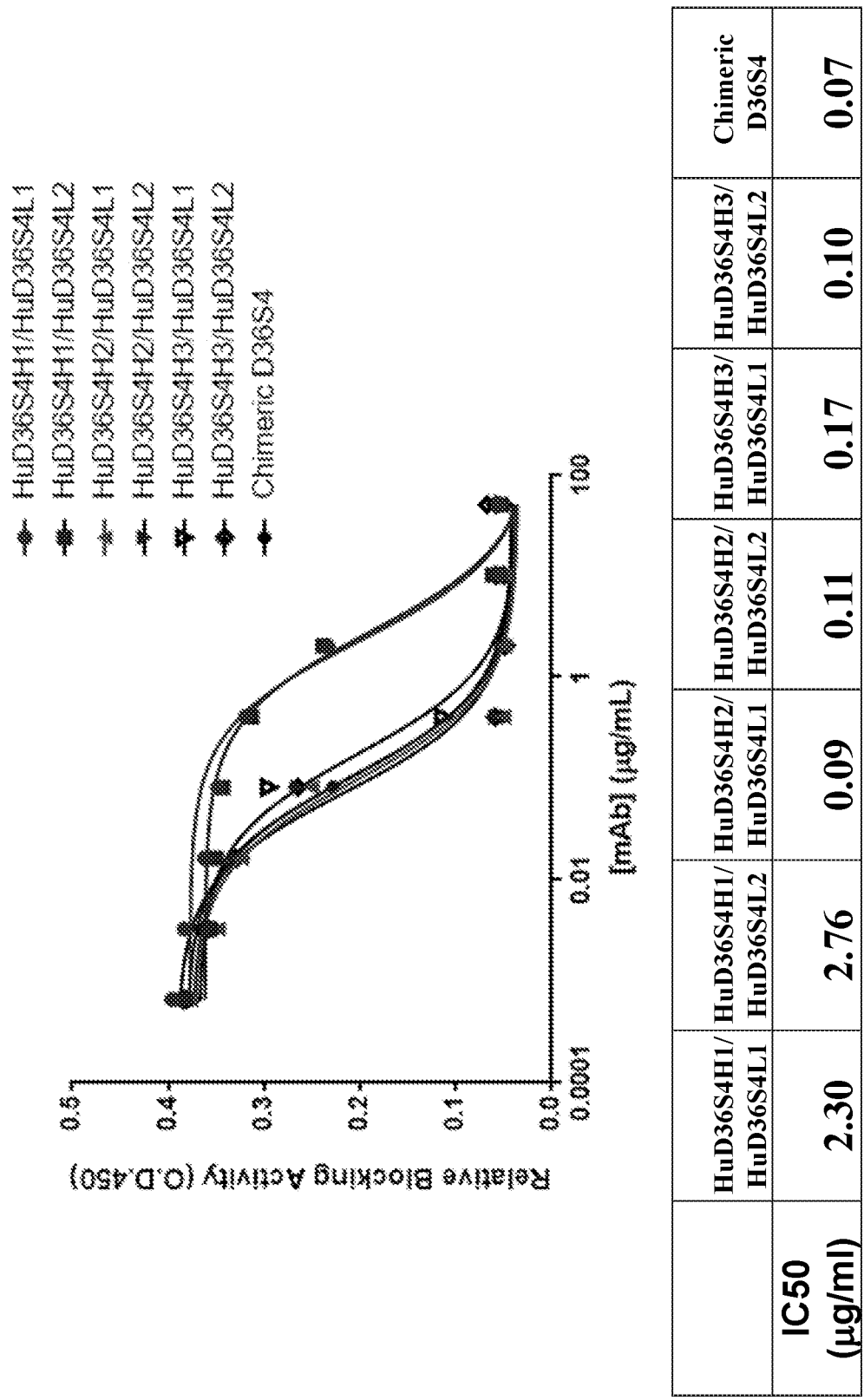
FIG. 13 shows blocking of SIRPalpha binding to plate-bound human CD47 by humanized D36S4 antibodies in ELISA. ELISA plates were coated with 1 µg/ml human CD47 ECD HF tagged protein and soluble human SIRPαECD muFc were added at 1 µg/ml.

To evaluate the blocking activities of humanized D36S4 antibodies on recombinant human CD47 binding to its ligand SIRPα, an ELISA-based ligand blocking assay was employed. Briefly, microtiter plates were coated with human CD47ECD His tagged protein at 1 µg/ml in PBS, 100 µl/well at 4° C. overnight, then blocked with 100 µl/well of 2% BSA. 50 µl of human SIRPα muFc protein (1 ug/ml) and serial dilutions of humanized D36S4 antibodies starting from 50 µg/ml at 50 µl were added to each well and incubated for 1 hour at 37° C. The plates were washed with PBS/Tween and then incubated with anti-mouse IgG-HRP for 1 hour at 37° C. After washing, the plates were developed with TMB substrate and analyzed by spectrophotometer at OD 450 nm. As shown in FIG. 13, all of the humanized D36S4 antibodies can efficiently inhibit the binding of human SIRPα to human CD47. HuD36S4H2/L1, HuD36S4H2/L2, HuD36S4H3/L1, and HuD36S4H3/L2 had similar IC50 as the chimeric D36S4 antibody (FIG. 13).

Example 10: Hemagglutination Activity of Anti-CD47 Antibodies

To determine hemagglutination activity of anti-CD47 antibodies, human whole blood or purified red blood cells were used. To purify red blood cells (RBCs), human whole blood was centrifuged at 500×g for 10 min at 4 degree C. and washed with PBS for 3 times as described (Hanson, M. S. et al. 2008). Human whole blood or RBCs were diluted to 10% in PBS and incubated at 37 degrees C. for 4 hours in the presence of anti-CD47 antibodies in a U-bottom 96-well plate. The presence of unsettled RBCs with a haze appearance indicates hemagglutination.

Figure 9A:
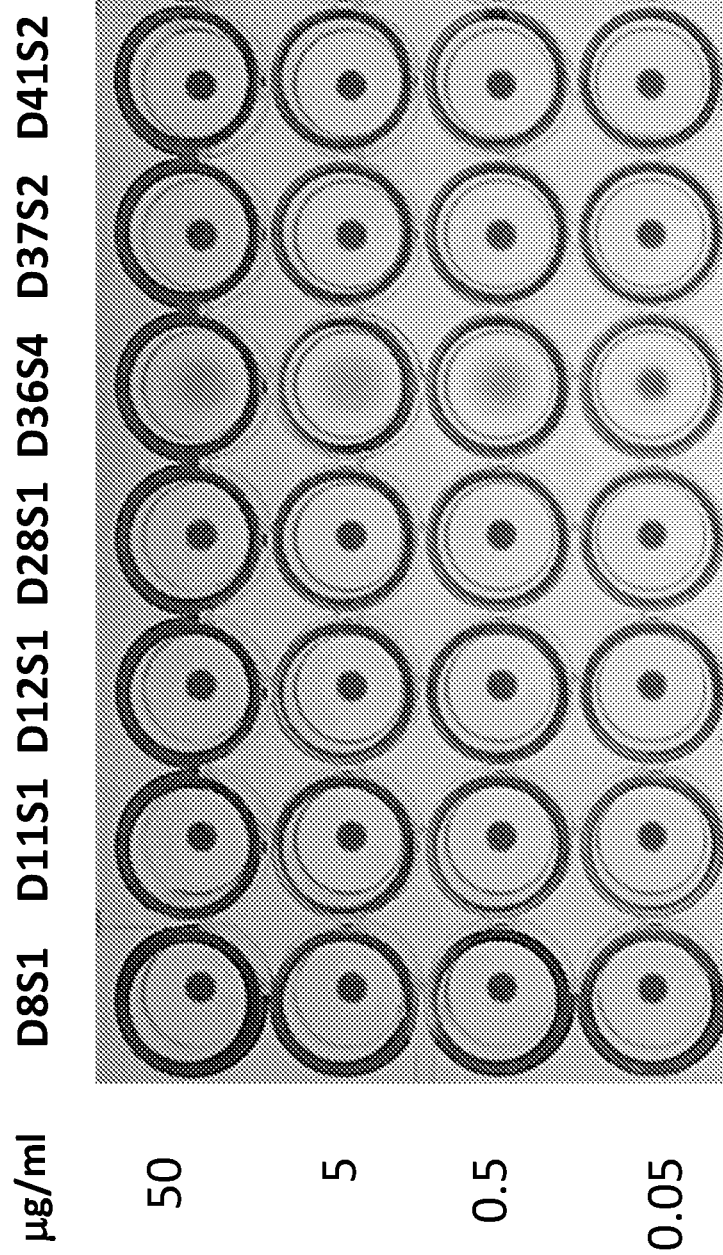
FIG. 9a-b show that most of the mouse anti-CD47 hybridoma antibodies do not cause red blood cell agglutination using human whole blood while D36S4, D90S1, D96S1, and D89S4 cause hemagglutination.
Figure 9B:
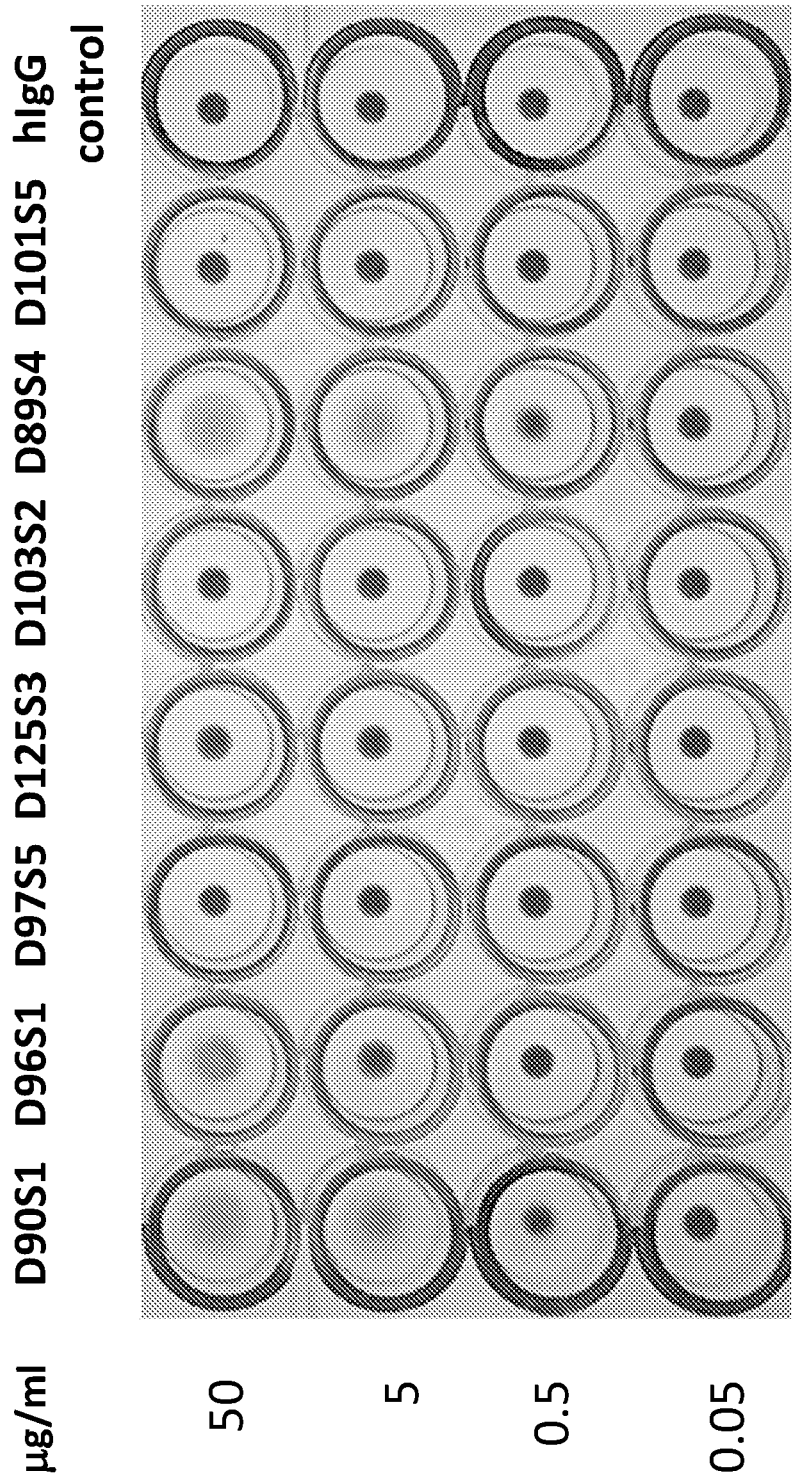
Figure 9C:
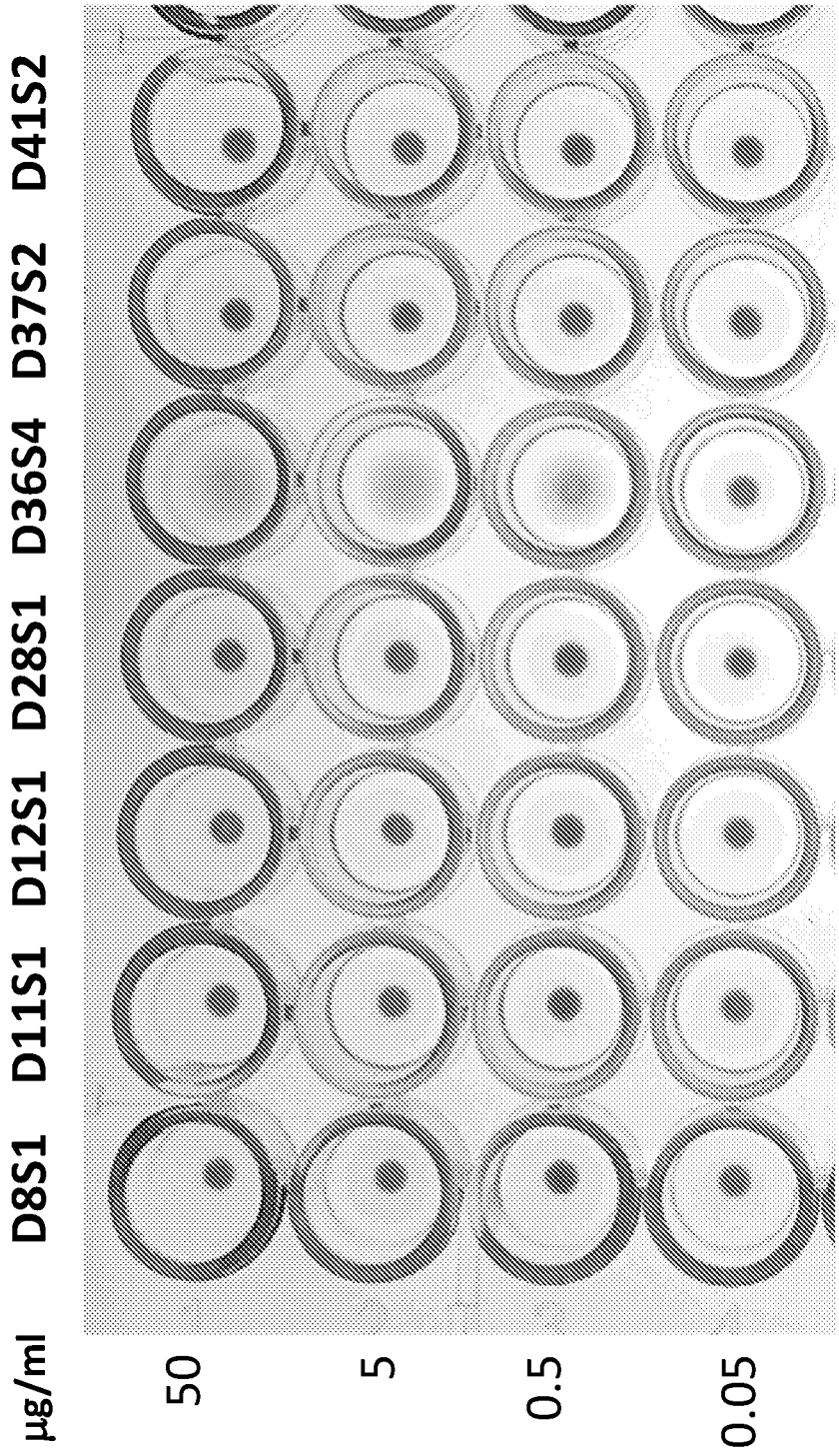
FIG. 9c-d show that most of the mouse anti-CD47 hybridoma antibodies do not cause red blood cell agglutination using purified human red blood cells while D36S4, D90S1, D96S1, and D89S4 cause a modest agglutination.
Figure 9D:
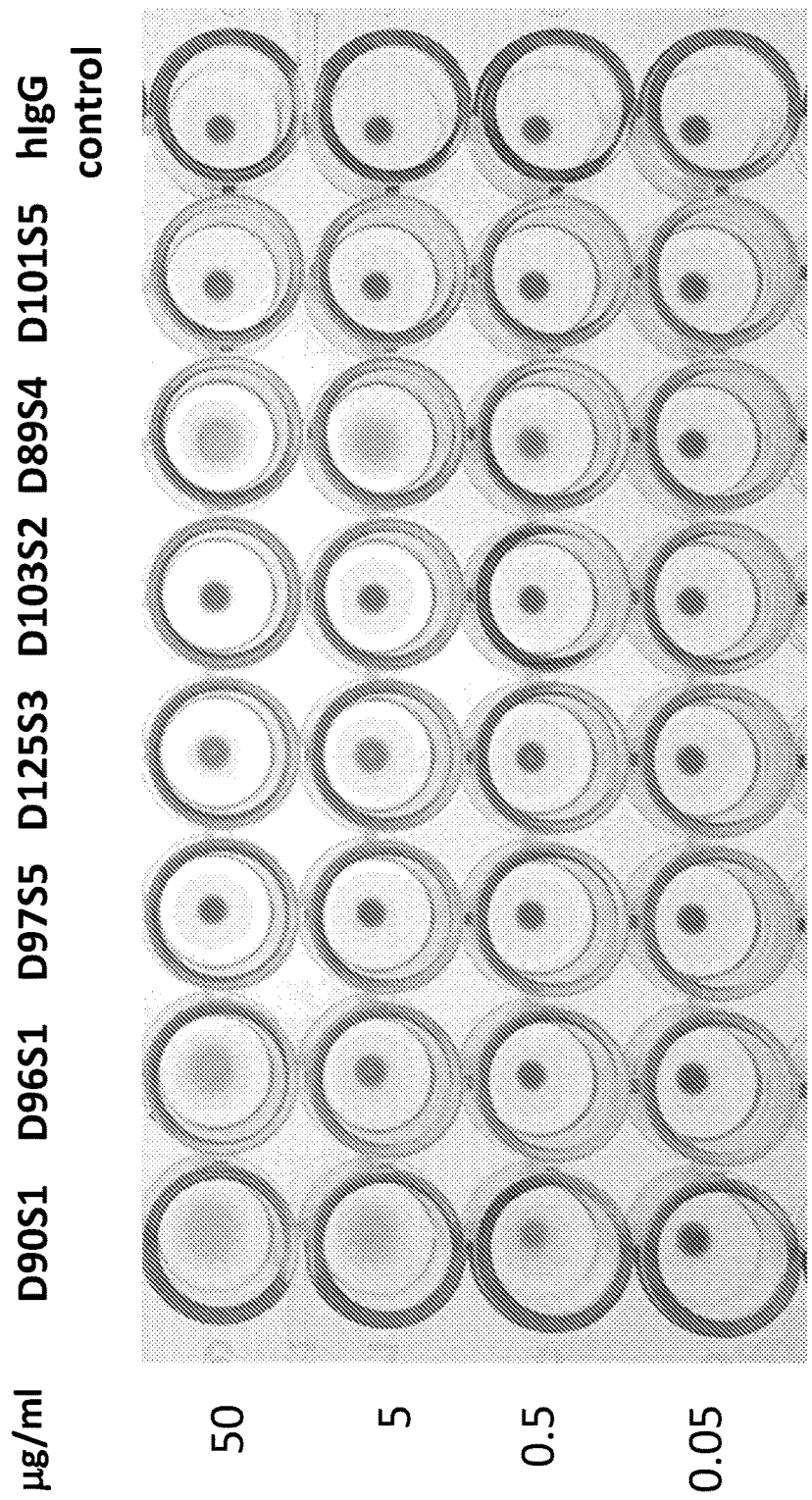

As shown in FIG. 9a-d, some of the anti-CD47 antibodies, including D36S4, D89S4, D90S1, and D96S1, caused hemagglutination in human whole blood (FIG. 9a, 9b), while others including D8S1, D11S1, D12S1, D28S1, D37S2, D41S2, D97S5, D125S3, D103S2, D101S5, and a negative control antibody, did not (FIG. 9a, 9b). Similar results of hemagglutination for the anti-CD47 antibodies were obtained using purified RBCs, demonstrating the lack of hemagglutination activity of D8S1, D11S1, D12S1, D28S1, D37S2, D41S2, D97S5, D125S3, D103S2, and D101S5 (FIG. 9c, 9d).

Example 11: Chimeric Anti-CD47 Antibodies Enhanced Macrophage Phagocytosis of B Lymphoma Cell In vitro phagocytosis assays were performed using human lymphoma cell line Raji labeled with CFSE and human peripheral blood-derived macrophages. The CFSE labeled Raji cells were incubated with human macrophages in the presence of anti-CD47 antibodies or a negative control antibody at 37° C. for 2 hours. The cell culture plate was then washed with PBS for 3 times to remove the non-phagocytosed Raji cells and the cells were analyzed by fluorescence microscopy to determine the phagocytic index (number of cells ingested per 100 macrophages).

Figure 10A:
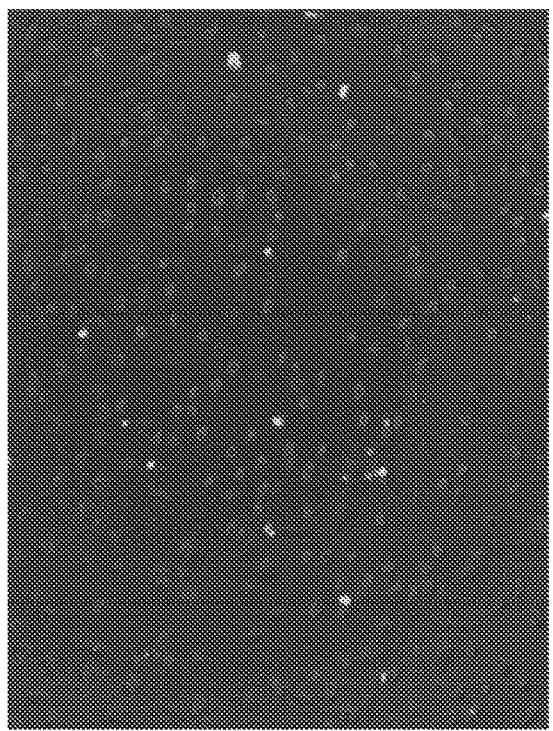
FIG. 10a-c show that the mouse/human chimeric anti-CD47 antibodies enhance macrophage phagocytosis of human B Lymphoma Raji cells with D8S1, D28S1, D36S4, and D96S1 displaying similar or better phagocytosis activities than AB6.12.
Figure 10A:
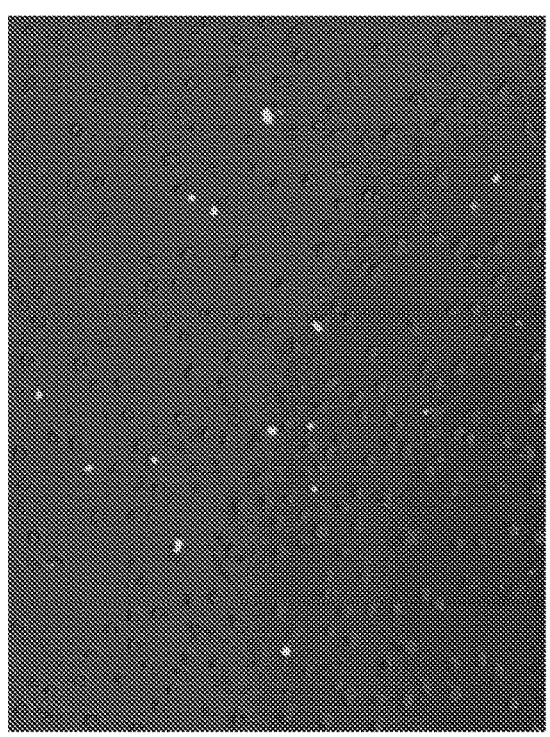
Figure 10A:
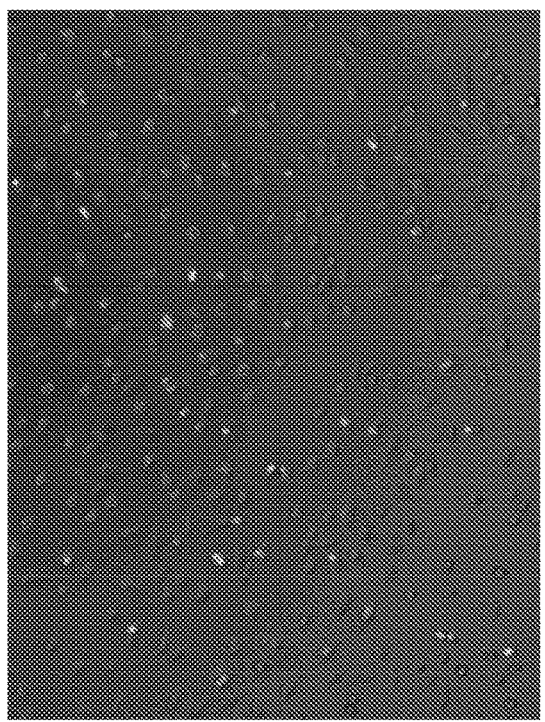
Figure 10A:
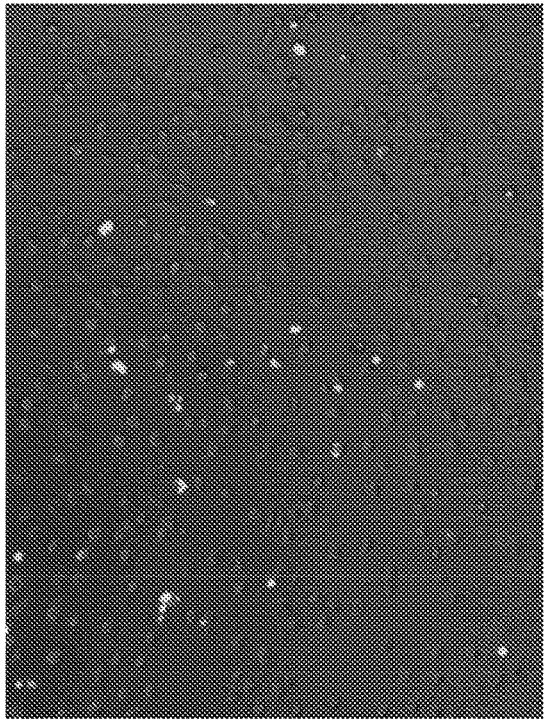
Figure 10B:
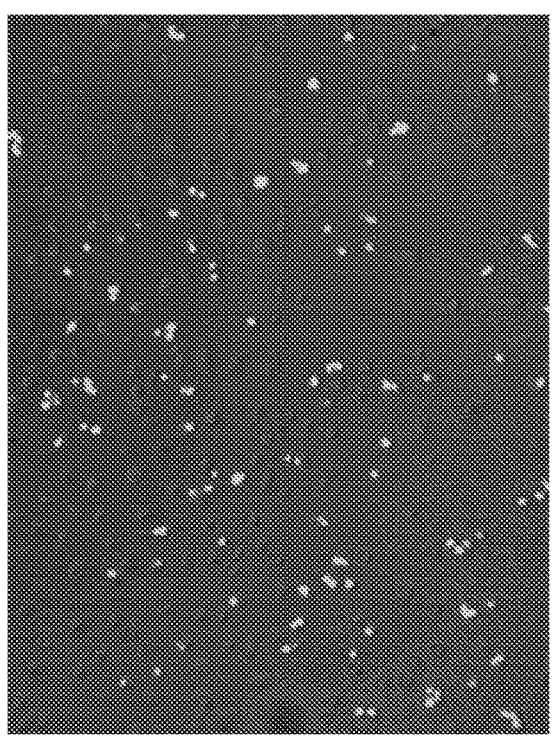
Figure 10B:
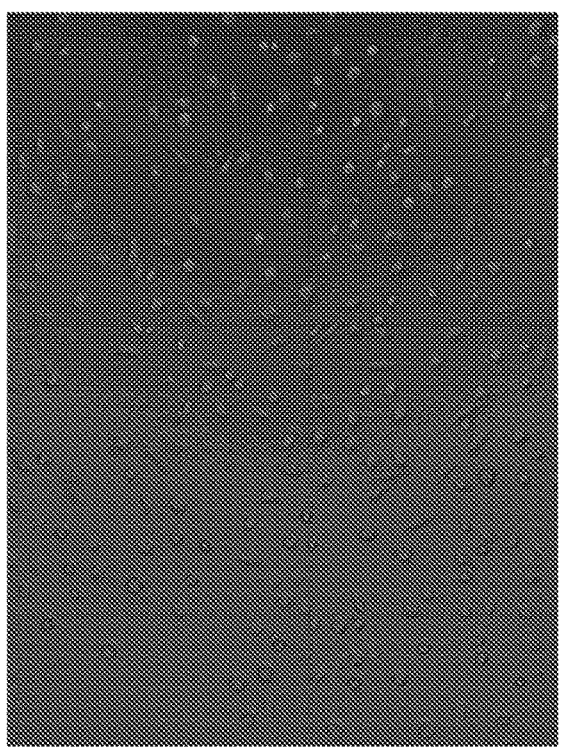
Figure 10B:
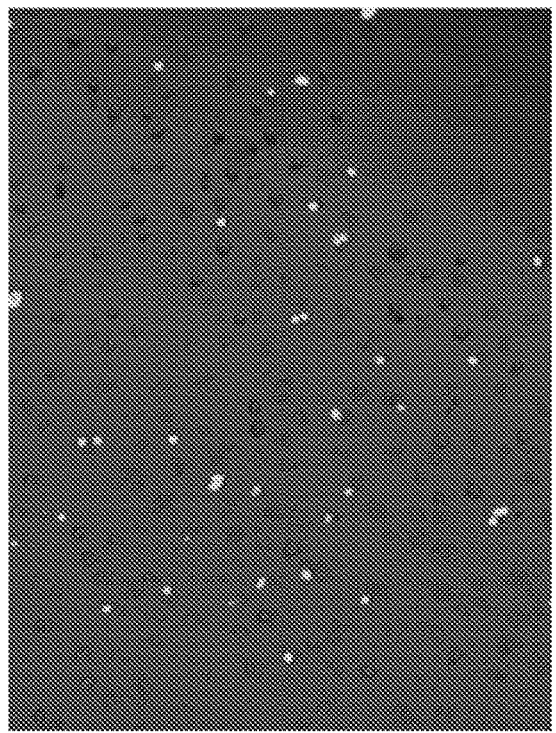
Figure 10B:
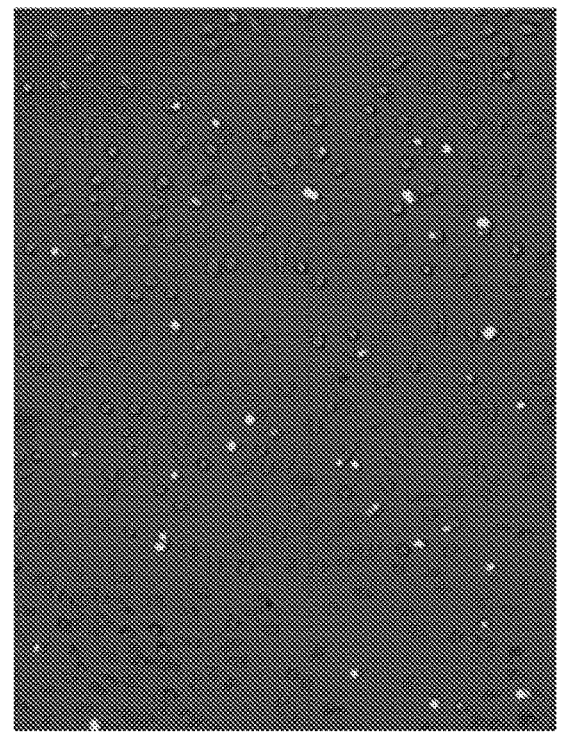
Figure 10C:
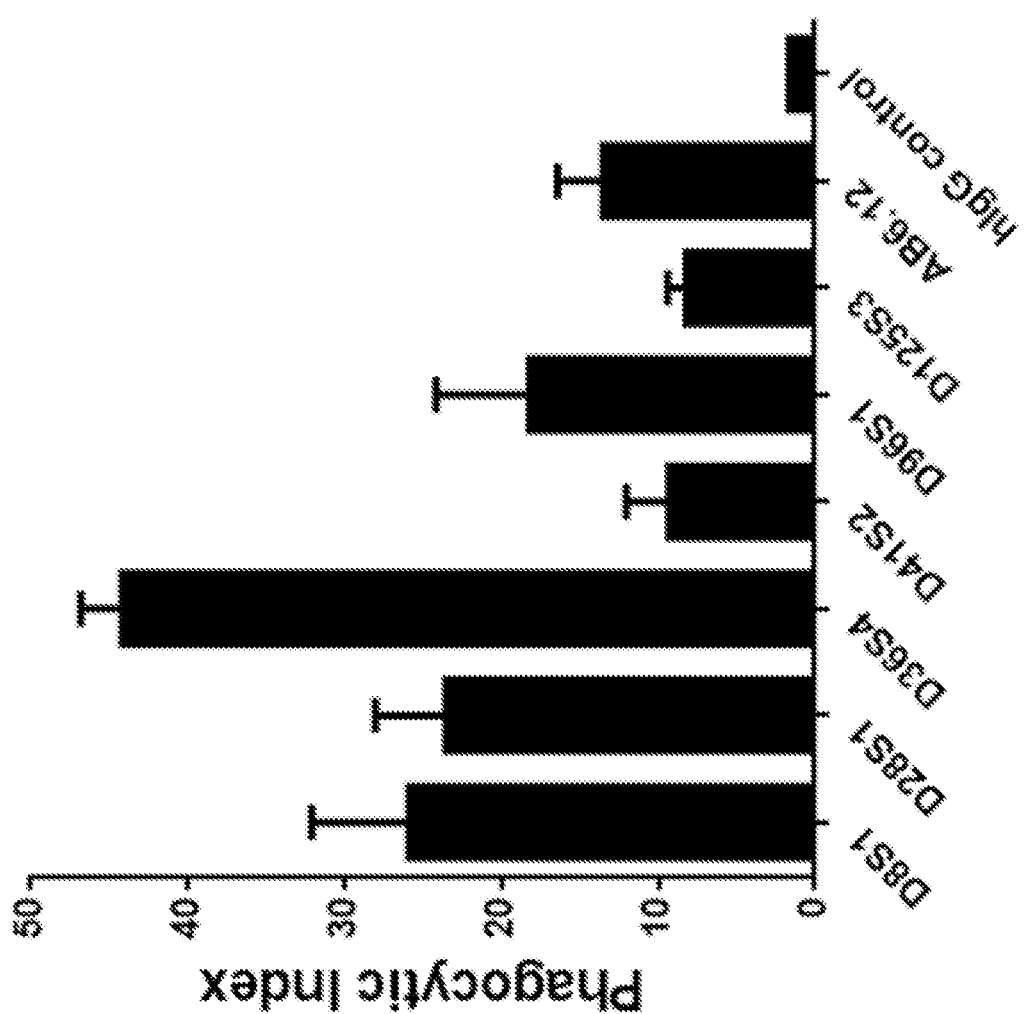

The chimeric anti-CD47 antibodies with potent blocking activity for CD47-SIRPα interaction were chosen for analysis in the phagocytosis assay. As shown in FIGS. 10a and 10b, the chimeric anti-CD47 antibodies enhanced macrophage phagocytosis of human B Lymphoma Raji cells, with D8S1, D28S1, D36S4, and D96S1 showing similar or better phagocytosis activities than the positive control antibody, AB6.12. The phagocytosed Raji cells were quantified to determine the phagocytotic index. As shown in FIG. 10c, the chimeric antibody D36S4 had the highest phagocytic index. D8S1, D28S1, and D96S1 also had similar or higher phagocytosis activity compared to the positive control antibody, AB6.12. The chimeric antibodies D41S2 and D125S3 also displayed phagocytosis activity (FIG. 10c).

Example 12: Hemagglutination Activity of Chimeric Anti-CD47 Antibodies

Figure 11:
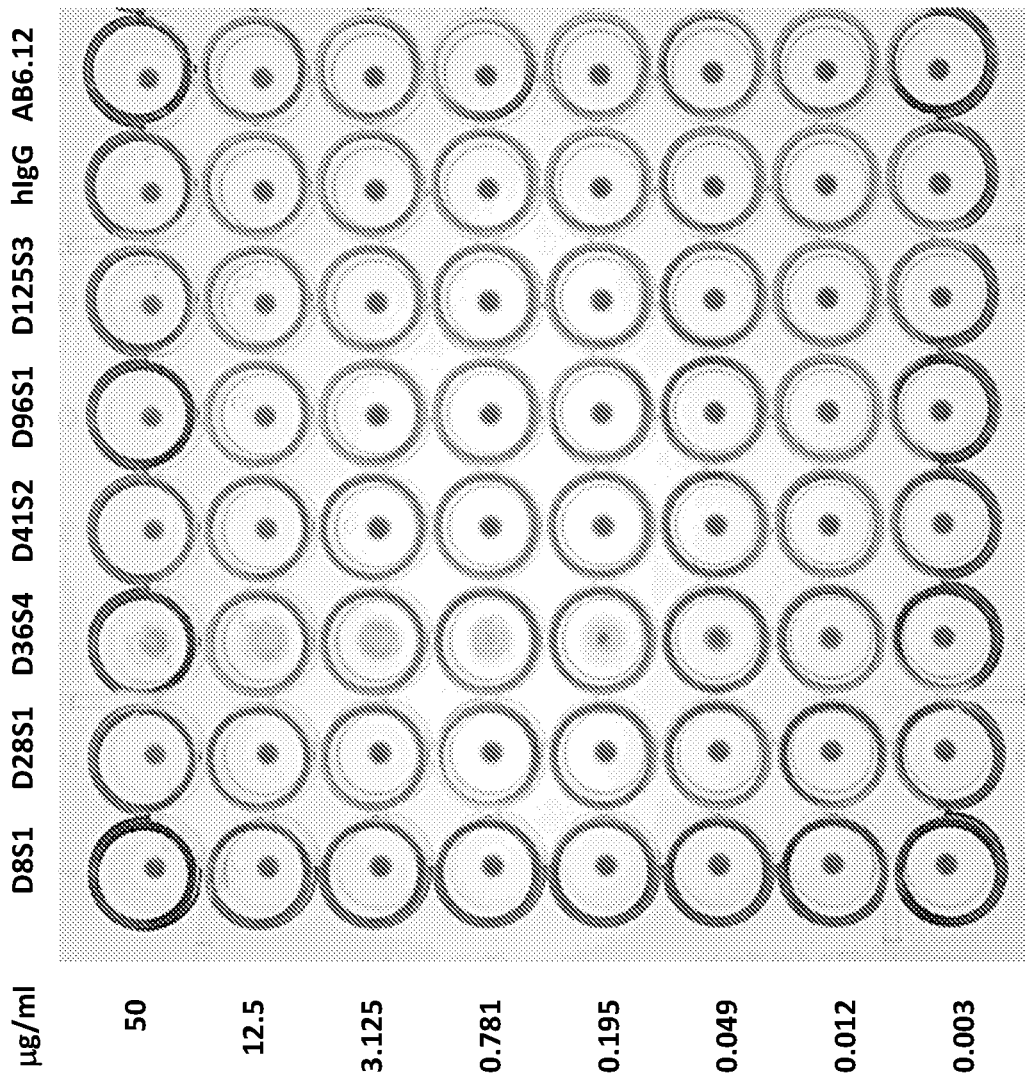
FIG. 11 shows that most of the mouse/human chimeric anti-CD47 antibodies do not cause red blood cell hemagglutination using purified human red blood cells while only D36S4 causes a modest hemagglutination.

The hemagglutination activity of chimeric anti-CD47 antibodies was also analyzed using human whole blood. As shown in FIG. 11, the chimeric D36S4 antibody at concentrations above 50 ng/ml caused hemagglutination, while all other chimeric anti-CD47 antibodies, including D8S1, D28S1, D41S2, D96S1, and D125S3, as well as the positive control AB6.12 antibody and the negative control hIgG1, did not cause hemagglutination (FIG. 11).

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. An antibody or fragment thereof having binding specificity to a human CD47 (cluster of differentiation 47) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1 comprises the amino acid sequence of SEQ ID NO:25, the CDRL2 comprises the amino acid sequence YTS, the CDRL3 comprises the amino acid sequence of SEQ ID NO:27, the CDRH1 comprises the amino acid sequence of SEQ ID NO:28, the CDRH2 comprises the amino acid sequence of SEQ ID NO:29, and the CDRH3 comprises the amino acid sequence of SEQ ID NO:30, the CDRL1 comprises the amino acid sequence of SEQ ID NO:1, the CDRL2 comprises the amino acid sequence EGN, the CDRL3 comprises the amino acid sequence of SEQ ID NO:3, the CDRH1 comprises the amino acid sequence of SEQ ID NO:4, the CDRH2 comprises the amino acid sequence of SEQ ID NO:5, and the CDRH3 comprises the amino acid sequence of SEQ ID NO:6, the CDRL1 comprises the amino acid sequence of SEQ ID NO:7, the CDRL2 comprises the amino acid sequence YTS, the CDRL3 comprises the amino acid sequence of SEQ ID NO:9, the CDRH1 comprises the amino acid sequence of SEQ ID NO:10, the CDRH2 comprises the amino acid sequence of SEQ ID NO:11, and the CDRH3 comprises the amino acid sequence of SEQ ID NO:12, the CDRL1 comprises the amino acid sequence of SEQ ID NO:13, the CDRL2 comprises the amino acid sequence WAS, the CDRL3 comprises the amino acid sequence of SEQ ID NO:15, the CDRH1 comprises the amino acid sequence of SEQ ID NO:16, the CDRH2 comprises the amino acid sequence of SEQ ID NO:17, and the CDRH3 comprises the amino acid sequence of SEQ ID NO:18, the CDRL1 comprises the amino acid sequence of SEQ ID NO:19, the CDRL2 comprises the amino acid sequence YTS, the CDRL3 comprises the amino acid sequence of SEQ ID NO:21, the CDRH1 comprises the amino acid sequence of SEQ ID NO:22, the CDRH2 comprises the amino acid sequence of SEQ ID NO:23, and the CDRH3 comprises the amino acid sequence of SEQ ID NO:24, or the CDRL1 comprises the amino acid sequence of SEQ ID NO:31, the CDRL2 comprises the amino acid sequence RAS, the CDRL3 comprises the amino acid sequence of SEQ ID NO:33, the CDRH1 comprises the amino acid sequence of SEQ ID NO:34, the CDRH2 comprises the amino acid sequence of SEQ ID NO:35, and the CDRH3 comprises the amino acid sequence of SEQ ID NO:36.

2. The antibody or fragment thereof of claim 1, wherein:
the CDRL1 comprises the amino acid sequence of SEQ ID NO:25,
the CDRL2 comprises the amino acid sequence YTS,
the CDRL3 comprises the amino acid sequence of SEQ ID NO:27,
the CDRH1 comprises the amino acid sequence of SEQ ID NO:28,
the CDRH2 comprises the amino acid sequence of SEQ ID NO:29, and
the CDRH3 comprises the amino acid sequence of SEQ ID NO:30.

3. The antibody or fragment thereof of claim 1, wherein the light chain variable region comprises the amino acid sequence of SEQ ID NO:56, and the heavy chain variable region comprises the amino acid sequence of SEQ ID NO:54.

4. The antibody or fragment thereof of claim 1, wherein:
the CDRL1 comprises the amino acid sequence of SEQ ID NO:13,
the CDRL2 comprises the amino acid sequence WAS,
the CDRL3 comprises the amino acid sequence of SEQ ID NO:15,
the CDRH1 comprises the amino acid sequence of SEQ ID NO:16,
the CDRH2 comprises the amino acid sequence of SEQ ID NO:17, and
the CDRH3 comprises the amino acid sequence of SEQ ID NO:18.

5. The antibody or fragment thereof of claim 4, wherein the light chain variable region comprises an amino acid sequence selected from the group consisting of SEQ ID NO: 48 and 82-83, and the heavy chain variable region comprises an amino acid sequence selected from the group consisting of SEQ ID NO: 46 and 80-81.

6. The antibody or fragment thereof of claim 1, which further has a binding specificity to a second target protein.

7. The antibody or fragment thereof of claim 6, wherein the second target protein is selected from the group consisting of IL-1, CD3, CD16, CD19, CD28, CD64, PD-1, PD-L1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, HEVM, BTLA and KIR.

8. A fusion protein comprising an antibody or fragment of claim 1, a blocking peptide, and a peptide linker connecting the antibody or fragment and the blocking peptide, wherein the peptide linker can be digested by a protease expressed in a tumor environment.

9. The fusion protein of claim 8, wherein the protease is selected from the group consisting of MMP-1, MMP-2, MMP-3, MMP-8, MMP-9, MMP-14, uPA, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase10, Caspase-11, Caspase-12, Caspase-13, Caspase-14, and TACE.

10. A composition comprising the antibody or fragment thereof of claim 1 and a pharmaceutically acceptable carrier.

11. An isolated cell comprising one or more polynucleotide encoding the antibody or fragment thereof of claim 1.

12. A method of treating CD47 expressing cancer in a patient in need thereof, comprising administering to the patient the antibody or fragment thereof of claim 1.

13. The method of claim 12, wherein the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

14. A method of treating fibrosis in a patient in need thereof, comprising administering to the patient the antibody or fragment thereof of claim 1.

15. A method of detecting expression of a CD47 protein in a sample, comprising contacting the sample with an antibody or fragment thereof of claim 1 under conditions for the antibody or fragment thereof to bind to the CD47 protein, and detecting the binding which indicates expression of CD47 protein in the sample.

16. The antibody or fragment thereof of claim 1, which is capable of binding to a human CD47 protein on a cell, blocking the binding of the CD47 protein to a human signal-regulatory protein alpha (SIRPα), and promoting macrophage phagocytosis of the cell.

17. The antibody or fragment thereof of claim 3, which does not induce hemagglutination in vitro.

* * * * *

SEQUENCE LISTING

```
<160> NUMBER OF SEQ ID NOS: 82

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Thr Asp Ile Asp Asp Asp
1               5

<210> SEQ ID NO 2
<211> LENGTH: 112
<212> TYPE: PRT
<213> ORGANISM: Artificial Sequence
<220> FEATURE:
<223> OTHER INFORMATION: Synthetic

<400> SEQUENCE: 2

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Phe Lys Ser
            20                  25                  30

Arg Thr Arg Lys Asn Tyr Leu Ala Trp Tyr Leu Gln Lys Pro Gly Gln
        35                  40                  45

Ser Pro Gln Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95
```

```
Ser Tyr Tyr Leu Leu Thr Phe Gly Gly Gly Thr Lys Val Glu Ile Lys
            100                 105                 110
```

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

```
Leu Gln Ser Asp Asn Leu Pro Tyr Thr
1               5
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Phe Thr Phe Thr Ser Tyr Gly
1               5
```

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

```
Ile Asn Thr Gly Gly Ser Tyr Thr
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

```
His Thr Ile Lys Ser Leu Met Asp Tyr
1               5
```

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

```
Gln Asp Ile Ser Asn His
1               5
```

<210> SEQ ID NO 8
<211> LENGTH: 363
<212> TYPE: DNA
<213> ORGANISM: Artificial Sequence
<220> FEATURE:
<223> OTHER INFORMATION: Synthetic

<400> SEQUENCE: 8

-continued

```
gaggtgcaac tcgtagaatc aggggggcgga ctcgttcaac ctggcgggag tcttagactt      60
agttgtgctg catcaggctt tacattttca cgctactgga tgaattgggt ccggcaggct     120
cccggaaaag gtctggaatg ggtagggcag attcggctca aatcagataa ttacgaaact     180
cactacgcgg aatcagtgaa gggacggttt acaatcagtc gcgatgatag taagaacagt     240
ttgtatttgc agatgaacag tttgaaaaca gaagacaccg ctgtctatta ctgcgctaga     300
gaaggcggat actatgtccc atttgcgtac tggggacaag ggaccctcgt aactgtttcc     360
agc                                                                   363
```

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Gln Gln Gly Ser Thr Leu Pro Phe Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Phe Asn Ile Lys Asn Thr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Ile Asp Pro Ala Asn Gly Asn Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gly Tyr Gly Ser Gly Phe Ala Tyr
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

Gln Ser Leu Phe Lys Ser Arg Thr Arg Lys Asn Tyr
1               5                   10

<210> SEQ ID NO 14
<211> LENGTH: 363
<212> TYPE: DNA
<213> ORGANISM: Artificial Sequence
<220> FEATURE:
<223> OTHER INFORMATION: Synthetic

<400> SEQUENCE: 14

```
gaggtgcaac tcgtagaatc aggggggcgga ctcgttcaac ctggcgggag tcttagactt      60
agttgtgctg catcaggctt acatttttca cgctactgga tgaattgggt ccggcaggct     120
cccggaaaag gtctggaatg ggtagggcag attcggctca aatcagataa ttacgaaact     180
cactacgcgg aatcagtgaa gggacggttt acaatcagtc gcgatgatag taagaacagt     240
ttgtatttgc agatgaacag tttgaaaaca gaagacaccg ctgtctatta ctgcattgaa     300
gaaggcggat actatgtccc atttgcgtac tggggacaag ggaccctcgt aactgtttcc     360
agc                                                                    363
```

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Lys Gln Ser Tyr Tyr Leu Leu Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gly Phe Thr Phe Ser Arg Tyr Trp
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Ile Arg Leu Lys Ser Asp Asn Tyr Glu Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Ile Glu Glu Gly Gly Tyr Tyr Val Pro Phe Ala Tyr
1               5                   10

<210> SEQ ID NO 19
<211> LENGTH: 6

```
<212> TYPE: PRT
<213> ORGANISM: Artificial Sequence
<220> FEATURE:
<223> OTHER INFORMATION: Synthetic

<400> SEQUENCE: 19

Gln Asp Ile Ser Asn His
1               5

<210> SEQ ID NO 20
<211> LENGTH: 363
<212> TYPE: DNA
<213> ORGANISM: Artificial Sequence
<220> FEATURE:
<223> OTHER INFORMATION: Synthetic

<400> SEQUENCE: 20
gaggtgcaac tcgtagaatc aggggggcgga ctcgttcaac ctggcgggag tcttagactt      60
agttgtgctg catcaggctt tacattttca cgctactgga tgaattgggt ccggcaggct     120
cccggaaaag gtctggaatg ggtagcgcag attcggctca atcagataa ttacgaaact      180 cactacgcgg aatcagtgaa gggacggttt acaatcagtc gcgatgatag taagagcagt     240
ttgtatttgc agatgaacag tttgaaaaca gaagacaccg ctgtctatta ctgcattgaa     300
gaaggcggat actatgtccc atttgcgtac tggggacaag ggaccctcgt aactgtttcc     360
agc                                                                   363

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Gln Gln Gly Ser Thr Leu Pro Phe Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Asn Ile Lys Asn Thr Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Ile Asp Pro Ala Asn Gly Asn Thr
1               5

<210> SEQ ID NO 24
<211> LENGTH: 8
<212> TYPE: PRT
<213> ORGANISM: Artificial Sequence
<220> FEATURE:
```

<223> OTHER INFORMATION: Synthetic

<400> SEQUENCE: 24

Gly Tyr Gly Ser Gly Phe Ala Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Gln Asp Ile Ser Asn His
1               5

<210> SEQ ID NO 26
<211> LENGTH: 336
<212> TYPE: DNA
<213> ORGANISM: Artificial Sequence
<220> FEATURE:
<223> OTHER INFORMATION: Synthetic

<400> SEQUENCE: 26
gacatcgtga tgacacagtc tcctgacagc cttgcggtct cactggggga acgcgcgaca      60
attaactgca atcctctca gtcactgttc aagagcagga cccgaaaaaa ttatctggca     120
tggtatcagc agaaacctgg acagccgcca aaactgctca tctactgggc gtcaatacgc     180
gaaagtggag tgccggatcg gttcagtgga tcaggttctg gcacagattt tacccttacg     240
atctccagtt tgcaggcgga agacgtagca gtatactact gcaaacagtc ttactacctt     300
cttaccttcg gaggtggcac taaggtagag atcaaa                              336

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Gln Gln Gly Ser Thr Phe Pro Tyr Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Gly Phe Asn Ile Lys Asp Thr Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Ile Asp Pro Ala Asn Gly Asn Ile

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ser Tyr Gly Ser Ser Phe Ala Ser
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Glu Ser Val Asp Glu Phe Gly Ile Ser Tyr
1               5                   10

<210> SEQ ID NO 32
<211> LENGTH: 336
<212> TYPE: DNA
<213> ORGANISM: Artificial Sequence
<220> FEATURE:
<223> OTHER INFORMATION: Synthetic

<400> SEQUENCE: 32

```
gatatagtaa tgacccagac gcctctgtca ctccccgtca caccagggga acctgcgtct    60
ataagttgca aatcatcaca atctctcttc aagtctcgga ctcggaaaaa ctacttggcc   120
tggtacttgc agaagccggg gcaaagtcct cagcttctca tatattgggc atccatccgg   180
gagtccggtg taccagaccg gttttcaggg tctggctcag ggaccgattt cactttgaaa   240
ataagccggg tggaagctga ggatgtagga gtctattact gcaaacagtc ttattatctg   300
ctcacgttcg gaggtggcac caaagttgag atcaaa                             336
```

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Gln Gln Ser Asn Gln Asp Pro Leu Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Gly Phe Thr Phe Ser Asp Tyr Gly
1               5

<210> SEQ ID NO 35
<211> LENGTH: 8

```
<212> TYPE: PRT
<213> ORGANISM: Artificial Sequence
<220> FEATURE:
<223> OTHER INFORMATION: Synthetic

<400> SEQUENCE: 35

Ile Ser Lys Tyr Gly Thr Tyr Thr
1               5

<210> SEQ ID NO 36
<211> LENGTH: 13
<212> TYPE: PRT
<213> ORGANISM: Artificial Sequence
<220> FEATURE:
<223> OTHER INFORMATION: Synthetic

<400> SEQUENCE: 36

Arg Phe Phe Gly Asn Tyr Asn Tyr Trp Tyr Phe Asp Val
1               5                   10

<210> SEQ ID NO 37
<211> LENGTH: 351
<212> TYPE: DNA
<213> ORGANISM: Artificial Sequence
<220> FEATURE:
<223> OTHER INFORMATION: Synthetic

<400> SEQUENCE: 37
gaggttcagc tgcagcagtc tgtggcagag cttgtgaggc caggggcctc agtcaagttg    60
tcctgcacag tttctggctt caacattaaa aatacttata tatactgggt gaagcagagg   120
cctgaacagg gtctggagtg gattggaagg attgatcctg cgaatggtaa tactaaagat   180
gccccgaagt tccagggcaa ggccactatg actgcagaca catcctccaa cacggcctac   240
ctacagctca gtagcctgac atctgaggac actgccatct attactgtgc tagaggctac   300
ggtagtggct ttgcttactg gggccaaggg actctggtca ctgtctctgc a             351

<210> SEQ ID NO 38
<211> LENGTH: 117
<212> TYPE: PRT
<213> ORGANISM: Artificial Sequence
<220> FEATURE:
<223> OTHER INFORMATION: Synthetic

<400> SEQUENCE: 38

Glu Val Gln Leu Gln Gln Ser Val Ala Glu Leu Val Arg Pro Gly Ala
1               5                   10                  15

Ser Val Lys Leu Ser Cys Thr Val Ser Gly Phe Asn Ile Lys Asn Thr
                20                  25                  30

Tyr Ile Tyr Trp Val Lys Gln Arg Pro Glu Gln Gly Leu Glu Trp Ile
            35                  40                  45

Gly Arg Ile Asp Pro Ala Asn Gly Asn Thr Lys Asp Ala Pro Lys Phe
        50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Arg Gly Tyr Gly Ser Gly Phe Ala Tyr Trp Gly Gln Gly Thr Leu
                100                 105                 110

Val Thr Val Ser Ala
            115
```

<210> SEQ ID NO 39
<211> LENGTH: 321
<212> TYPE: DNA
<213> ORGANISM: Artificial Sequence
<220> FEATURE:
<223> OTHER INFORMATION: Synthetic

<400> SEQUENCE: 39

```
gatatccaga tgacacagac tacatcctcc ctgtctgcct ctctgggaga cagagtcacc    60
atcagttgca gggccagtca ggacattagc aatcatttaa actggtatca gcagaaacca   120
gatggaattg ttaaactcct gatctactac acatcaagat acactcagg agtcccatca   180 aggttcagtg gcagtgggtc tgggacagat tattctctca ccattagcaa cctggaacaa   240
gaagatattg ccacttactt ttgccaacag ggtagtacgc ttccattcac gttcggctcg   300
gggacaaagt tggaaataaa a                                             321
```

<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30

Leu Asn Trp Tyr Gln Gln Lys Pro Asp Gly Ile Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Phe
                85                  90                  95

Thr Phe Gly Ser Gly Thr Lys Leu Glu Ile Lys
            100                 105
```

<210> SEQ ID NO 41
<211> LENGTH: 354
<212> TYPE: DNA
<213> ORGANISM: Artificial Sequence
<220> FEATURE:
<223> OTHER INFORMATION: Synthetic

<400> SEQUENCE: 41

```
gaggtgcagc tggtggagtc tgggggagac ttagtgaagc ctggagggtc cctgaaactc    60
tcctgtgcag cctctggatt cactttcact agctatggca tgtcttgggt tcgccagact   120
ccagacaaga ggctggagtg gtcgcaacc attaatactg gtggtagtta cacctactat   180
ccagacagtg tgaaggggcg attcaccatc tccagacaca tgccaagaa caccctgtac   240 ctgcaaatga gcagtctgaa gtctgaggac acagccatgt attactgtgc aagacatact   300
attaaatctc ttatggacta ctggggtcaa ggaacctcag tcaccgtctc ctca         354
```

<210> SEQ ID NO 42
<211> LENGTH: 118
<212> TYPE: PRT

<213> ORGANISM: Artificial Sequence
<220> FEATURE:
<223> OTHER INFORMATION: Synthetic

<400> SEQUENCE: 42

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Thr Ser Tyr
            20                  25                  30

Gly Met Ser Trp Val Arg Gln Thr Pro Asp Lys Arg Leu Glu Trp Val
        35                  40                  45

Ala Thr Ile Asn Thr Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Thr Ile Lys Ser Leu Met Asp Tyr Trp Gly Gln Gly Thr
            100                 105                 110

Ser Val Thr Val Ser Ser
        115

<210> SEQ ID NO 43
<211> LENGTH: 321
<212> TYPE: DNA
<213> ORGANISM: Artificial Sequence
<220> FEATURE:
<223> OTHER INFORMATION: Synthetic

<400> SEQUENCE: 43
gaaacaactg tgacccagtc tccagcatcc ctgtccatgg ctataggaga aaaagtcacc    60
atcagatgca taaccagcac tgatattgat gatgatatga actggtacca gcagaagcca   120
ggggaacctc ctaagctcct tatttcagaa ggcaatactc ttcgtcctgg agtcccatcc   180
cgattctcca gcagtggcta tggtacagat tttgttttta taattgaaaa catgttctca   240
gaagatgttg cagattacta ctgtttgcaa agtgataact tgccgtatac gttcggatcg   300
gggaccaagc tggaaataaa a                                             321

<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Ile Ile Glu Asn Met Phe Ser
65                  70                  75                  80

Glu Asp Val Ala Asp Tyr Tyr Cys Leu Gln Ser Asp Asn Leu Pro Tyr
                85                  90                  95

Thr Phe Gly Ser Gly Thr Lys Leu Glu Ile Lys
            100                 105

<210> SEQ ID NO 45
<211> LENGTH: 333
<212> TYPE: DNA
<213> ORGANISM: Artificial Sequence
<220> FEATURE:
<223> OTHER INFORMATION: Synthetic

<400> SEQUENCE: 45
ttggtgcaac ctggaggatc catgaaactc tcctgtgttg cctctggatt cactttcagt     60
agatactgga tgaactgggt ccgccagtct ccagacaagg ggcttgagtg ggttgctcaa    120
attagattga aatctgataa ttatgaaaca cattatgcgg agtctgtgaa agggaggttc    180
accatctcaa gagatgattc aaaagtagt gtctacctgc aaatgaacaa cttaagggct    240
gaagacactg gaatttatta ttgtatagaa gagggggtt actacgtccc gtttgcttac    300
tggggccaag ggactctggt cactgtctct gca                                 333

<210> SEQ ID NO 46
<211> LENGTH: 121
<212> TYPE: PRT
<213> ORGANISM: Artificial Sequence
<220> FEATURE:
<223> OTHER INFORMATION: Synthetic

<400> SEQUENCE: 46

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Arg Tyr
            20                  25                  30

Trp Met Asn Trp Val Arg Gln Ser Pro Asp Lys Gly Leu Glu Trp Val
        35                  40                  45

Ala Gln Ile Arg Leu Lys Ser Asp Asn Tyr Glu Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ile Glu Glu Gly Gly Tyr Tyr Val Pro Phe Ala Tyr Trp Gly
            100                 105                 110

Gln Gly Thr Leu Val Thr Val Ser Ala
        115                 120

<210> SEQ ID NO 47
<211> LENGTH: 336
<212> TYPE: DNA
<213> ORGANISM: Artificial Sequence
<220> FEATURE:
<223> OTHER INFORMATION: Synthetic

<400> SEQUENCE: 47
gacattgtcg tgtcacagtc tccatcctcc ctggctgtgt cagcaggaga gaaggtcact     60
atgagctgca atccagtca gagtctgttc aaaagtagaa cccgaaagaa ctacttggct    120
tggtaccagc agagaccagg gcagtctcct aaactgctga tctactgggc atccattagg    180
gaatctgggg tccctgatcg cttcacaggc agtggatctg ggacagaatt cactctcacc    240
atcagcagtg tgcaggctga agacctggca gtttattact gcaagcaatc ttattatcta    300
ctcacgttcg gtgctgggac caaactggag ctgaaa                      336

<210> SEQ ID NO 48
<211> LENGTH: 112
<212> TYPE: PRT
<213> ORGANISM: Artificial Sequence
<220> FEATURE:
<223> OTHER INFORMATION: Synthetic

<400> SEQUENCE: 48

Asp Ile Val Val Ser Gln Ser Pro Ser Ser Leu Ala Val Ser Ala Gly
1               5                   10                  15

Glu Lys Val Thr Met Ser Cys Lys Ser Ser Gln Ser Leu Phe Lys Ser
            20                  25                  30

Arg Thr Arg Lys Asn Tyr Leu Ala Trp Tyr Gln Gln Arg Pro Gly Gln
        35                  40                  45

Ser Pro Lys Leu Leu Ile Tyr Trp Ala Ser Ile Arg Glu Ser Gly Val
    50                  55                  60

Pro Asp Arg Phe Thr Gly Ser Gly Ser Gly Thr Glu Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Leu Thr Phe Gly Ala Gly Thr Lys Leu Glu Leu Lys
            100                 105                 110

<210> SEQ ID NO 49
<211> LENGTH: 351
<212> TYPE: DNA
<213> ORGANISM: Artificial Sequence
<220> FEATURE:
<223> OTHER INFORMATION: Synthetic

<400> SEQUENCE: 49
gaggttcagc tgcagcagtc tgtggcagag cttgtgaggc caggggcctc agtcaagttg    60
tcctgcacac cttctggctt caacattaaa aacacttata tactgggt gagacagagg     120 cctgaacagg gtctggagtg gattggaagg attgatcctg cgaatggtaa tactaaagat   180
gccccgaagt tccagggcaa ggccactatg actgcagaca catcctccaa cacagcctac   240
ctacagctca gcagcctgac atctgaggac actgccatct attactgtgc tagaggctac   300
ggtagtggct ttgcttactg gggccaaggg actctggtca ctgtctctgc a            351

<210> SEQ ID NO 50
<211> LENGTH: 117
<212> TYPE: PRT
<213> ORGANISM: Artificial Sequence
<220> FEATURE:
<223> OTHER INFORMATION: Synthetic

<400> SEQUENCE: 50

Glu Val Gln Leu Gln Gln Ser Val Ala Glu Leu Val Arg Pro Gly Ala
1               5                   10                  15

Ser Val Lys Leu Ser Cys Thr Pro Ser Gly Phe Asn Ile Lys Asn Thr
            20                  25                  30

Tyr Ile Tyr Trp Val Arg Gln Arg Pro Glu Gln Gly Leu Glu Trp Ile
        35                  40                  45

Gly Arg Ile Asp Pro Ala Asn Gly Asn Thr Lys Asp Ala Pro Lys Phe
    50                  55                  60

Gln Gly Lys Ala Thr Met Thr Ala Asp Thr Ser Ser Asn Thr Ala Tyr

```
                65                  70                  75                  80
Leu Gln Leu Ser Ser Leu Thr Ser Glu Asp Thr Ala Ile Tyr Tyr Cys
                        85                  90                  95

Ala Arg Gly Tyr Gly Ser Gly Phe Ala Tyr Trp Gly Gln Gly Thr Leu
            100                 105                 110

Val Thr Val Ser Ala
        115

<210> SEQ ID NO 51
<211> LENGTH: 321
<212> TYPE: DNA
<213> ORGANISM: Artificial Sequence
<220> FEATURE:
<223> OTHER INFORMATION: Synthetic

<400> SEQUENCE: 51
gatatccaga tgacacagac tacatcctcc ctgtctgcct ctctgggaga cagagtcacc      60
atcagttgca ggccagtca  ggacattagc aatcatttaa actggtatca gcagaaacca    120
gatggaactg ttaaactcct gatctactac acatcaagat tacactcagg agtcccatca    180
aggttcagtg gcagtgggtc tgggacagat tattctctca ccattagcaa cctggaacaa    240
gaagatattg ccacttactt tgccaacag ggtagtacgc ttccattcac gttcggctcg     300
gggacaaagt tggaaataaa a                                              321

<210> SEQ ID NO 52
<211> LENGTH: 107
<212> TYPE: PRT
<213> ORGANISM: Artificial Sequence
<220> FEATURE:
<223> OTHER INFORMATION: Synthetic

<400> SEQUENCE: 52

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Leu Pro Phe
                85                  90                  95

Thr Phe Gly Ser Gly Thr Lys Leu Glu Ile Lys
            100                 105

<210> SEQ ID NO 53
<211> LENGTH: 351
<212> TYPE: DNA
<213> ORGANISM: Artificial Sequence
<220> FEATURE:
<223> OTHER INFORMATION: Synthetic

<400> SEQUENCE: 53
gaggttcagc tgcagcagtc tggggcagag cttgtgaagc caggggcctc agtcaagttg      60
tcctgcacag cttctggctt caacattaaa gacacctata tacactgggt gaagcagagg    120
cctgaacagg gcctggaatg gattggaagg attgatcctg cgaatggtaa tattaaatct    180
```

```
gacccgaagt tccagggcaa ggccactgta acagcagaca catcctccaa cacagcctac      240
ctgcagctca gcagcctgac atctgaggac actgccgtct attactgtgc taggtcttac      300
ggtagtagtt ttgcttcctg gggccagggg actctggtca ctgtctctcc a               351
```

<210> SEQ ID NO 54
<211> LENGTH: 117
<212> TYPE: PRT
<213> ORGANISM: Artificial Sequence
<220> FEATURE:
<223> OTHER INFORMATION: Synthetic
<400> SEQUENCE: 54

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Ile Lys Ser Asp Pro Lys Phe
    50                  55                  60

Gln Gly Lys Ala Thr Val Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Tyr Gly Ser Ser Phe Ala Ser Trp Gly Gln Gly Thr Leu
            100                 105                 110

Val Thr Val Ser Pro
        115
```

<210> SEQ ID NO 55
<211> LENGTH: 321
<212> TYPE: DNA
<213> ORGANISM: Artificial Sequence
<220> FEATURE:
<223> OTHER INFORMATION: Synthetic
<400> SEQUENCE: 55

```
gatatccaga tgacacagac tacatcctcc ctgtctgcct ctctgggaga cagagtcacc      60
atcagttgca gggccagtca ggacattagc aatcatttaa actggtatca gcagaaacca     120
gatggagctg ttaaactcct gatctactac acatcaagat tacactcagg agtcccatca     180
aggttcagtg gcagtgggtc tgggacagat tattctctca ccattagcaa cctggaacaa     240
gaagatattg ccacttactt ttgccaacag ggtagtacgt ttccgtacac gttcggaggg     300
gggaccaagc tggaaataaa a                                                321
```

<210> SEQ ID NO 56
<211> LENGTH: 107
<212> TYPE: PRT
<213> ORGANISM: Artificial Sequence
<220> FEATURE:
<223> OTHER INFORMATION: Synthetic
<400> SEQUENCE: 56

```
Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn His
            20                  25                  30
```

Leu Asn Trp Tyr Gln Gln Lys Pro Asp Gly Ala Val Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Ser Thr Phe Pro Tyr
                85                  90                  95

Thr Phe Gly Gly Gly Thr Lys Leu Glu Ile Lys
            100                 105

<210> SEQ ID NO 57
<211> LENGTH: 366
<212> TYPE: DNA
<213> ORGANISM: Artificial Sequence
<220> FEATURE:
<223> OTHER INFORMATION: Synthetic

<400> SEQUENCE: 57
gaggtgcagc tggtggagtc tgggggagac ctagtgaaac ctggagggtc cctgaacctc      60
tcctgtgcag cctctggatt cactttcagt gactatggca tgtcttgggt tcgccagact     120
ccagacatga ggctggagtg ggtcgcaacc attagtaagt atggtactta tacgtcctat     180
ccggacagtg taaaggggcg attcaccatc tccagaagca atgccaagaa tacctatac     240 ctacaaatga gcagtctgaa gtctgcggac actgccctat attactgtgc aagacgtttc     300
tttggtaact acaactactg gtacttcgat gtgtggggcg cagggaccac ggtcaccgtc     360
tcctca                                                                366

<210> SEQ ID NO 58
<211> LENGTH: 122
<212> TYPE: PRT
<213> ORGANISM: Artificial Sequence
<220> FEATURE:
<223> OTHER INFORMATION: Synthetic

<400> SEQUENCE: 58

Glu Val Gln Leu Val Glu Ser Gly Gly Asp Leu Val Lys Pro Gly Gly
1               5                   10                  15

Ser Leu Asn Leu Ser Cys Ala Ala Ser Gly Phe Thr Phe Ser Asp Tyr
            20                  25                  30

Gly Met Ser Trp Val Arg Gln Thr Pro Asp Met Arg Leu Glu Trp Val
        35                  40                  45

Ala Thr Ile Ser Lys Tyr Gly Thr Tyr Thr Ser Tyr Pro Asp Ser Val
    50                  55                  60

Lys Gly Arg Phe Thr Ile Ser Arg Ser Asn Ala Lys Asn Thr Leu Tyr
65                  70                  75                  80

Leu Gln Met Ser Ser Leu Lys Ser Ala Asp Thr Ala Leu Tyr Tyr Cys
                85                  90                  95

Ala Arg Arg Phe Phe Gly Asn Tyr Asn Tyr Trp Tyr Phe Asp Val Trp
            100                 105                 110

Gly Ala Gly Thr Thr Val Thr Val Ser Ser
        115                 120

<210> SEQ ID NO 59
<211> LENGTH: 333
<212> TYPE: DNA
<213> ORGANISM: Artificial Sequence
<220> FEATURE:

<223> OTHER INFORMATION: Synthetic

<400> SEQUENCE: 59

```
gacattgtgc tgacccaatc tccagcttct ttggctgtgt ctctaggcca gagggccacc        60
ttctcctgca gagccagcga aagtgttgat gagtttggca ttagttatat acactggtac       120
aagaagagcc aggacagcc acccaaactc ctcatctatc gtgcatccac cctagaatct        180
gggatctctg ccaggttcag tgcagtggg tctgggacag acttcaccct caccattaat       240
cctgtggaga ctgatgatgt tgcaacctat tactgtcagc aaagtaatca ggatcctctc       300
acgttcggtg ctgggaccaa gctggaactg aaa                                    333
```

<210> SEQ ID NO 60
<211> LENGTH: 111
<212> TYPE: PRT
<213> ORGANISM: Artificial Sequence
<220> FEATURE:
<223> OTHER INFORMATION: Synthetic

<400> SEQUENCE: 60

Asp Ile Val Leu Thr Gln Ser Pro Ala Ser Leu Ala Val Ser Leu Gly
1               5                   10                  15

Gln Arg Ala Thr Phe Ser Cys Arg Ala Ser Glu Ser Val Asp Glu Phe
            20                  25                  30

Gly Ile Ser Tyr Ile His Trp Tyr Lys Lys Ser Pro Gly Gln Pro Pro
        35                  40                  45

Lys Leu Leu Ile Tyr Arg Ala Ser Thr Leu Glu Ser Gly Ile Ser Ala
    50                  55                  60

Arg Phe Ser Gly Ser Gly Ser Gly Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Gln Asp Pro Leu Thr Phe Gly Ala Gly Thr Lys Leu Glu Leu Lys
            100                 105                 110

<210> SEQ ID NO 61
<211> LENGTH: 118
<212> TYPE: PRT
<213> ORGANISM: Artificial Sequence
<220> FEATURE:
<223> OTHER INFORMATION: Synthetic

<400> SEQUENCE: 61

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Thr Ile Asn Thr Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Thr Ile Lys Ser Leu Met Asp Tyr Trp Gly Gln Gly Thr
            100                 105                 110

Thr Val Thr Val Ser Ser

-continued

```
<210> SEQ ID NO 62
<211> LENGTH: 118
<212> TYPE: PRT
<213> ORGANISM: Artificial Sequence
<220> FEATURE:
<223> OTHER INFORMATION: Synthetic

<400> SEQUENCE: 62
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Ser Tyr
            20                  25                  30

Gly Met Ser Trp Val Arg Gln Ala Pro Gly Lys Gly Leu Glu Trp Val
        35                  40                  45

Ala Thr Ile Asn Thr Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Thr Ile Lys Ser Leu Met Asp Tyr Trp Gly Gln Gly Thr
            100                 105                 110

Thr Val Thr Val Ser Ser
        115

```
<210> SEQ ID NO 63
<211> LENGTH: 118
<212> TYPE: PRT
<213> ORGANISM: Artificial Sequence
<220> FEATURE:
<223> OTHER INFORMATION: Synthetic

<400> SEQUENCE: 63
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Arg Leu Glu Trp Val
        35                  40                  45

Ser Thr Ile Asn Thr Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Thr Ile Lys Ser Leu Met Asp Tyr Trp Gly Gln Gly Thr
            100                 105                 110

Thr Val Thr Val Ser Ser
        115

```
<210> SEQ ID NO 64
<211> LENGTH: 107
<212> TYPE: PRT
<213> ORGANISM: Artificial Sequence
<220> FEATURE:
<223> OTHER INFORMATION: Synthetic

<400> SEQUENCE: 64
```

Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Gly Asn Thr Leu Arg Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Tyr
                85                  90                  95

Thr Phe Gly Gln Gly Thr Lys Leu Glu Ile Lys
            100                 105

<210> SEQ ID NO 65
<211> LENGTH: 107
<212> TYPE: PRT
<213> ORGANISM: Artificial Sequence
<220> FEATURE:
<223> OTHER INFORMATION: Synthetic

<400> SEQUENCE: 65

Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Leu Ile Ile
            35                  40                  45

Gln Glu Gly Asn Thr Leu Arg Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Tyr
                85                  90                  95

Thr Phe Gly Gln Gly Thr Lys Leu Glu Ile Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: Synthetic

<400> SEQUENCE: 66

Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Leu Ile Ile
            35                  40                  45

Gln Glu Gly Asn Thr Leu Arg Pro Gly Val Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Tyr

```
                    85                  90                  95

Thr Phe Gly Gln Gly Thr Lys Leu Glu Ile Lys
                100                 105

<210> SEQ ID NO 67
<211> LENGTH: 107
<212> TYPE: PRT
<213> ORGANISM: Artificial Sequence
<220> FEATURE:
<223> OTHER INFORMATION: Synthetic

<400> SEQUENCE: 67

Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Leu Leu Ile
            35                  40                  45

Gln Glu Gly Asn Thr Leu Arg Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Tyr
                85                  90                  95

Thr Phe Gly Gln Gly Thr Lys Leu Glu Ile Lys
                100                 105

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Leu Leu Ile
            35                  40                  45

Ser Glu Gly Asn Thr Leu Arg Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Tyr
                85                  90                  95

Thr Phe Gly Gln Gly Thr Lys Leu Glu Ile Lys
                100                 105

<210> SEQ ID NO 69
<211> LENGTH: 107
<212> TYPE: PRT
<213> ORGANISM: Artificial Sequence
<220> FEATURE:
<223> OTHER INFORMATION: Synthetic

<400> SEQUENCE: 69

Glu Thr Thr Leu Thr Gln Ser Pro Ala Phe Met Ser Ala Thr Pro Gly
1               5                   10                  15
```

Asp Lys Val Thr Ile Arg Cys Ile Thr Ser Thr Asp Ile Asp Asp
         20                  25                  30

Met Asn Trp Tyr Gln Gln Lys Pro Gly Glu Ala Ala Ile Leu Ile Ile
         35                  40                  45

Gln Glu Gly Asn Thr Leu Arg Pro Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln Ser Asp Asn Leu Pro Tyr
             85                  90                  95

Thr Phe Gly Gln Gly Thr Lys Leu Glu Ile Lys
             100                 105

<210> SEQ ID NO 70
<211> LENGTH: 354
<212> TYPE: DNA
<213> ORGANISM: Artificial Sequence
<220> FEATURE:
<223> OTHER INFORMATION: Synthetic

<400> SEQUENCE: 70
gaggtacagt tggtcgaatc cggtgggggg cttgtgaagc ccggaggcag cttgcggctc      60
tcatgtgctg caagtggctt cactttctcc tcatacggca tgagttgggt acgacaagcg     120
ccaggaaaag ggcttgaatg ggtgagcacc atcaataccg gaggatcata cacttattac     180
ccagatagtg tcaagggtag attcaccatc tccagggata tgcaaagaa tagtttgtac      240 ttgcagatga acagcttgag agcagaggac actgccgtgt attactgcgc tcgccatacg     300
attaagagtt tgatggacta ctggggtcaa ggtactaccg tcacagtcag ttca           354

<210> SEQ ID NO 71
<211> LENGTH: 354
<212> TYPE: DNA
<213> ORGANISM: Artificial Sequence
<220> FEATURE:
<223> OTHER INFORMATION: Synthetic

<400> SEQUENCE: 71
gaggtacagt tggtcgaatc cggtgggggg cttgtgaagc ccggaggcag cttgcggctc      60
tcatgtgctg caagtggctt cactttcacc tcatacggca tgagttgggt acgacaagcg     120
ccaggaaaag ggcttgaatg ggtggccacc atcaataccg gaggatcata cacttattac     180
ccagatagtg tcaagggtag attcaccatc tccagggata tgcaaagaa tagtttgtac      240 ttgcagatga acagcttgag agcagaggac actgccgtgt attactgcgc tcgccatacg     300
attaagagtt tgatggacta ctggggtcaa ggtactaccg tcacagtcag ttca           354

<210> SEQ ID NO 72
<211> LENGTH: 354
<212> TYPE: DNA
<213> ORGANISM: Artificial Sequence
<220> FEATURE:
<223> OTHER INFORMATION: Synthetic

<400> SEQUENCE: 72
gaggtacagt tggtcgaatc cggtgggggg cttgtgaagc ccggaggcag cttgcggctc      60
tcatgtgctg caagtggctt cactttctcc tcatacggca tgagttgggt acgacaagcg     120
ccaggaaaac ggcttgaatg ggtgagcacc atcaataccg gaggatcata cacttattac     180

```
ccagatagtg tcaagggtag attcaccatc tccagggata atgcaaagaa tagtttgtac    240
ttgcagatga acagcttgag agcagaggac actgccgtgt attactgcgc tcgccatacg    300
attaagagtt tgatggacta ctggggtcaa ggtactaccg tcacagtcag ttca          354
```

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73

```
gaaaccaccc tcacccaaag tccagccttt atgtccgcca ctcccggaga caaggtaaac     60
atttcttgta taacgtcaac ggacattgac gatgacatga attggtacca acaaaagccg    120
ggggaagccg ctattttcat aattcaagaa ggtaatacgc tcagacccgg aatcccctcct  180 cgctttagtg gtagcggtta cggcacggac ttcacattga cgattaacaa catcgagtct   240
gaagacgctg cgtattattt ctgccttcaa agtgataacc tgccttatac gttcggacaa   300
ggtactaaat tggagattaa g                                              321
```

<210> SEQ ID NO 74
<211> LENGTH: 321
<212> TYPE: DNA
<213> ORGANISM: Artificial Sequence
<220> FEATURE:
<223> OTHER INFORMATION: Synthetic

<400> SEQUENCE: 74

```
gaaaccaccc tcacccaaag tccagccttt atgtccgcca ctcccggaga caaggtaaac     60
atttcttgta taacgtcaac ggacattgac gatgacatga attggtacca acaaaagccg    120
ggggaagccg ctattctcat aattcaagaa ggtaatacgc tcagacccgg aatcccctcct  180 cgctttagtg gtagcggtta cggcacggac ttcacattga cgattaacaa catcgagtct   240
gaagacgctg cgtattattt ctgccttcaa agtgataacc tgccttatac gttcggacaa   300
ggtactaaat tggagattaa g                                              321
```

<210> SEQ ID NO 75
<211> LENGTH: 321
<212> TYPE: DNA
<213> ORGANISM: Artificial Sequence
<220> FEATURE:
<223> OTHER INFORMATION: Synthetic

<400> SEQUENCE: 75

```
gaaaccaccc tcacccaaag tccagccttt atgtccgcca ctcccggaga caaggtaaac     60
atttcttgta taacgtcaac ggacattgac gatgacatga attggtacca acaaaagccg    120
ggggaagccg ctattctcat aattcaagaa ggtaatacgc tcagacccgg agtccctcct   180
cgctttagtg gtagcggtta cggcacggac ttcacattga cgattaacaa catcgagtct   240
gaagacgctg cgtattattt ctgccttcaa agtgataacc tgccttatac gttcggacaa   300
ggtactaaat tggagattaa g                                              321
```

<210> SEQ ID NO 76
<211> LENGTH: 321
<212> TYPE: DNA
<213> ORGANISM: Artificial Sequence
<220> FEATURE:
<223> OTHER INFORMATION: Synthetic

<400> SEQUENCE: 76

```
gaaaccaccc tcacccaaag tccagccttt atgtccgcca ctcccggaga caaggtaaac    60
atttcttgta taacgtcaac ggacattgac gatgacatga attggtacca acaaaagccg   120
ggggaagccg ctattctcct aattcaagaa ggtaatacgc tcagacccgg aatccctcct   180
cgctttagtg gtagcggtta cggcacggac ttcacattga cgattaacaa catcgagtct   240
gaagacgctg cgtattattt ctgccttcaa agtgataacc tgccttatac gttcggacaa   300
ggtactaaat tggagattaa g                                             321
```

<210> SEQ ID NO 77
<211> LENGTH: 321
<212> TYPE: DNA
<213> ORGANISM: Artificial Sequence
<220> FEATURE:
<223> OTHER INFORMATION: Synthetic

<400> SEQUENCE: 77

```
gaaaccaccc tcacccaaag tccagccttt atgtccgcca ctcccggaga caaggtaaac    60
atttcttgta taacgtcaac ggacattgac gatgacatga attggtacca acaaaagccg   120
ggggaagccg ctattctcct aatttcagaa ggtaatacgc tcagacccgg aatccctcct   180
cgctttagtg gtagcggtta cggcacggac ttcacattga cgattaacaa catcgagtct   240
gaagacgctg cgtattattt ctgccttcaa agtgataacc tgccttatac gttcggacaa   300
ggtactaaat tggagattaa g                                             321
```

<210> SEQ ID NO 78
<211> LENGTH: 321
<212> TYPE: DNA
<213> ORGANISM: Artificial Sequence
<220> FEATURE:
<223> OTHER INFORMATION: Synthetic

<400> SEQUENCE: 78

```
gaaaccaccc tcacccaaag tccagccttt atgtccgcca ctcccggaga caaggtaacc    60
attcgttgta taacgtcaac ggacattgac gatgacatga attggtacca acaaaagccg   120
ggggaagccg ctattctcat aattcaagaa ggtaatacgc tcagacccgg aatccctcct   180
cgctttagtg gtagcggtta cggcacggac ttcacattga cgattaacaa catcgagtct   240
gaagacgctg cgtattattt ctgccttcaa agtgataacc tgccttatac gttcggacaa   300
ggtactaaat tggagattaa g                                             321
```

<210> SEQ ID NO 79
<211> LENGTH: 121
<212> TYPE: PRT
<213> ORGANISM: Artificial Sequence
<220> FEATURE:
<223> OTHER INFORMATION: Synthetic

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Asn Trp Val Arg Gln Ala Pro Gly Lys Gly Leu Glu Trp Val
        35                  40                  45

Gly Gln Ile Arg Leu Lys Ser Asp Asn Tyr Glu Thr His Tyr Ala Glu
```

```
                    50                  55                  60
Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Ala Arg Glu Gly Gly Tyr Tyr Val Pro Phe Ala Tyr Trp Gly
                100                 105                 110

Gln Gly Thr Leu Val Thr Val Ser Ser
            115                 120

<210> SEQ ID NO 80
<211> LENGTH: 121
<212> TYPE: PRT
<213> ORGANISM: Artificial Sequence
<220> FEATURE:
<223> OTHER INFORMATION: Synthetic

<400> SEQUENCE: 80

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
                 20                  25                  30

Trp Met Asn Trp Val Arg Gln Ala Pro Gly Lys Gly Leu Glu Trp Val
             35                  40                  45

Gly Gln Ile Arg Leu Lys Ser Asp Asn Tyr Glu Thr His Tyr Ala Glu
         50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                     85                  90                  95

Tyr Cys Ile Glu Glu Gly Gly Tyr Tyr Val Pro Phe Ala Tyr Trp Gly
                100                 105                 110

Gln Gly Thr Leu Val Thr Val Ser Ser
            115                 120

<210> SEQ ID NO 81
<211> LENGTH: 121
<212> TYPE: PRT
<213> ORGANISM: Artificial Sequence
<220> FEATURE:
<223> OTHER INFORMATION: Synthetic

<400> SEQUENCE: 81

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
                 20                  25                  30

Trp Met Asn Trp Val Arg Gln Ala Pro Gly Lys Gly Leu Glu Trp Val
             35                  40                  45

Ala Gln Ile Arg Leu Lys Ser Asp Asn Tyr Glu Thr His Tyr Ala Glu
         50                  55                  60

Ser Val Lys Gly Arg Phe Thr Ile Ser Arg Asp Asp Ser Lys Ser Ser
 65                  70                  75                  80

Leu Tyr Leu Gln Met Asn Ser Leu Lys Thr Glu Asp Thr Ala Val Tyr
                     85                  90                  95

Tyr Cys Ile Glu Glu Gly Gly Tyr Tyr Val Pro Phe Ala Tyr Trp Gly
                100                 105                 110
```

```
Gln Gly Thr Leu Val Thr Val Ser Ser
        115                 120

<210> SEQ ID NO 82
<211> LENGTH: 112
<212> TYPE: PRT
<213> ORGANISM: Artificial Sequence
<220> FEATURE:
<223> OTHER INFORMATION: Synthetic

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Lys Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Tyr Leu Leu Thr Phe Gly Gly Gly Thr Lys Val Glu Ile Lys
            100                 105                 110
```